US010385320B2

United States Patent
Kay et al.

(10) Patent No.: US 10,385,320 B2
(45) Date of Patent: Aug. 20, 2019

(54) RECOMBINANT ADENO-ASSOCIATED VIRUS CAPSIDS WITH ENHANCED HUMAN SKELETAL MUSCLE TROPISM

(71) Applicant: The Board of Trustees of the Leland Stanford Junior University, Palo Alto, CA (US)

(72) Inventors: Mark A. Kay, Los Altos, CA (US); Nicole K. Paulk, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/367,734

(22) Filed: Dec. 2, 2016

(65) Prior Publication Data

US 2017/0159026 A1    Jun. 8, 2017

Related U.S. Application Data

(60) Provisional application No. 62/336,078, filed on May 13, 2016, provisional application No. 62/268,428, (Continued)

(51) Int. Cl.
*C12N 7/00* (2006.01)
*A61K 39/00* (2006.01)
(Continued)

(52) U.S. Cl.
CPC ................ *C12N 7/00* (2013.01); *A61K 48/00* (2013.01); *A61K 48/0058* (2013.01); *C07K 14/005* (2013.01); *C12N 9/22* (2013.01); *C12N 15/86* (2013.01); *C12Y 301/00* (2013.01); *C12N 2710/10322* (2013.01); *C12N 2710/10331* (2013.01); *C12N 2710/10334* (2013.01);
(Continued)

(58) Field of Classification Search
None
See application file for complete search history.

(56) References Cited

U.S. PATENT DOCUMENTS

| 5,139,941 | A | 8/1992 | Muzyczka et al. |
| 5,173,414 | A | 12/1992 | Lebkowski et al. |

(Continued)

FOREIGN PATENT DOCUMENTS

| WO | WO 92/01070 A1 | 1/1992 |
| WO | WO 93/03769 A1 | 3/1993 |

(Continued)

OTHER PUBLICATIONS

Kessler et al., "Gene delivery to skeletal muscle results in sustained expression and systemic delivery of a therapeutic protein," PNAS, vol. 93: 14082-14087 (Year: 1996).*

(Continued)

*Primary Examiner* — M Franco G Salvoza
(74) *Attorney, Agent, or Firm* — Morgan Lewis & Bockius LLP

(57) ABSTRACT

The present invention relates to variant AAV capsid polypeptides, wherein the variant AAV capsid polypeptides exhibit increased transduction and/or tropism in human muscle tissue or cells as compared non-variant parent capsid polypeptides.

41 Claims, 11 Drawing Sheets
(7 of 11 Drawing Sheet(s) Filed in Color)
Specification includes a Sequence Listing.

Related U.S. Application Data filed on Dec. 16, 2015, provisional application No. 62/262,289, filed on Dec. 2, 2015.

(51) Int. Cl.

| A61K 48/00 | (2006.01) |
|---|---|
| C12N 9/22 | (2006.01) |
| C12N 15/86 | (2006.01) |
| C07K 14/005 | (2006.01) |

(52) U.S. Cl.
CPC ........... C12N 2710/10351 (2013.01); C12N 2750/14122 (2013.01); C12N 2750/14143 (2013.01); C12N 2750/14145 (2013.01); C12N 2750/14151 (2013.01)

(56) References Cited

U.S. PATENT DOCUMENTS

| 6,491,907 | B1 | 12/2002 | Rabinowitz et al. |
|---|---|---|---|
| 6,951,758 | B2 | 10/2005 | Ferrari et al. |
| 7,271,002 | B2 | 9/2007 | Kotin et al. |
| 7,439,065 | B2 | 10/2008 | Ferrari et al. |
| 2005/0053922 | A1 | 3/2005 | Schaffer et al. |
| 2009/0202490 | A1 | 8/2009 | Schaffer et al. |
| 2009/0203071 | A1 | 8/2009 | Chen |
| 2012/0164106 | A1 | 6/2012 | Schaffer et al. |
| 2014/0242031 | A1 | 8/2014 | Schaffer et al. |
| 2014/0348794 | A1 | 11/2014 | Chiorini et al. |
| 2015/0023924 | A1 | 1/2015 | High et al. |
| 2015/0176027 | A1 | 6/2015 | Gao et al. |

FOREIGN PATENT DOCUMENTS

| WO | WO 2013/029030 A1 | 2/2013 |
|---|---|---|
| WO | WO 2016/049230 A1 | 3/2016 |

OTHER PUBLICATIONS

Drouin et al., "Adeno-associated virus structural biology as a tool in vector development," Future Virol., 8(12): 1183-1199 (Year: 2013).*
Bello et al. "Novel Adeno-associated Viruses Derived From Pig Tissues Transduce Most Major Organs in Mice," Scientific Reports, vol. 4:6644, pp. 1-11 (2014).
Bünning et al. "Engineering the AAV capsid to optimize vector-host-interactions," Current Opinion in Pharmacology, vol. 24, pp. 94-104 (2015).
Hollinger and Chamberlain "Viral vector-mediated gene therapies," Neurology, vol. 28:5, pp. 522-527 (2015).
Jang et al. "An Evolved Adeno-associated Viral Variant Enhances Gene Delivery and Gene Targeting in Neural Stem Cells," Molecular Therapy, vol. 19:4, pp. 667-675 (2011).
Kienle et al. "Engineering and Evolution of Synthetic Adeno-Associated Virus (AAV) Gene Therapy Vectors via DNA Family Shuffling," Journal of Visualized Experiments, vol. 62, pp. 1-11 (2012).
Lisowski et al. "Selection and evaluation of clinically relevant AAV variants in a xenograft liver model," Nature, vol. 506, pp. 382-395 (2014).
Paulk et al., "Utilizing DNA Shuffling Technologies to Generate AAV Libraries to Select for and Evolve Capsids With an Expanded Packaging Capacity," Molecular Therapy, vol. 22:1, pp. S116 and S117 (2014).
Riaz et al. "Differential myofiber-type transduction preference of adeno-associated virus serotypes 6 and 9," Skeletal Muscle, vol. 5:37, pp. 1-10 (2015).
Santiago-Ortiz et al. "AAV ancestral reconstruction library enables selection of broadly infectious viral variants," Gene Therapy, vol. 22, pp. 934-946 (2015).
Shen et al. "Engraftment of a Galactose Receptor Footprint onto Adeno-associated Viral Capsids Improves Transduction Efficiency," Journal of Biological Chemistry, vol. 288:40, pp. 28814-28823 (2013).
Wang et al. "The potential of adeno-associated viral vectors for gene delivery to muscle tissue," Expert Opin Drug Deliv., vol. 11(3), pp. 345-364 (2014).
Yang et al. "A myocardium tropic adeno-associated virus (AAV) evolved by DNA shuffling and in vivo selection," PNAS, vol. 106:10, pp. 3946-3951 (2009).
Yang et al. "Directed Evolution of Adeno-Associated Virus (AAV) as Vector for Muscle Gene Therapy," Muscle Gene Therapy, vol. 709 of series Methods in Molecular Biology, pp. 127-139 (2010).
Arbetman et al. "Novel caprine adeno-associated virus (AAV) capsid (AAV-Go.1) is closely related to the primate AAV-5 and has unique tropism and neutralization properties" Journal of Virology vol. 79, No. 24, p. 15238-15245 (2005).
Azuma et al. "Robust expansion of human hepatocytes in Fah-/-/Rag2-/-/Il2rg-/-mice" Nature Biotechnology vol. 25, No. 8 p. 903-910 (2007).
Balazs et al. "Antibody-based protection against HIV infection by vectored immunoprophylaxis" Nature vol. 481, No. 7379, p. 81-84 (2012).
Balazs et al. "Broad protection against influenza infection by vectored immunoprophylaxis in mice" Nature Biotechnology, vol. 31, No. 7, p. 647-652 (2013).
Balazs et al. "Vectored ImmunoProphylaxis Protects Humanized Mice from Mucosal HIV Transmission" Nature Medicine vol. 20, No. 3, p. 296-300 (2014).
Boutin et al. "Prevalence of serum IgG and neutralizing factors against adeno-associated virus (AAV) types 1, 2, 5, 6, 8, and 9 in the healthy population: implications for gene therapy using AAV vectors" Human Gene Therapy vol. 21 p. 704-712 (2010).
Bowles et al. "Phase 1 Gene Therapy for Duchenne Muscular Dystrophy Using a Translational Optimized AAV Vector" Molecular Therapy vol. 20, No. 2, p. 443-455 (2012).
Brantly et al. "Sustained transgene expression despite T lymphocyte responses in a clinical trial of rAAV1-AAT gene therapy" Proceedings of the National Academy of Sciences of the United States of America vol. 106, No. 28, p. 16363-16368 (2009).
Calcedo and Wilson "Humoral Immune Response to AAV" Frontiers in Immunology vol. 4, No. 341 (2013).
Calcedo et al. "Adeno-associated virus antibody profiles in newborns, children, and adolescents" Clinical and Vaccine Immunology, vol. 18 No. 9, p. 1586-1588 (2011).
Calcedo et al. "Worldwide epidemiology of neutralizing antibodies to adeno-associated viruses" The Journal of Infectious Diseases vol. 199, No. 3 p. 381-390 (2009).
Carter "Adeno-associated virus vectors" Current Opinion in Biotechnology vol. 3, p. 533-539 (1992).
Chen "Intron Splicing-mediated Expression of AAV Rep and Cap Genes and Production of AAV Vectors in Insect Cells" Molecular Therapy, vol. 16, p. 924-930 (2008).
Croyle et al. "Development of formulations that enhance physical stability of viral vectors for gene therapy" Gene Therapy vol. 8, No. 17, p. 1281-1290 (2001).
Cunningham et al. "Gene delivery to the juvenile mouse liver using AAV2/8 vectors" Molecular Therapy: The Journal of the American Society of Gene Therapy vol. 16, No. 6, p. 1081-1088 (2008).
Dane et al. "Comparison of gene transfer to the murine liver following intraperitoneal and intraportal delivery of hepatotropic AAV pseudo-serotypes" Gene Therapy vol. 20, p. 460-464 (2013).
Davidoff et al. "Comparison of the ability of adeno-associated viral vectors pseudotyped with serotype 2, 5, and 8 capsid proteins to mediate efficient transduction of the liver in murine and nonhuman primate models" Molecular Therapy: The Journal of the American Society of Gene Therapy vol. 11 No. 6, p. 875-888 (2005).
D'Avola et al. "Phase I open label liver-directed gene therapy clinical trial for acute intermittent porphyria" Journal of Hepatology vol. 65, No. 4, p. 776-783 (2016).
Erles et al. "Update on the Prevalence of Serum Antibodies (IgG and IgM) to Adeno-Associated Virus (AAV)" Journal of Medical Virology vol. 59, p. 406-411 (1999).
Flotte et al. "Phase 2 clinical trial of a recombinant adeno-associated viral vector expressing alpha1-antitrypsin: interim results" Human gene therapy, vol. 22, p. 1239-1247 (2011).

(56) References Cited

OTHER PUBLICATIONS

Flotte et al. "Phase I trial of intramuscular injection of a recombinant adeno-associated virus alpha 1-antitrypsin (rAAV2-CB-hAAT) gene vector to AAT-deficient adults" Human Gene Therapy vol. 14, p. 93-128 (2004).
Foust et al. "Rescue of the spinal muscular atrophy phenotype in a mouse model by early postnatal delivery of SMN" Nature Biotechnology vol. 28, No. 3, p. 271-274 (2010).
Gray et al. "Directed evolution of a novel adeno-associated virus (AAV) vector that crosses the seizure-compromised blood-brain barrier (BBB)" Molecular Therapy: The Journal of the American Society of Gene Therapy vol. 18, No. 3 p. 570-578 (2010).
Greig et al. "Intramuscular administration of AAV overcomes pre-existing neutralizing antibodies in rhesus macaques" Vaccine vol. 34, p. 6323-6329 (2016).
Grieger and Samulski "Packaging Capacity of Adeno-Associated Virus Serotypes: Impact of Larger Genomes on Infectivity and Postentry Steps" Journal of Virology, vol. 79, No. 15, p. 9933-9944 (2005).
Grimm "Production methods for gene transfer vectors based on adeno-associated virus serotypes" Methods vol. 28, p. 146-157 (2002).
Grimm et al "In Vitro and In Vivo Gene Therapy Vector Evolution via Multispecies Interbreeding and Retargeting of Adeno-Associated Viruses" Journal of Virology, vol. 82, No. 12, p. 5887-5911 (2008).
Grimm et al. "Titration of AAV-2 particles via a novel capsid ELISA: packaging of genomes can limit production of recombinant AAV-2" Gene Therapy vol. 6, No. 7 p. 1322-1330 (1999).
Halbert et al. "Prevalence of neutralizing antibodies against adeno-associated virus (AAV) types 2, 5, and 6 in cystic fibrosis and normal populations: Implications for gene therapy using AAV vectors" Human Gene Therapy vol. 17, No. 4 p. 440-447 (2006).
Han et al. "Cost-Effectiveness Analysis of Glybera for the Treatment of Lipoprotein Lipase Deficiency" Value in Health: the journal of the Int'l Societr for Pharmacoeconomics and Outcomes Research vol. 18, p. A756 (2015).
Huch et al. "In vitro expansion of single Lgr5+ liver stem cells induced by Wnt-driven regeneration" Nature vol. 494, No. 7436, p. 247-250 (2013).
James T. Koerber et al "DNA Shuffling of Adeno-associated Virus Yields Functionally Diverse Viral Progeny" Molecular Therapy, vol. 16 No. 10, p. 1703-1709 (2008).
James T. Koerber et al "Molecular Evolution of Adeno-associated Virus for Enhanced Glial Gene Delivery" Molecular Therapy, vol. 17 No. 12, p. 2088-2095 (2009).
Jane S. Lebkowski et al "Adeno-Associated Virus: a Vector System for Efficient Introduction and Integration of DNA into a Variety of Mammalian Cell Types" Molecular and Cellular Biology, vol. 8, No. 10, p. 3988-3996 (1988).
Jang et al. "An evolved adeno-associated viral variant enhances gene delivery and gene targeting in neural stem cells" Molecular Therapy: The Journal of the American Society of Gene Therapy vol. 19, No. 4 p. 667-675 (2011).
Johnson et al. "Vector-mediated gene transfer engenders long-lived neutralizing activity and protection against SIV infection in monkeys" Nature medicine, vol. 15, No. 8, p. 901-906 (2009).
Kay "Selecting the Best AAV Capsid for Human Studies" Molecular Therapy: The Journal of the American Society of Gene Therapy vol. 23, No. 12 p. 1800-1801 (2015).
Kay et al. "Evidence for gene transfer and expression of factor IX in haemophilia B patients treated with an AAV vector" Nature Genetics vol. 24, p. 257-561 (2000).
Kienle et al. "Engineering and evolution of synthetic adeno-associated virus gene therapy vectors via DNA family shuffling" Journal of Visualized Experiments vol. 62, No. 3819, p. 1-11 (2012).
Kotin "Prospects for the Use of Adeno-Associated Virus as a Vector for Human Gene Therapy" Human Gene Therapy vol. 5, p. 793-801 (1994).
Kotterman and Schaffer "Engineering adeno-associated viruses for clinical gene therapy" Nature Reviews: Genetics vol. 15 No. 7, p. 445-451 (2014).
Kuck et al. "Intranasal Vaccination with Recombinant Adeno-Associated Virus Type 5 against Human Papillomavirus Type 16 L1" Journal of Virology, vol. 80, No. 6, p. 2621-2630 (2006).
Li et al. "Efficient and Targeted Transduction of Nonhuman Primate Liver With Systemically Delivered Optimized AAV3B Vectors" Molecular Therapy vol. 23, No. 12, p. 1867-1876 (2015).
Li et al. "Engineering and selection of shuffled AAV genomes: a new strategy for producing targeted biological nanoparticles" Molecular Therapy—The Journal of the American Society of Gene Therapy vol. 16, No. 7, p. 1252-1260 (2008).
Li et al. "Neutralizing antibodies against adeno-associated virus examined prospectively in pediatric patients with hemophilia" Gene Therapy, vol. 19, p. 288-294 (2012).
Limberis et al. "Intranasal Antibody Gene Transfer in Mice and Ferrets Elicits Broad Protection Against Pandemic Influenza" Science Translational Medicine vol. 5, Issue 187, p. 1-8 (2013).
Limberis et al. "Vectored expression of the broadly neutralizing antibody F16 in mouse airway provides partial protection against a new avian influenza A virus, H7N9" Clinical and Vaccine Immunology, vol. 20, No. 12, p. 1836-1837 (2013).
Lin et al. "A New Genetic Vaccine Platform Based on an Adeno-Associated Virus Isolated from a Rhesus Macaque" Journal of Virology, vol. 83, No. 24, p. 12738-12750 (2009).
Ling et al. "Prevalence of neutralizing antibodies against liver-tropic adeno-associated virus serotype vectors in 100 healthy Chinese and its potential relation to body constitutions" Journal of Integrative Medicine vol. 13, No. 5, p. 341-346 (2015).
Lisowski et al. "Selection and evaluation of clinically relevant AAV variants in a xenograft liver model" Nature, vol. 506, p. 382-386 (2014).
Liu et al. "Isolation of skeletal muscle stem cells by fluorescence-activated cell sorting" Nature Protocols vol. 10, No. 10, p. 1612-1624 (2015).
Liu et al. "Neutralizing antibodies against AAV2, AAV5 and AAV8 in healthy and HIV-1-infected subjects in China: implications for gene therapy using AAV vectors" Gene Therapy vol. 21, p. 732-738 (2014).
Liu et al. "The prevalence of neutralizing antibodies against AAV serotype 1 in healthy subjects in China: implications for gene therapy and vaccines using AAV1 vector" Journal of Medical Virology vol. 85, p. 1550-1556 (2013).
Lochrie et al. "Mutations on the external surfaces of adeno-associated virus type 2 capsids that affect transduction and neutralization" Journal of Virology, vol. 80, No. 2, p. 821-834 (2006).
Long et al. "Postnatal genome editing partially restores dystrophin expression in a mouse model of muscular dystrophy" Science vol. 351, No. 6271, p. 400-403 (2016).
Manno et al. "Successful transduction of liver in hemophilia by AAV-Factor IX and limitations imposed by the host immune response." Nature Medicine, vol. 12 p. 342-347 (2006).
Mao et al. "Single point mutation in adeno-associated viral vectors-DJ capsid leads to improvement for gene delivery in vivo" BMC Biotechnology vol. 16, p. 1-8 (2016).
Martinez-Navio et al. "Host Anti-antibody Responses Following Adeno-associated Virus-mediated Delivery of Antibodies Against HIV and SIV in Rhesus Monkeys" Molecular Therapy : the journal of the American Society of Gene Therapy, vol. 24, No. 1 p. 76-86 (2016).
McCraw et al. "Structure of adeno-associated virus-2 in complex with neutralizing monoclonal antibody A20" Virology vol. 431, No. 1-2, p. 40-49 (2012).
Meliani et al. "Determination of anti-adeno-associated virus vector neutralizing antibody titer with an in vitro reporter system" Human gene therapy methods vol. 26, p. 45-53 (2015).
Mingozzi et al. "CD8(+) T-cell responses to adeno-associated virus capsid in humans" Nature Medicine vol. 13, No. 4, p. 419-422 (2007).
Mingozzi et al. "Immune responses to AAV vectors: overcoming barriers to successful gene therapy" Blood vol. 122, No. 1 p. 23-36 (2013).

(56) References Cited

OTHER PUBLICATIONS

Mingozzi et al. "Prevalence and pharmacological modulation of humoral immunity to AAV vectors in gene transfer to synovial tissue" Gene Therapy vol. 20, p. 417-424 (2013).
Morrison "$1-million price tag set for Glybera gene therapy" Nature Biotechnology vol. 33, No. 3, p. 217-218 (2015).
Mueller et al. "Human Treg responses allow sustained recombinant adeno-associated virus-mediated transgene expression" The Journal of clinical investigation, vol. 123, No. 12, p. 5310-5318 (2013).
Muzyczka "Use of adeno-associated virus as a general transduction vector for mammalian cells" Current Topics in Microbiology 158 and Immunology vol. 158 p. 98-129 (1992).
Nakai et al. "Unrestricted hepatocyte transduction with adeno-associated virus serotype 8 vectors in mice" Journal of Virology vol. 79, No. 1 p. 214-224 (2005).
Nam et al. "Structural studies of adeno-associated virus serotype 8 capsid transitions associated with endosomal trafficking" Journal of Virology vol. 85, No. 22, p. 11791-11799 (2011).
Namekawa et al. "Two-step imprinted X inactivation: repeat versus genic silencing in the mouse" Mollecular and cellular biology vol. 30, No. 13, p. 3187-3205 (2010).
Nathwani et al. "Adenovirus-associated virus vector-mediated gene transfer in hemophilia B" The New England Journal of Medicine, vol. 365 No. 25, p. 2357-2365 (2011).
Nathwani et al. "Long-term safety and efficacy of factor IX gene therapy in hemophilia B" The New England journal of medicine, vol. 371, p. 1994-2004 (2014).
Nathwani et al. "Safe and efficient transduction of the liver after peripheral vein infusion of self-complementary AAV vector results in stable therapeutic expression of human FIX in nonhuman primates" Blood vol. 109, No. 4 p. 1414-1421 (2007).
Nathwani et al. "Self-complementary adeno-associated virus vectors containing a novel liver-specific human factor IX expression cassette enable highly efficient transduction of murine and nonhuman primate liver" Blood vol. 107, No. 7 p. 2653-2661 (2006).
Nelson et al. "In vivo genome editing improves muscle function in a mouse model of Duchenne muscular dystrophy" Science vol. 351, No. 6271, p. 403-407 (2016).
Nieto et al. "Combined prophylactic and therapeutic intranasal vaccination against human papillomavirus type-16 using different adeno-associated virus serotype vectors" Antiviral Therapy, vol. 14, p. 1125-1137 (2009).
Nieto et al. "Intranasal Vaccination with AAV5 and 9 Vectors Against Human Human Papillomavirus Type 16 in Rhesus Macaques" Human Gene Therapy vol. 23, No. 7 p. 733-741 (2012).
Paneda et al. "Effect of Adeno-Associated Virus Serotype and Genomic Structure on Liver Transduction and Biodistribution in Mice of Both Genders" Human Gene Therapy vol. 20, p. 908-917 (2009).
Ploquin et al. "Protection Against Henipavirus Infection by Use of Recombinant Adeno-Associated Virus-Vector Vaccines" The Journal of infectious diseases vol. 207, p. 469-478 (2013).
Rayaprolu et al. "Comparative analysis of adeno-associated virus capsid stability and dynamics" Journal of Virology vol. 87, No. 24, p. 13150-13160 (2013).
Salganik et al. "Adeno-associated virus capsid proteins may play a role in transcription and second-strand synthesis of recombinant genomes" Journal of Virology vol. 88, No. 2 p. 1071-1079 (2014).

Shelling & Smith "Targeted integration of transfected and infected adeno-associated virus vectors containing the nemycin resistance gene" Gene Therapy vol. 1, No. 3 (1994).
Sipo et al. "Vaccine protection against lethal homologous and heterologous challenge using recombinant AAV vectors expressing codon-optimized genes from pandemic swine origin influenza virus (SOIV)" Vaccine vol. 29, p. 1690-1699 (2011).
Tabebordbar et al. "In vivo gene editing in dystrophic mouse muscle and muscle stem cells" Science vol. 351, No. 6271, p. 407-411 (2016).
Turunen et al. "Sleeping Beauty Transposon Vectors in Liver-directed Gene Delivery of LDLR and VLDLR for Gene Therapy of Familial Hypercholesterolemia" Molecular Therapy: The Journal of the American Society of Gene Therapy vol. 24, No. 3 p. 620-635 (2016).
Uniqure "Press release: uniQure announces first clinical data from second dose cohort of AMT-060 in ongoing phase I/II trial in patients with severe hemophilia B" (2016).
Van Der Marel et al. "Neutralizing antibodies against adeno-associated viruses in inflammatory bowel disease patients: implications for gene therapy" Inflamm Bowel Dis vol. 17, No. 12, p. 2436-2442 (2011).
Vasileva et al. "Precise hit: adeno-associated virus in gene targeting" Nature Reviews—Microbiology, vol. 3, p. 837-847 (2005).
Vercauteren et al. "Superior in vivo Transduction of Human Hepatocytes Using Engineered AAV3 Capsid" Molecular Therapy, vol. 24, No. 6, p. 1042-1049 (2016).
Vincent et al. "Replication and packaging of HIV envelope genes in a novel adeno-associated virus vector system" Vaccine 90 p. 353-359 (1990).
Wang et al. "Comparative Study of Liver Gene Transfer With AAV Vectors Based on Natural and Engineered AAV Capsids" Molecular Therapy: The Journal of the American Society of Gene Therapy vol. 23, No. 12 p. 1877-1887 (2015).
Wilson et al. "Extensive double humanization of both liver and hematopoiesis in FRGN mice" Stem Cell Research vol. 13, p. 404-412 (2014).
Xiao et al. "Gene therapy vectors based on adeno-associated virus type 1" Journal of Virology vol. 73, No. 5 p. 3994-4003 (1999).
Xie et al. "The atomic structure of adeno-associated virus (AAV-2), a vector for human gene therapy" Proceedings of the National Academy of Sciences of the USA vol. 99, No. 16, p. 10405-10410 (2002).
Zhen et al. "Infectious titer assay for adeno-associated virus vectors with sensitivity sufficient to detect single infectious events." Human Gene Therapy vol. 15, p. 709-715 (2004).
Zhou et al "Adeno-Associated Virus 2-mediated High Efficiency Gene Transfer into Immature and Mature Subsets of Hematopoietic Progenitor Cells in Human Umbilical Cord Blood" J. Exp. Med., vol. 179, p. 1867-1875 (1994).
Zhou et al. "Long-term protection against human papillomavirus E7-positive tumor by a single vaccination of adeno-associated virus vectors encoding a fusion protein of inactivated E7 of human papillomavirus 16/18 and heat shock protein 70" Human Gene Therapy vol. 21, p. 109-119 (2010).
Zincarelli et al. "Analysis of AAV serotypes 1-9 mediated gene expression and tropism in mice after systemic injection" Molecular Therapy vol. 16, No. 6 p. 1073-1080 (2008).

* cited by examiner

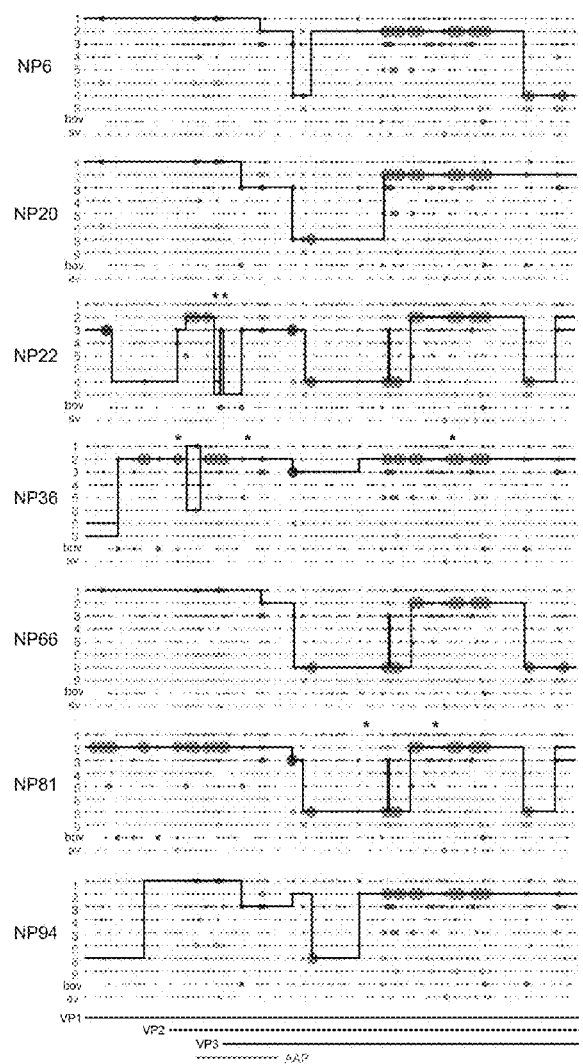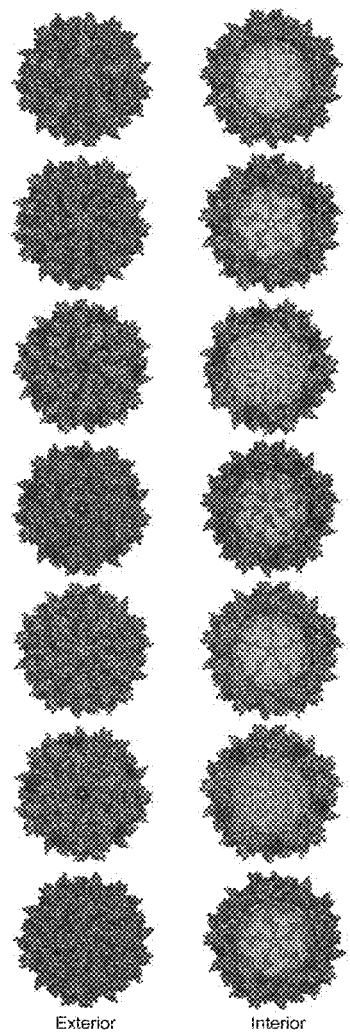
FIG. 3A
FIG. 3B
Exterior    Interior

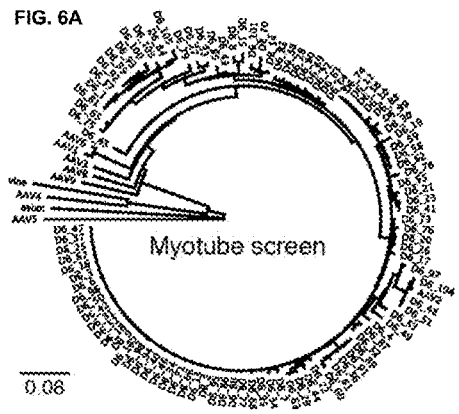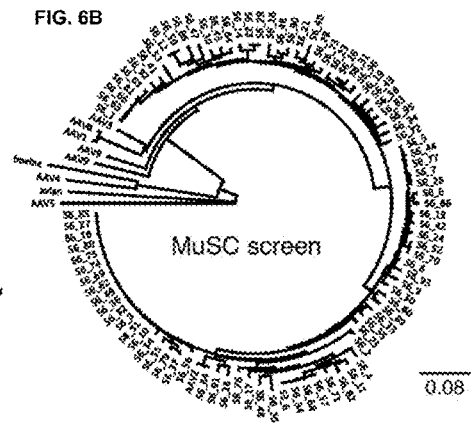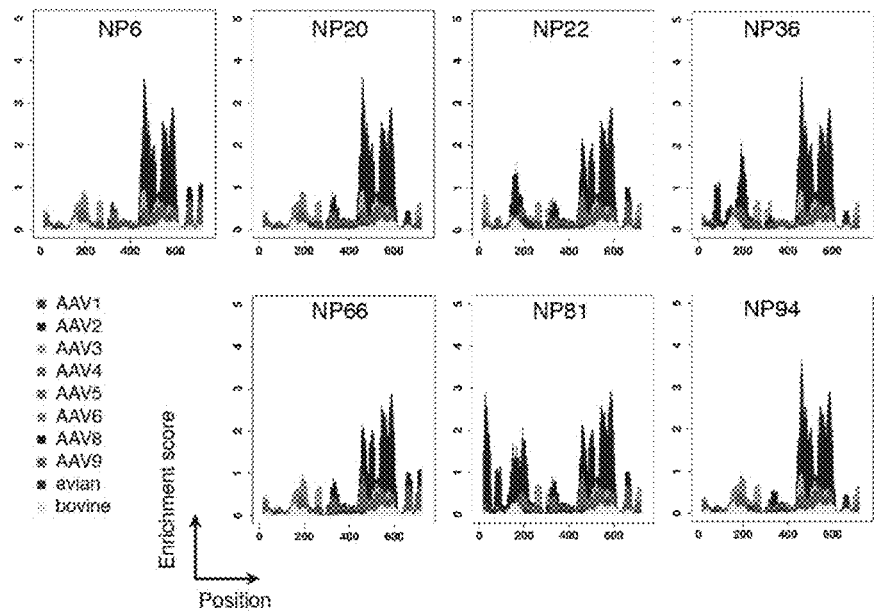

| Round | Raw data CCS reads | CCS reads post-filtering |
|---|---|---|
| Input library | 30,910 | 14,885 |
| R2 MuSC | 6,410 | 4,127 |
| R4 MuSC | 6,345 | 3,557 |
| R6 MuSC | 18,369 | 11,740 |
| R2 Myotube | 14,343 | 8,295 |
| R4 Myotube | 10,645 | 6,955 |
| R6 Myotube | 10,645 | 6,955 |

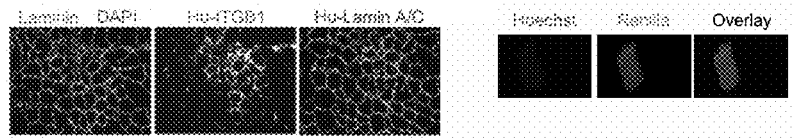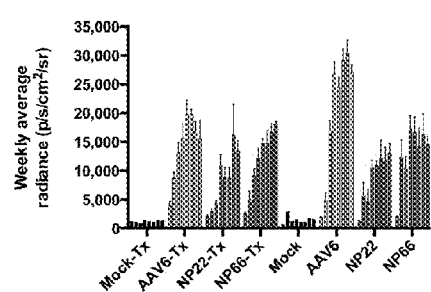

FIG. 10A  >NP22  (SEQ ID NO: 3)

MAADGYLPDWLEDNLSEGIREWWALKPGVPQPKANQQKQDDGRGLVLPGYKYLGPFNGLDKGEPV
NAADAAALEHDKAYDQQLQAGDNPYLRYNHADAEFQERLQEDTSFGGNLGRAVFQAKKRVLEPLGL
VEEAAKTAPGKKRPVEHSPVEPDSSSGTGKAGQQPARKRLNFGQTGDADSVPDPQPIGEPPAAPSGVG
SLTMAAGGGAPMADNNEGADGVGNSSGNWHCDSQWLGDRVITTSTRTWALPTYNNHLYKQISSQSG
ASNDNHYFGYSTPWGYFDFNRFHCHFSPRDWQRLINNNWGFRPKKLSFKLFNIQVKEVTQNDGTKTIA
NNLTSTIQVFTDSEYQLPYVLGSAHQGCLPPFPADVFMIPQYGYLTLNNGSQAVGRSSFYCLEYFPSQM
LRTGNNFQFTYTFEDVPFHSSYAHSQSLDRLMNPLIDQYLYYLSRTQTTGGTTNTQTLGFSQGGPNTM
ANQAKNWLPGPCYRQQRVSKTSADNNNSEYSWTGATKYHLNGRDSLVNPGPAMASHKDDEEKFFPQ
SGVLIFGKQGSEKTNVDIEKVMITDEEEIRTTNPVATEQYGSVSTNLQRGNRQAATADVNTQGVLPGM
VWQDRDVYLQGPIWAKIPHTDGHFHPSPLMGGFGLKHPPPQILIKNTPVPADPPTTFNQSKLNSFITQYS
TGQVSVEIEWELQKENSKRWNPEIQYTSNYNKSVNVDFTVDTNGVYSEPRPIGTRYLTRNL

FIG. 10B  >NP66  (SEQ ID NO: 5)

MAADGYLPDWLEDNLSEGIREWWDLKPGAPKPKANQQKQDDGRGLVLPGYKYLGPFNGLDKGEPV
NAADAAALEHDKAYDQQLKAGDNPYLRYNHADAEFQERLQEDTSFGGNLGRAVFQAKKRVLEPLGL
VEEGAKTAPGKKRPVEQSPQEPDSSSGIGKTGQQPAKKRLNFGQTGDSESVPDPQPLGEPPATPAAVGP
TTMASGGGAPMADNNEGADGVGNASGNWHCDSTWLGDRVITTSTRTWALPTYNNHLYKQISSQSGA
SNDNHYFGYSTPWGYFDFNRFHCHFSPRDWQRLINNNWGFRPKRLSFKLFNIQVKEVTQNEGTKTIAN
NLTSTIQVFTDSEYQLPYVLGSAHQGCLPPFPADVFMIPQYGYLTLNNGSQAVGRSSFYCLEYFPSQML
RTGNNFQFTYTFEDVPFHSSYAHSQSLDRLMNPLIDQYLYYLSRTQTTGGTTNTQTLGFSQGGPNTMA
NQAKNWLPGPCYRQQRVSKTSADNNNSEYSWTGATKYHLNGRDSLVNPGPAMASHKDDEEKFFPQS
GVLIFGKQGSEKTNVDIEKVMITDEEEIRTTNPVATEQYGSVSTNLQRGNRQAATADVNTQGVLPGMV
WQDRDVYLQGPIWAKIPHTDGHFHPSPLMGGFGLKHPPPQILIKNTPVPADPPTTFNQSKLNSFITQYST
GQVSVEIEWELQKENSKRWNPEIQYTSNYYKSTSVDFAVNTEGVYSEPRPIGTRYLTRNL

FIG. 10C  >NP94  (SEQ ID NO: 7)

MAADGYLPDWLEDNLSEGIREWWALKPGAPKPKANQQKQDDGRGLVLPGYKYLGPFNGLDKGEPV
NAADAAALEHDKAYDQQLKAGDNPYLRYNHADAEFQERLQEDTSFGGNLGRAVFQAKKRVLEPLGL
VEEGAKTAPGKKRPVEQSPQEPDSSSGIGKTGQQPAKKRLNFGQTGDSESVPDPQPLGEPPATPAAVGP
TTMASGGGAPMADNNEGADGVGNASGNWHCDSQWLGDRVITTSTRTWALPTYNNHLYKQISSQSGA
SNDNHYFGYSTPWGYFDFNRFHCHFSPRDWQRLINNNWGFRPKRLNFKLFNIQVKEVTQNDGTTTIAN
NLTSTIQVFTDSEYQLPYVLGSAHQGCLPPFPADVFMIPQYGYLTLNNGSQAVGRSSFYCLEYFPSQML
RTGNNFTFSYTFEDVPFHSSYAHSQSLDRLMNPLIDQYLYYLSRTNTPSGTTTQSRLQFSQAGASDIRD
QSRNWLPGPCYRQQRVSKTSADNNNSEYSWTGATKYHLNGRDSLVNPGPAMASHKDDEEKFFPQSG
VLIFGKQGSEKTNVDIEKVMITDEEEIRTTNPVATEQYGSVSTNLQRGNRQAATADVNTQGVLPGMV
WQDRDVYLQGPIWAKIPHTDGHFHPSPLMGGFGLKHPPPQILIKNTPVPANPSTTFSAAKFASFITQYST
GQVSVEIEWELQKENSKRWNPEIQYTSNYNKSVNVDFTVDTNGVYSEPRPIGTRYLTRNL

FIG. 11

| DOS | Age | Gender | Ethnicity | Smoke | ABO | DOS | Age | Gender | Ethnicity | Smoke | ABO |
|---|---|---|---|---|---|---|---|---|---|---|---|
| 1/29/16 | 34 | Male | Black | Yes | B+ | 1/29/16 | 55 | Male | Black | Yes | A+ |
| 2/8/16 | 23 | Female | Caucasian | Yes | O+ | 1/29/16 | 22 | Male | Black | Yes | O+ |
| 2/8/16 | 37 | Female | Black | No | A+ | 1/29/16 | 52 | Male | Black | Yes | B+ |
| 2/8/16 | 21 | Female | Black | No | O+ | 1/29/16 | 22 | Male | Black | No | A+ |
| 2/8/16 | 37 | Female | Caucasian | Yes | A- | 1/29/16 | 24 | Male | Black | Yes | A+ |
| 2/8/16 | 24 | Female | Caucasian | No | A- | 2/5/16 | 18 | Female | Black | Yes | A+ |
| 1/29/16 | 21 | Male | Black | No | O+ | 1/29/16 | 40 | Male | Black | No | B+ |
| 1/29/16 | 23 | Male | Black | Yes | O+ | 1/29/16 | 33 | Male | Black | Yes | A+ |
| 1/29/16 | 25 | Female | Black | Yes | O+ | 1/12/16 | 42 | Male | Black | No | B+ |
| 1/29/16 | 25 | Male | Black | Yes | O+ | 1/29/16 | 22 | Male | Black | No | O+ |
| 2/5/16 | 27 | Female | Black | No | A+ | 1/29/16 | 22 | Female | Black | No | A+ |
| 1/29/16 | 21 | Male | Black | Yes | B+ | 1/29/16 | 41 | Male | Caucasian | Yes | A- |
| 2/8/16 | 21 | Female | Black | Yes | O+ | 1/29/16 | 23 | Male | Black | Yes | O+ |
| 1/29/16 | 20 | Male | Black | Yes | O+ | 1/12/16 | 39 | Male | Caucasian | Yes | A- |
| 1/12/16 | 31 | Male | Black | Yes | A+ | 1/29/16 | 18 | Male | Black | No | O+ |
| 1/29/16 | 29 | Male | Black | No | B+ | 1/29/16 | 19 | Male | Black | Yes | O+ |
| 1/29/16 | 42 | Male | Black | Yes | A+ | 1/29/16 | 23 | Female | Black | No | O+ |
| 1/29/16 | 20 | Male | Black | Yes | O+ | 1/29/16 | 18 | Female | Black | No | A+ |
| 1/29/16 | 39 | Female | Black | Yes | B+ | 1/29/16 | 42 | Male | Black | Yes | A+ |
| 1/29/16 | 30 | Male | Black | Yes | B+ | 1/29/16 | 24 | Male | Black | Yes | O+ |
| 1/29/16 | 22 | Male | Black | Yes | A+ | 1/29/16 | 53 | Male | Black | Yes | A+ |
| 1/29/16 | 35 | Male | Black | Yes | A+ | 1/12/16 | 24 | Male | Black | No | B+ |
| 1/29/16 | 24 | Male | Black | No | A+ | 1/29/16 | 59 | Female | Black | Yes | B+ |
| 2/5/16 | 18 | Female | Caucasian | No | O+ | 1/29/16 | 22 | Female | Black | Yes | O+ |
| 2/5/16 | 36 | Female | Black | No | B+ | 1/29/16 | 43 | Male | Black | No | A+ |

RECOMBINANT ADENO-ASSOCIATED VIRUS CAPSIDS WITH ENHANCED HUMAN SKELETAL MUSCLE TROPISM

CROSS REFERENCE TO RELATED APPLICATIONS

This application claims the benefit of U.S. Provisional Application No. 62/262,289, filed Dec. 2, 2015, U.S. Provisional Application No. 62/268,428, filed Dec. 16, 2015, and U.S. Provisional Application No. 62/336,078, filed on May 13, 2016, all of which are expressly incorporated herein by reference in their entireties.

STATEMENT AS TO RIGHTS TO INVENTIONS MADE UNDER FEDERALLY SPONSORED RESEARCH OR DEVELOPMENT

This invention was made with Government support under contracts AI116698 and HL119059 awarded by the National Institutes of Health. The U.S. Government has certain rights in the invention.

FIELD OF THE INVENTION

The present invention relates to variant AAV capsid polypeptides, wherein the variant AAV capsid polypeptides exhibit increased transduction and/or tropism in human skeletal muscle tissue or cells as compared to non-variant parent capsid polypeptides.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Feb. 4, 2017, entitles 068597_5032_US_ST25.txt which is 68 kilobytes in size.

BACKGROUND OF THE INVENTION

Genetic disorders caused by absence of or a defect in a desirable gene (loss of function) or expression of an undesirable or defective gene (gain of function) lead to a variety of diseases. At present, adeno-associated virus (AAV) vectors are recognized as the gene transfer vectors of choice for therapeutic applications since they have the best safety and efficacy profile for the delivery of genes in vivo. Of the AAV serotypes isolated so far, AAV2 and AAV8 have been used to target the liver of humans affected by severe hemophilia B. Both vectors worked efficiently and, in the case of AAV8, long-term expression of the therapeutic transgene was documented. Recent data from humans showed that targeting the liver with an AAV vector achieves long-term expression of the FIX transgene at therapeutic levels. Additionally, several Phase 1 and Phase 2 clinical trials using AAV serotypes 1, 2 and chimeric 2.5 have been reported for the treatment of Duchenne muscular dystrophy (DMD) and alpha-1 antitrypsin deficiency (D. E. Bowles, S. W J McPhee, C. Li, S. J. Gray, J. J. Samulski, A. S. Camp, J. Li, B. Wang, P. E. Monahan, J. E. Rabinowitz, J. C. Grieger, La. Govindasamy, M. Agbandje-McKenna, X Xiao and R. J. Samulski, *Molecular Therapy*, 20, 443-455 (2012); M. L. Brantly, J. D. Chulay, L. Wang, C. Mueller, M. Humphries, L. T. Spencer, F. Rouhani, T. J. Conlon, R. Calcedo, M. R. Betts, C. Spencer, B. J. Byrne, J. M. Wilson, T. R. Flotte, Sustained transgene expression despite T lymphocyte responses in a clinical trial of rAAV1-AAT gene therapy. *Proceedings of the National Academy of Sciences of the United States of America* 106, 16363-16368 (2009); T. R. Flotte, M. L. Brantly, L. T. Spencer, B. J. Byrne, C. T. Spencer, D. J. Baker, M. Humphries, Phase I trial of intramuscular injection of a recombinant adeno-associated virus alpha 1-antitrypsin (rAAV2-CB-hAAT) gene vector to AAT-deficient adults. *Human gene therapy* 15, 93-128 (2004); T. R. Flotte, B. C. Trapnell, M. Humphries, B. Carey, R. Calcedo, F. Rouhani, M. Campbell-Thompson, A. T. Yachnis, R. A. Sandhaus, N. G. McElvaney, C. Mueller, L. M. Messina, J. M. Wilson, M. Brantly, D. R. Knop, G. J. Ye, J. D. Chulay, Phase 2 clinical trial of a recombinant adeno-associated viral vector expressing alpha1-antitrypsin: interim results. *Human gene therapy* 22, 1239-1247 (2011); C. Mueller, J. D. Chulay, B. C. Trapnell, M. Humphries, B. Carey, R. A. Sandhaus, N. G. McElvaney, L. Messina, Q. Tang, F. N. Rouhani, M. Campbell-Thompson, A. D. Fu, A. Yachnis, D. R. Knop, G. J. Ye, M. Brantly, R. Calcedo, S. Somanathan, L. P. Richman, R. H. Vonderheide, M. A. Hulme, T. M. Brusko, J. M. Wilson, T. R. Flotte, Human Treg responses allow sustained recombinant adeno-associated virus-mediated transgene expression. *The Journal of clinical investigation* 123, 5310-5318 (2013)).

Adeno-associated virus (AAV), a member of the Parvovirus family, is a small nonenveloped, icosahedral virus with single-stranded linear DNA genomes of 4.7 kilobases (kb). AAV is assigned to the genus, Dependovirus, because the virus was discovered as a contaminant in purified adenovirus stocks (D. M. Knipe, P. M. Howley, *Field's Virology*, Lippincott Williams & Wilkins, Philadelphia, ed. Sixth, 2013). In its wild-type state, AAV depends on a helper virus—typically adenovirus—to provide necessary protein factors for replication, as AAV is naturally replication-defective. The 4.7-kb genome of AAV is flanked by two inverted terminal repeats (ITRs) that fold into a hairpin shape important for replication. Being naturally replication-defective and capable of transducing nearly every cell type in the human body, AAV represents an ideal vector for therapeutic use in gene therapy or vaccine delivery. In it's wild-type state, AAV's life cycle includes a latent phase during which AAV genomes, after infection, are site-specifically integrated into host chromosomes and an infectious phase during which, following either adenovirus or herpes simplex virus infection, the integrated genomes are subsequently rescued, replicated, and packaged into infectious viruses. When vectorized, the viral Rep and Cap genes of AAV are removed and provided in trans during virus production, making the ITRs the only viral DNA that remains (A. Vasileva, R. Jessberger, *Nature reviews. Microbiology*, 3, 837-847 (2005)). Rep and Cap are then replaced with an array of possible transfer vector configurations to perform gene addition or gene targeting. These vectorized recombinant AAVs (rAAV) transduce both dividing and non-dividing cells, and show robust stable expression in quiescent tissues like skeletal muscle. The number of rAAV gene therapy clinical trials that have been completed or are ongoing to treat various inherited or acquired diseases is increasing dramatically as rAAV-based therapies increase in popularity. Similarly, in the clinical vaccine space, there have been numerous recent preclinical studies and one ongoing clinical trial using rAAV as a vector to deliver antibody expression cassettes in passive vaccine approaches for human/simian immunodeficiency virus (HIV/SIV), influenza virus, henipavirus, and human papilloma virus (HPV). (See, P. R. Johnson, B. C. Schnepp, J. Zhang, M. J. Connell, S. M. Greene, E. Yuste, R. C. Desrosiers, K. R. Clark, *Nature medicine* 15, 901-906 (2009); A. B. Balazs, J. Chen, C. M. Hong, D. S. Rao, L. Yang, D. Baltimore, *Nature* 481, 81-84 (2012); A. B. Balazs, Y. Ouyang, C. M. Hong, J. Chen, S. M. Nguyen, D. S. Rao, D. S. An, D. Baltimore, *Nature medicine* 20, 296-300 (2014); A. B. Balazs, J. D. Bloom, C. M. Hong, D. S. Rao, D. Baltimore, *Nature biotechnology* 31, 647-652 (2013); M. P. Limberis, V. S. Adam, G. Wong, J. Gren, D. Kobasa, T. M. Ross, G. P. Kobinger, A. Tretiakova, J. M., *Science translational medicine* 5, 187ra172 (2013); M. P. Limberis, T. Racine, D. Kobasa, Y. Li, G. F. Gao, G. Kobinger, J. M. Wilson, Vectored expression of the broadly neutralizing antibody FI6 in mouse airway provides partial protection against a new avian influenza A virus, H7N9. *Clinical and vaccine immunology*: CVI 20, 1836-1837 (2013); J. Lin, R. Calcedo, L. H. Vandenberghe, P. Bell, S. Somanathan, J. M. Wilson, *Journal of virology* 83, 12738-12750 (2009); I. Sipo, M. Knauf, H. Fechner, W. Poller, O. Planz, R. Kurth, S. Norley, *Vaccine* 29, 1690-1699 (2011); A. Ploquin, J. Szecsi, C. Mathieu, V. Guillaume, V. Barateau, K. C. Ong, K. T. Wong, F. L. Cosset, B. Horvat, A. Salvetti, *The Journal of infectious diseases* 207, 469-478 (2013); D. Kuck, T. Lau, B. Leuchs, A. Kern, M. Muller, L. Gissmann, J. A. Kleinschmidt, *Journal of virology* 80, 2621-2630 (2006); K. Nieto, A. Kern, B. Leuchs, L. Gissmann, M. Muller, J. A. Kleinschmidt, *Antiviral therapy* 14, 1125-1137 (2009); K. Nieto, C. Stahl-Hennig, B. Leuchs, M. Muller, L. Gissmann, J. A. Kleinschmidt, *Human gene therapy* 23, 733-741 (2012); and L. Zhou, T. Zhu, X. Ye, L. Yang, B. Wang, X. Liang, L. Lu, Y. P. Tsao, S. L. Chen, J. Li, X. Xiao, *Human gene therapy* 21, 109-119 (2010).) The properties of non-pathogenicity, broad host range of infectivity, including non-dividing cells, and potential site-specific chromosomal integration make AAV an attractive tool for gene transfer.

The first rAAV-based gene therapy to be approved in the Western world (Glybera® for lipoprotein lipase deficiency, approved for use in 2012 in the European Union) has stimulated the gene therapy community, investors and regulators to the real possibility of moving rAAV therapies into the clinic globally. Yet, despite the impressive abilities of rAAV to transduce a variety of tissue and cell types, skeletal muscle has been historically been one of the most challenging tissues to transduce at high levels sufficient to provide therapeutic levels of expression of delivered transgene products. Indeed, the current best skeletal muscle tropic serotypes (rAAV 1, 2, 6 and 8) have seen limited success clinically for intramuscular delivery of transgene products in gene therapy trials for skeletal muscle disorders. This likely stems from the fact that preclinical modeling with rAAV to determine the best capsid serotypes for transducing target tissues is done in animal models—typically mice—which do not necessarily recapitulate the tissue and cell tropism each rAAV has in humans, nor the transduction capabilities at treatment.

The recent excitement surrounding the possible use of rAAV as a vector for delivery of vaccines providing passive immunoprotection against pathogenic viruses like HIV and influenza virus in particular, has renewed the urgency for rAAV capsids capable of highly efficient intramuscular delivery for this unique vaccination approach in humans. Given the limitations with efficient human skeletal muscle transduction with existing rAAV serotypes, we sought to bioengineer a clinical rAAV vector candidate that can efficiently transduce human skeletal muscle at a level sufficient to express therapeutic levels of broad-spectrum antibodies for vaccine strategies or genes essential for muscle disorder treatment.

A variety of published US applications describe AAV vectors and virions, including U.S. Publication Nos. 2015/0176027, 2015/0023924, 2014/0348794, 2014/0242031, and 2012/0164106; all of which are incorporated by reference herein in their entireties.

However, high levels of transduction are needed for muscle gene therapy trials as there are physical limitations to how much AAV can be delivered in a single intramuscular injection which is further complicated by the fact that injections need to span the length of the muscle to correct defects along the muscle length. If an AAV had superior human skeletal muscle transduction, a lower dose and fewer injections would be needed to achieve therapeutic relevance. Similarly for use as a vaccine delivery tool, high efficiency transduction and stability is needed to achieve robust secretion of antibodies encoded within the AAV to reach therapeutic levels of circulating antibodies in the blood.

There remains, therefore, a need in the art for AAV vectors with improved human skeletal muscle transduction. The present invention meets this need by providing variant AAV capsid polypeptides that demonstrate significantly improved human skeletal muscle transduction over existing capsid serotypes in humanized muscle mice in vivo, in numerous human muscle cell cultures in vitro, and most importantly in human skeletal muscle explants ex vivo. The present invention utilizes directed evolution by DNA gene shuffling to characterize and screen for such variant AAV capsid polypeptides that have high efficiency skeletal muscle transduction for human skeletal muscle specifically.

BRIEF SUMMARY OF THE INVENTION

The present invention provides variant adeno-associated virus (AAV) capsid polypeptides. The variant AAV capsid polypeptides exhibit increased transduction or tropism in human skeletal muscle tissue or cells as compared to non-variant parent capsid polypeptides.

In some embodiments, the variant AAV capsid polypeptides exhibit increased transduction or tropism in human muscle tissue or cells as compared to non-variant parent capsid polypeptides.

In some embodiments, the variant AAV capsid polypeptides exhibit increased transduction as compared to non-variant parent capsid polypeptides.

In some embodiments, the variant AAV capsid polypeptides exhibit increased tropism as compared to non-variant parent capsid polypeptides.

In some embodiments, the variant AAV capsid polypeptides further exhibit an enhanced neutralization profile as compared to non-variant parent capsid polypeptides. In some embodiments, the variant AAV capsid polypeptides exhibit an enhanced neutralization profile against pooled human immunoglobulins as compared to non-variant parent capsid polypeptides.

In some embodiments, the variant AAV capsid polypeptides further exhibit increased transduction or tropism in one or more non-muscle human tissues as compared to non-variant parent capsid polypeptides.

In some embodiments, the variant AAV capsid polypeptides exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells.

In some embodiments, the variant AAV capsid polypeptides exhibit increased transduction of human muscle tissue or cells in vivo as compared to non-variant parent capsid polypeptides.

In some embodiments, the variant AAV capsid polypeptides exhibit increased transduction of human muscle tissue or cells in vitro as compared to non-variant parent capsid polypeptides.

In some embodiments, the variant AAV capsid polypeptides exhibit increased transduction of a human muscle tissue explant ex vivo as compared to non-variant parent capsid polypeptides.

In some embodiments, the variant AAV capsid polypeptides are part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a gene targeting sequence, and a therapeutic expression cassette.

In some embodiments, the nucleic acid sequence is contained within an AAV vector.

In some embodiments, the nucleic acid sequence is a genomic targeting cassette.

In some embodiments, the expression cassette is a CRISPR/CAS expression system.

In some embodiments, therapeutic expression cassette encodes a therapeutic protein or antibody.

In some embodiments, the variant AAV capsid polypeptide sequence is selected from the group consisting of AAV-NP6 (SEQ ID NO: 1), AAV-NP20 (SEQ ID NO: 2), AAV-NP22, (SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7).

The present invention provides methods of using the variant AAV capsid polypeptides of the present invention in a therapeutic treatment regimen, vaccine, or research tool development manner.

The present invention also provides methods of using the variant AAV capsid polypeptides of the invention to reduce the amount of total nucleic acid administered to a subject. The method comprises administering less total nucleic acid amount to said subject when said nucleic acid is transduced using a variant AAV capsid polypeptide as compared to the amount of nucleic acid administered to said subject when said nucleic acid is transduced using a non-variant parent capsid polypeptide in order to obtain a similar therapeutic effect.

The present invention provides an AAV vector comprising a nucleic acid sequence encoding a variant AAV capsid polypeptide. The variant AAV capsid polypeptide exhibits increased transduction or tropism in human muscle tissue or cells as compared to a non-variant parent capsid polypeptide. The variant AAV capsid polypeptide is capable of exhibiting increased transduction or tropism in human muscle cells and tissue.

In some embodiments, the AAV vector comprises a nucleic acid sequence encoding a variant AAV capsid polypeptide, wherein said variant AAV capsid polypeptide exhibits increased transduction or tropism in human muscle tissue or cells as compared to a non-variant parent capsid polypeptide.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid.

In some embodiments, the variant AAV capsid polypeptide further exhibits an enhanced neutralization profile as compared to a non-variant parent capsid polypeptide. In some embodiments, the variant AAV capsid polypeptide of the invention further exhibits an enhanced neutralization profile against pooled human immunoglobulins as compared to a non-variant parent capsid polypeptide.

In some embodiments, the variant AAV capsid polypeptide further exhibits increased transduction or tropism in one or more non-muscle human tissues as compared to a non-variant parent capsid polypeptide.

In some embodiments, the variant AAV capsid polypeptide exhibits increased transduction of human muscle tissue or cells in vivo as compared to a non-variant parent capsid polypeptide.

In some embodiments, the variant AAV capsid polypeptide exhibits increased transduction of human muscle tissue or cells in vitro as compared to a non-variant parent capsid polypeptide.

In some embodiments, the variant AAV capsid polypeptide exhibits increased transduction of a human muscle tissue explant ex vivo as compared to a non-variant parent capsid polypeptide.

In some embodiments, the variant AAV capsid polypeptide is part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a sequence for gene targeting, and a therapeutic expression cassette.

In some embodiments, the variant AAV capsid polypeptide results in increased nucleic acid expression as compared to a non-variant parent capsid polypeptide.

In some embodiments, the nucleic acid sequence is a genomic targeting cassette.

In some embodiments, the expression cassette is a CRISPR/CAS expression system.

In some embodiments, the therapeutic expression cassette encodes a therapeutic protein or vaccine.

In some embodiments, the variant AAV capsid polypeptide sequence is selected from the group consisting of AAV-NP6 (SEQ ID NO: 1), AAV-NP20 (SEQ ID NO: 2), AAV-NP22, (SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7). The present invention further provides methods of using the variant AAV capsid polypeptide of the invention in a therapeutic treatment regimen or vaccine.

The present invention further provides methods of using the AAV vectors of the invention to reduce the amount of total AAV administered to a subject, where the method comprises administering less total AAV vector amount to the subject when the AAV vector is transduced using a variant AAV capsid polypeptide as compared to the amount of AAV vector administered to said subject when said AAV vector is transduced using a non-variant parent capsid polypeptide in order to obtain a similar therapeutic effect.

In some embodiments, the present invention provides a method for generating an AAV vector encoding a variant AAV capsid polypeptide, wherein said variant AAV capsid polypeptide exhibits increased transduction or tropism in human muscle tissue or cells as compared to a non-variant parent capsid polypeptide, said method comprising:

a) generating a library of variant AAV capsid polypeptide genes, wherein said variant AAV capsid polypeptide genes include a plurality of variant AAV capsid polypeptide genes comprising sequences from more than one non-variant parent capsid polypeptide;

b) generating an AAV vector library by cloning said variant AAV capsid polypeptide gene library into AAV vectors, wherein said AAV vectors are replication competent;

c) screening said replication competent AAV vectors from b) encoding for variant AAV capsid polypeptides for increased transduction or tropism in human muscle tissue or cells as compared to a vector encoding a non-variant parent capsid polypeptide; and d) selecting said AAV vectors from c).

In some embodiments, the method further comprises e) determining the sequence of said variant AAV capsid polypeptides encoded by the AAV vectors from d).

In some embodiments, the variant AAV capsid polypeptides exhibit increased transduction as compared to non-variant parent capsid polypeptides.

In some embodiments, the variant AAV capsid polypeptides exhibit increased tropism as compared to non-variant parent capsid polypeptides.

In some embodiments, the variant AAV capsid polypeptides further exhibit an enhanced neutralization profile as compared to non-variant parent capsid polypeptides. In some embodiments, the variant AAV capsid polypeptides of the invention further exhibits an enhanced neutralization profile against pooled human immunoglobulins as compared to non-variant parent capsid polypeptides.

In some embodiments, the variant AAV capsid polypeptides further exhibit increased transduction or tropism in one or more non-muscle human tissues as compared to non-variant parent capsid polypeptides.

In some embodiments, the variant AAV capsid polypeptides exhibit increased transduction of human muscle tissue or cells in vivo as compared to non-variant parent capsid polypeptides.

In some embodiments, the variant AAV capsid polypeptides exhibit increased transduction of human muscle tissue or cells in vitro as compared to non-variant parent capsid polypeptides.

In some embodiments, the variant AAV capsid polypeptides exhibit increased transduction of a human muscle tissue explant ex vivo as compared to non-variant parent capsid polypeptides.

Other objects, advantages and embodiments of the invention will be apparent from the detailed description following.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A-FIG. 3B provides sequence and structural composition of selected shuffled AAV capsid variants. (A) Crossover mapping analysis of parental capsid fragment crossovers in vectorized shuffled capsids. Large dots are a 100% match for only one parent (each parent colored differently) and small dots represent that more than one parent matches at that position. The solid black line for each chimera represents the parental serotype match identified across each crossover. Thin parallel lines between crossovers indicate multiple parental matches at an equal probability. Vertical spikes indicate a mutation from within the parental sequence space, while an overhead asterisk indicates an evolved de novo mutation for which no parent has that amino acid at that position. VP1, VP2, VP3 and AAP ORFs are shown below. (B) Shuffled variants were 3D false-color mapped onto the crystal structure of AAV8. Color-coding indicates parental contribution using colors as in (A).

FIG. 6A-FIG. 6C shows phylogeny and enrichment scores of top capsid variants from completion of each screen. (A) Phylogenetic tree showing genetic relatedness at the amino acid level among the parental serotypes in the library and the top 100 selected variants from round six of the screen in differentiated human myotubes pooled from five patients. (B) Phylogenetic tree showing genetic relatedness at the amino acid level among the parental serotypes in the library and the top 100 selected variants from round six of the screen in primary human skeletal muscle stem cells pooled from five patients. (C) Enrichment scores were calculated for each amino acid position in the sequence of each chimera by comparison of sequences from parental serotypes based on maximum likelihood. Library parents are depicted in different colors as shown.

FIG. 9A-FIG. 9E provides ex vivo and in vivo data support superior transduction with NP22 and NP66. (A) Weekly FLuc time course in non-transplanted (non-Tx) and transplanted (Tx) NSG mice treated with PBS, rAAV6, NP22 or NP66 expressing ssAAV-EF1α-GFP-P2A-FLuc after IM administration (1E9 vg/leg). Mean radiance (p/s/cm$^2$/sr) is shown with all mice imaged on the same shared scale. (B) Human engraftment confirmation in Tx'd NSG mice from (A). Laminin (green), human-ITGB1 (gray), DAPI (blue), and human nuclear lamin A/C (red) on t. anterior cross-sections. Scale=100-µM. (C) Weekly mean radiance+/−SD per mouse from (A). (D) Representative staining of transduced single human l. dorsi muscle fibers for RLuc (green) and Hoechst (blue) from patient-4 demonstrating viral uptake along entire fiber length. (E) H&E stains of rhesus b. femoris muscle demonstrating normal muscle architecture at the time of harvest.

FIG. 10A-FIG. 10C provides amino acid sequences of best performing shuffled capsid variants. (A) AAV-NP22. (B) AAV-NP66. (C) AAV-NP94.

FIG. 11 provides details for normal off-clot human serum samples. Details on 50 US serum donors including date of sample blood draw (DOS), age at time of donation, gender, ethnicity, smoker status and ABO blood type. All donors were negative for HBV, HCV and HIV (data not shown).

DETAILED DESCRIPTION OF THE INVENTION

Introduction

Figure 1:
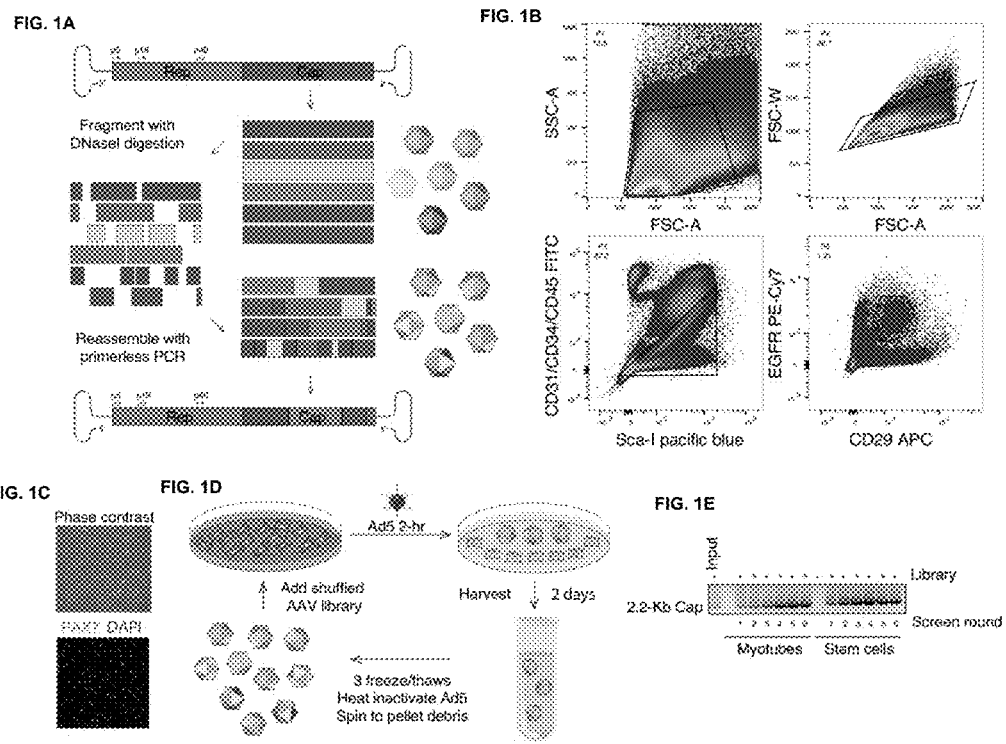
FIG. 1A-FIG. 1E shows directed evolution of AAV capsids by DNA shuffling and selection screening on primary human skeletal muscle stem cells and myotubes. (A) AAV capsid genes from ten parental serotypes (1, 2, 3b, 4, 5, 6, 8, 9_hu14, avian and bovine) were PCR-amplified, fragmented with DNaseI digestion and randomly reassembled through self-priming PCR. Resultant shuffled Cap genes were cloned back into a wild-type AAV production plasmid downstream of AAV2 ITRs and Rep. The AAV library was packaged using standard production protocols, titered and used for selection. (B) Sequential gating scheme (P1 to P4) to isolate $CD31^-CD34^-CD45^-ITGB1^+EGFR^+$ primary human skeletal muscle stem cells from surgical specimens. Numbers indicate percentage of total events falling within each gate. (C) Phase contrast and immunofluorescence PAX7 (pink) and DAPI (blue) nuclear staining of purified primary human muscle stem cell cultures. Scale=100 µm. (D) Diagram illustrating the two selection screens with replicating AAV capsid libraries from (A) that were performed on both pooled primary human skeletal muscle stem cells and human myotubes. (E) Semi-quantitative AAV Cap PCR (2.2-Kb product) was performed at each round of each selection screen to demonstrate active replication of AAV library genomes throughout each round of the screen.

There remains a need in the art for gene therapy vectors capable of increased transduction in human skeletal muscle for gene therapy, so that more therapeutic levels of nucleic acid expression can be achieved. The present invention meets this need and provides variant AAV capsid polypeptides that exhibit increased transduction and/or tropism in human muscle tissue or cells as compared to non-variant parent capsid polypeptides.

Detailed Description

In various embodiments, the present invention provides variant adeno-associated virus (AAV) capsid polypeptides, wherein the variant AAV capsid polypeptides exhibit increased transduction or tropism in human muscle tissue or cells as compared to non-variant parent capsid polypeptides. In some embodiments the variant AAV capsid polypeptide is referred to as a recombinant variant AAV capsid polypeptide or variant rAAV capsid polypeptide.

In other various embodiments, the present invention provides AAV vectors comprising a nucleic acid sequence coding for a variant AAV capsid polypeptide, wherein the variant AAV capsid polypeptide exhibits increased transduction or tropism in human muscle tissue or cells as compared to a vector encoding a non-variant parent capsid polypeptide. In some embodiments the AAV vector is referred to as a recombinant AAV or rAAV vector.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism in human muscle tissue or cells as compared to a vector encoding a non-variant parent capsid polypeptide. In some embodiments, the variant AAV capsid polypeptide does not comprise an amino acid sequence present in a naturally occurring AAV capsid polypeptide.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism in human muscle tissue or cells as compared to a vector encoding a non-variant parent capsid polypeptide. In some embodiments, the AAV capsid polypeptide does not comprise an amino acid sequence present in a naturally occurring AAV capsid polypeptide.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

As described in the present invention, the following terms will be employed, and are defined as indicated below.

Abbreviations

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

Definitions

The term "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

An "AAV vector" as used herein refers to an AAV vector nucleic acid sequence encoding for various nucleic acid sequences, including in some embodiments a variant capsid polypeptide (i.e., the AAV vector comprises a nucleic acid sequence encoding for a variant capsid polypeptide, also referred to as a variant AAV capsid polypeptide), wherein the variant AAV capsid polypeptides exhibit increased transduction or tropism in human muscle tissue or cells as compared to non-variant parent capsid polypeptides. The AAV vectors can also comprise a heterologous nucleic acid sequence not of AAV origin as part of the nucleic acid insert. This heterologous nucleic acid sequence typically comprises a sequence of interest for the genetic transformation of a cell. In general, the heterologous nucleic acid sequence is flanked by at least one, and generally by two AAV inverted terminal repeat sequences (ITRs).

The phrase "non-variant parent capsid polypeptides" includes any naturally occurring AAV capsid polypeptides and/or any AAV wild-type capsid polypeptides. In some embodiments, the non-variant parent capsid polypeptides include AAV1, AAV2, AAV3, AAV4, AAV5, AAV6, AAV7, AAV8, AAV9, bovine AAV and/or avian AAV capsid polypeptides.

The term "substantially identical" in the context of variant AAV capsid polypeptides and non-variant parent capsid polypeptides refers to sequences with 1 or more amino acid changes. In some embodiments, these changes do not affect the packaging function of the capsid polypeptides. In some embodiments, substantially identical include variant AAV capsid polypeptides about 99%, about 98%, about 97%, about 96%, about 95%, about 94%, about 93%, about 92%, about 91%, or about 90% identical to non-variant parent capsid polypeptides. In some embodiments, the variant AAV capsid polypeptides can be substantially identical to non-variant parent capsid polypeptides over a subregion of the variant AAV capsid polypeptide, such as over about 25%, about 50%, about 75%, or about 90% of the total polypeptide sequence length.

An "AAV virion" or "AAV virus" or "AAV viral particle" or "AAV vector particle" refers to a viral particle composed of at least one AAV capsid polypeptide (including both variant AAV capsid polypeptides and non-variant parent capsid polypeptides) and an encapsidated polynucleotide AAV transfer vector. If the particle comprises a heterologous nucleic acid (i.e. a polynucleotide other than a wild-type AAV genome, such as a transgene to be delivered to a mammalian cell), it can be referred to as an "AAV vector particle" or simply an "AAV vector". Thus, production of AAV virion or AAV particle necessarily includes production of AAV vector as such a vector is contained within an AAV virion or AAV particle.

"Packaging" refers to a series of intracellular events resulting in the assembly of AAV virions or AAV particles which encapsidate a nucleic acid sequence and/or other therapeutic molecule. Packaging can refer to encapsidation of nucleic acid sequence and/or other therapeutic molecules into a capsid comprising the variant AAV capsid polypeptides described herein.

The phrase "therapeutic molecule" as used herein can include nucleic acids (including, for example, vectors), polypeptides (including, for example, antibodies), and vaccines, as well as any other therapeutic molecule that could be packaged by the variant AAV capsid polypeptides of the invention.

AAV "rep" and "cap" genes refer to polynucleotide sequences encoding replication and encapsidation proteins of adeno-associated virus (AAV). AAV rep (replication) and cap (capsid) are referred to herein as AAV "packaging genes."

A "helper virus" for AAV refers to a virus allowing AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used as a helper virus. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome allowing AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virion, virus or viral particle is one comprising a polynucleotide component deliverable into a cell tropic for the viral species. The term does not necessarily imply any replication capacity of the virus. As used herein, an "infectious" virus or viral particle is one that upon accessing a target cell, can infect a target cell, and can express a heterologous nucleic acid in a target cell. Thus, "infectivity" refers to the ability of a viral particle to access a target cell, enter a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA) or fluorescence-activated cell sorting (FACS).

A "replication-competent" virion or virus (e.g. a replication-competent AAV) refers to an infectious phenotypically wild-type virus, and is replicable in an infected cell (i.e. in the presence of a helper virus or helper virus functions). In the case of AAV, replication competence generally requires the presence of functional AAV packaging genes. In some embodiments, AAV vectors, as described herein, lack of one or more AAV packaging genes and are replication-incompetent in mammalian cells (especially in human cells). In some embodiments, AAV vectors lack any AAV packaging gene sequences, minimizing the possibility of generating replication competent AAV by recombination between AAV packaging genes and an incoming AAV vector. In many embodiments, AAV vector preparations as described herein are those containing few if any replication competent AAV (rcAAV, also referred to as RCA) (e.g., less than about 1 rcAAV per $10^2$ AAV particles, less than about 1 rcAAV per $10^4$ AAV particles, less than about 1 rcAAV per $10^8$ AAV particles, less than about 1 rcAAV per $10^{12}$ AAV particles, or no rcAAV).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "gene" refers to a polynucleotide containing at least one open reading frame capable of encoding a particular protein or polypeptide after being transcribed and translated.

A "small interfering" or "short interfering RNA" or siRNA is a RNA duplex of nucleotides targeted to a gene interest (a "target gene"). An "RNA duplex" refers to the structure formed by the complementary pairing between two regions of a RNA molecule. siRNA is "targeted" to a gene and the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences forming the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome capable of modulating the productive utilization of mRNA. An artificial microRNA can be any type of RNA sequence, other than endogenous microRNA, capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim Pt al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA cleaved from a microRNA precursor (a "pre-miRNA"), or synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means the polynucleotide is the product of various combinations of cloning, restriction or ligation steps, and other procedures resulting in a construct distinct and/or different from a polynucleotide found in nature. A recombinant virus is a viral particle encapsidating a recombinant polynucleotide. The terms respectively include replicates of the original polynucleotide construct and progeny of the original virus construct.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters, enhancers and degrons. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from the rest of the entity to it is being compared too. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter. For example, an AAV including a heterologous nucleic acid encoding a heterologous gene product is an AAV including a nucleic acid not normally included in a naturally-occurring, wild-type AAV, and the encoded heterologous gene product is a gene product not normally encoded by a naturally-occurring, wild-type AAV. An AAV including a nucleic acid encoding a variant AAV capsid polypeptide includes a heterologous nucleic acid sequence. Once transferred/delivered into a host cell, a heterologous polynucleotide, contained within the virion, can be expressed (e.g., transcribed, and translated if appropriate). Alternatively, a transferred/delivered heterologous polynucleotide into a host cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or polynucleotide-liposome complexation. Genetic alteration may also be effected, for example, by transduction or infection with a DNA or RNA virus or viral vector. Generally, the genetic element is introduced into a chromosome or mini-chromosome in the cell; but any alteration changing the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced and inheritable by progeny of the altered cell.

The terms "polypeptide," "peptide," and "protein" are used interchangeably herein to refer to polymers of amino acids of any length. The "polypeptides," "proteins" and "peptides" encoded by the "polynucleotide sequences,"

include full-length native sequences, as with naturally occurring proteins, as well as functional subsequences, modified forms or sequence variants so long as the subsequence, modified form or variant retains some degree of functionality of the native full-length protein. In methods and uses of as described herein, such polypeptides, proteins and peptides encoded by the polynucleotide sequences can be but are not required to be identical to the defective endogenous protein, or whose expression is insufficient, or deficient in the treated mammal. The terms also encompass a modified amino acid polymer; for example, disulfide bond formation, glycosylation, lipidation, phosphorylation, methylation, carboxylation, deamidation, acetylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, retaining the desired biochemical function of the intact protein.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | cy. |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR,—NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitro-phenylalanine, hydroxy proline, 1,2,3, 4,-tetrahydroisoquinoline-3-carboxylic acid, and thioproline.

The term "variant" or "variants", with regard to polypeptides, such as capsid polypeptides refers to a polypeptide sequence differing by at least one amino acid from a parent polypeptide sequence, also referred to as a non-variant polypeptide sequence. In some embodiments, the polypeptide is a capsid polypeptide and the variant differs by at least one amino acid substitution. Amino acids also include naturally occurring and non-naturally occurring amino acids as well as derivatives thereof. Amino acids also include both D and L forms.

An "isolated" plasmid, nucleic acid, vector, virus, virion, host cell, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

By the term "highly conserved" is meant at least about 80% identity, preferably at least 90% identity, and more preferably, over about 97% identity. Identity is readily determined by one of skill in the art by resort to algorithms and computer programs known by those of skill in the art.

The term "percent sequence identity" or "identical" in the context of nucleic acid sequences refers to the residues in the two sequences that are the same when aligned for maximum correspondence. The length of sequence identity comparison may be over the full-length of the genome, the full-length of a gene coding sequence, or a fragment of at least about 500 to 5000 nucleotides. However, identity among smaller fragments, e.g. of at least about nine nucleotides, usually at least about 20 to about 24 nucleotides, at least about 28 to about 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering an AAV vector or AAV virion as disclosed herein, or transformed cell to a subject.

The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. AAV vectors or AAV virions, and pharmaceutical compositions thereof can be packaged in single or multiple unit dosage form for ease of administration and uniformity of dosage.

A "therapeutically effective amount" will fall in a relatively broad range determinable through experimentation and/or clinical trials. For example, for in vivo injection, e.g., injection directly into the tissue of a subject (for example, muscle tissue), a therapeutically effective dose will be on the order of from about $10^6$ to about $10^{15}$ of the AAV virions per kilogram bodyweight of the subject. In some embodiments, a therapeutically effective dose will be on the order of from about $10^8$ to $10^{12}$ AAV virions per kilogram bodyweight of the subject. Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

The phrase "enhanced neutralization profile" refers to the ability of an AAV vector or virion to better evade neutralizing antibody binding in the subject. In some instances, fewer neutralization antibodies allow for the AAV infection to generate higher levels of transduction, making the variant AAV capsid polypeptides, AAV vectors and virions of the present invention better suited for gene therapy purposes.

The phrases "tropism" and "transduction" are interrelated, but there are differences. The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

The term "tropism profile" refers to the pattern of transduction of one or more target cells, tissues and/or organs. For example, some shuffled AAV capsids (variant AAV capsid polypeptides) provide for efficient transduction of skeletal muscle (e.g., quadriceps muscle), diaphragm muscle and/or cardiac muscle tissue. Conversely, some shuffled AAV capsids have only low level transduction of liver, gonads and/or germ cells. The variant AAV capsid polypeptides disclosed herein provide for efficient and/or enhanced transduction of skeletal muscle.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 110%, 125%, 150%, 175%, or 200% or more of the transduction or tropism, respectively, of the control). Suitable controls will depend on a variety of factors including the desired tropism profile. Similarly, it can be determined if a capsid and/or virus "does not efficiently transduce" or "does not have efficient tropism" for a target tissue, or similar terms, by reference to a suitable control.

As used herein and in the appended claims, the singular forms "a," "an," and "the" include plural referents unless the context clearly dictates otherwise. Thus, for example, reference to "an AAV virion" includes a plurality of such virions and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

AAV Capsid and Vector Features

AAV vectors of the present invention have numerous features. In some embodiments, the vectors comprise nucleic acid sequences encoding for variant AAV capsid polypeptides. Such AAV vectors and their features are described in detail below.

An exemplary AAV vector of the present invention comprises a nucleic acid encoding for a variant AAV capsid protein differing in amino acid sequence by at least one amino acid from a wild-type or non-variant parent capsid protein. The amino acid difference(s) can be located in a solvent accessible site in the capsid, e.g., a solvent-accessible loop, or in the lumen (i.e., the interior space of the AAV capsid). In some embodiments, the lumen includes the interior space of the AAV capsid. For example, the amino acid substitution(s) can be located in a GH loop in the AAV capsid polypeptide. In some embodiments, the variant AAV capsid polypeptide comprises an amino acid substitution in AAV1, AAV2, AAV3, AAV4, AAV5, AAV6, AAV7, AAV8, or AAV9 capsid polypeptides.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to non-variant capsid amino acid sequences or to sub-portions of a non-variant parent capsid polypeptide sequence, and exhibits increased transduction or tropism in human muscle tissue or cells as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV4, AAV5, AAV6, AAV7, AAV8, or AAV9 capsid polypeptides, and where the variant AAV capsid polypeptide exhibits increased transduction or tropism in human muscle tissue or cells as compared to a vector encoding a non-variant parent capsid polypeptide. In some embodiments, the variant AAV capsid polypeptide comprises one or more regions or sub-portions from non-variant parent capsid polypeptide sequences from AAV serotypes 1, 6, 8, and 9 (i.e., AAV1, AAV6, AAV8, and AAV9).

In some embodiments, a subject AAV vector can encode variant capsid polypeptides having an amino acid sequence of at least about 85%, at least about 90%, at least about 95%, at least about 98%, or at least about 99%, or 100%, amino acid sequence identity to non-variant parent capsid polypeptides or to sub-portions of non-variant parent capsid polypeptides. In some embodiments, the variant AAV capsid polypeptide is encoded by other vectors/plasmids known in the art.

In some embodiments, the variant AAV capsid polypeptides exhibit substantial homology or "substantial similarity," when referring to amino acids or fragments thereof, indicating that, when optimally aligned with appropriate amino acid insertions or deletions with another amino acid (or its complementary strand), there is amino acid sequence identity in at least about 95% to about 99% of the aligned sequences. In some embodiments, the homology is over full-length sequence, or a polypeptide thereof, e.g., a capsid protein, or a fragment thereof of at least 8 amino acids, or more desirably, at least about 15 amino acids in length, including sub-portions of a non-variant parent capsid polypeptide sequence. For example, the variant AAV capsid polypeptide can comprise an amino acid sequence having at least about 85%, at least about 90%, at least about 95%, at least about 98%, at least about 99%, or 100%, amino acid sequence identity to a non-variant parent capsid polypeptide sequence or to sub-portions of a non-variant parent capsid polypeptides. In some embodiments the variant AAV capsid polypeptide sequence comprises any one of SEQ ID NOs: 1-7. In some embodiments, the variant AAV capsid polypeptide sequence is encoded by any one of SEQ ID NOs: 8-14.

TABLE 2

Variant AAV Capsid Sequences

| Description SEQ ID NO: | Sequence |
|---|---|
| NP6 amino acid SEQ ID NO: 1 | MAADGYLPDWLEDNLSEGIREWWDLKPGAPKPKANQQK QDDGRGLVLPGYKYLGPFNGLDKGEPVNAADAAALEHD KAYDQQLKAGDNPYLRYNHADAEFQERLQEDTSEGGNL GRAVFQAKKRVLEPLGLVEEGAKTAPGKKRPVEQSPQE PDSSSGIGKTGQQPAKKRLNEGQTGDSESVPDPQPLGE PPATPAAVGPTTMASGGGAPMADNNEGADGVGNASGNW HCDSTWLGDRVITTSTRTWALPTYNNHLYKQISSQSGA SNDNHYEGYSTPWGYEDENREHCHFSPRDWQRLINNNW GFRPKRLSFKLENIQVKEVTQNEGTKTIANNLTSTVQV FTDSEYQLPYVLGSAHQGCLPPFPADVFMVPQYGYLTL NNGSQAVGRSSFYCLEYFPSQMLRTGNNFTFSYTFEDV PFHSSYAHSQSLDRLMNPLIDQYLYYLSRTNTPSGTTT QSRLQFSQAGASDIRDQSRNWLPGPCYRQQRVSKTSAD NNNSEYSWTGATKYHLNGRDSLVNPGPAMASHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPADPPTTENQSKLNSFITQYSTGQVSVEIEW ELQKENSKRWNPEIQYTSNYYKSTSVDFAVNTEGVYSE PRPIGTRYLTRNL |
| NP20 amino acid SEQ ID NO: 2 | MAADGYLPDWLEDNLSEGIREWWDLKPGAPKPKANQQK QDDGRGLVLPGYKYLGPFNGLDKGEPVNAADAAALEHD KAYDQQLKAGDNPYLRYNHADAEFQERLQEDTSEGGNL GRAVFQAKKRVLEPLGLVEEGAKTAPGKKRPVEQSPQE PDSSSGIGKTGQQPAKKRLNEGQTGDSESVPDPQPLGE PPATPAAVGPTTMASGGGAPMADNNEGADGVGNASGNW HCDSQWLGDRVITTSTRTWALPTYNNHLYKQISSQSGA SNDNHYEGYSTPWGYEDENREHCHFSPRDWQRLINNNW GFRPKRLSFKLENIQVKEVTQNEGTKTIANNLTSTIQV FTDSEYQLPYVLGSAHQGCLPPEPADVFMIPQYGYLTL NNGSQAVGRSSFYCLEYFPSQMLRTGNNFQFTYTFEDV PFHSSYAHSQSLDRLMNPLIDQYLYYLSRTNTPSGTTT QSRLQFSQAGASDIRDQSRNWLPGPCYRQQRVSKTSAD NNNSEYSWTGATKYHLNGRDSLVNPGPAMASHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPANPSTTESAAKFASFITQYSTGQVSVEIEW ELQKENSKRWNPEIQYTSNYYKSVNVDFTVDTNGVYSE PRPIGTRYLTRNL |
| NP22 amino acid SEQ ID NO: 3 | MAADGYLPDWLEDNLSEGIREWWALKPGVPQPKANQQK QDDGRGLVLPGYKYLGPFNGLDKGEPVNAADAAALEHD KAYDQQLQAGDNPYLRYNHADAEFQERLQEDTSEGGNL GRAVFQAKKRVLEPLGLVEEPVKTAPGKKRPVEHSPVE PDSSSGTGKAGQQPARKRLNEGQTGDADSVPDPQPIGE PPAAPSGVGSLTMAAGGGAPMADNNEGADGVGNSSGNW HCDSQWLGDRVITTSTRTWALPTYNNHLYKQISSQSGA SNDNHYEGYSTPWGYEDENREHCHFSPRDWQRLINNNW GFRPKKLSFKLENIQVKEVTQNDGTKTIANNLTSTIQV FTDSEYQLPYVLGSAHQGCLPPEPADVFMIPQYGYLTL NNGSQAVGRSSFYCLEYFPSQMLRTGNNFQFTYTFEDV PFHSSYAHSQSLDRLMNPLIDQYLYYLSRTQTTGGTTN TQTLGESQGGPNTMANQAKNWLPGPCYRQQRVSKTSAD NNNSEYSWTGATKYHLNGRDSLVNPGPAMASHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPADPPTTENQSKLNSFITQYSTGQVSVEIEW ELQKENSKRWNPEIQYTSNYNKSVNVDFTVDTNGVYSE PRPIGTRYLTRNL |
| NP36 amino acid SEQ ID NO: 4 | MAADGYLPDWLEDNLSEGIREWWALKPGAPKPKANQQK QDDSRGLVLPGYKYLGPFNGLDKGEPVNEADAAALEHD GKAYDRQLDSGDNPYLKYNHADAEFQERLKEDTSEGGN LGRAVFQAKKRLLEPLGLVEEPVKTAPKKRPVEQSPQE PDSSSGIGKTGQQPARKRLNEGQTGDADSVPDPQPLGQ PPAAPSGLGTNTMATGSGAPMADNNEGADGVGNSSGNW HCDSTWMGDRVITISTRTWALPTYNNHLYKQISSQSGA SNDNHYFGYSTPWGYEDENREHCHFSPRDWQRLINNNW GFRPKKLSFKLENIQVKEVTQNDGTTTIANNLTSTVQV FTDSEYQLPYVLGSAHQGCLPPFPADVFMVPQYGYLTL NNGSQAVGRSSFYCLEYFPSQMLRTGNNFTESYTFEDV PFHSSYAHSQSLDRLMNPLIDQYLYYLSRTNTPSGTTT QSRLQFSQAGASDIRDQSRNWLPGPCYRQQRVSKTSAD NNNSEYSWTGATKYHLNGRDSLVNPGPAMASHKDDEEK FFPQSGVLIFGKQGSEKTDVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPANPSTTESAAKFASFITQYSTGQVSVEIEW ELQKENSKRWNPEIQYTSNYNKSVNVDFTVDTNGVYSE PRPIGTRYLTRNL |
| NP66 amino acid SEQ ID NO: 5 | MAADGYLPDWLEDNLSEGIREWWDLKPGAPKPKANQQK QDDGRGLVLPGYKYLGPFNGLDKGEPVNAADAAALEHD KAYDQQLKAGDNPYLRYNHADAEFQERLQEDTSEGGNL GRAVFQAKKRVLEPLGLVEEGAKTAPGKKRPVEQSPQE PDSSSGIGKTGQQPAKKRLNEGQTGDSESVPDPQPLGE PPATPAAVGPTTMASGGGAPMADNNEGADGVGNASGNW HCDSTWLGDRVITTSTRTWALPTYNNHLYKQISSQSGA SNDNHYFGYSTPWGYFDENREHCHFSPRDWQRLINNNW GFRPKRLSFKLENIQVKEVTQNEGTKTIANNLTSTIQV FTDSEYQLPYVLGSAHQGCLPPEPADVFMIPQYGYLTL NNGSQAVGRSSFYCLEYFPSQMLRTGNNFQFTYTFEDV PFHSSYAHSQSLDRLMNPLIDQYLYYLSRTQTTGGTTN TQTLGESQGGPNTMANQAKNWLPGPCYRQQRVSKTSAD NNNSEYSWTGATKYHLNGRDSLVNPGPAMASHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPADPPTTENQSKLNSFITQYSTGQVSVEIEW ELQKENSKRWNPEIQYTSNYYKSTSVDFAVNTEGVYSE PRPIGTRYLTRNL |
| NP81 amino acid SEQ ID NO: 6 | MAADGYLPDWLEDTLSEGIRQWWKLKPGPPPPKPAERH KDDSRGLVLPGYKYLGPFNGLDKGEPVNEADAAALEHD KAYDRQLDSGDNPYLKYNHADAEFQERLKEDTSEGGNL GRAVFQAKKRVLEPLGLVEEPVKTAPGKKRPVEHSPVE PDSSSGTGKAGQQPARKRLNEGQTGDADSVPDPQPLGQ PPAAPSGLGTNTMATGSGAPMADNNEGADGVGNSSGNW HCDSTWMGDRVITTSTRTWALPTYNNHLYKQISSQSGA SNDNHYFGYSTPWGYEDENREHCHFSPRDWQRLINNNW GFRPKKLSFKLENIQVKEVTQNEGTKTIANNLTSTIQV FTDSEYQLPYVLGSAHQGCLPPEPADVFMIPQYGYLTL NNGSQAVGRSSFYCLEYFPSQMLRTGNNFQFTYTFEGV PFHSSYAHSQSLDRLMNPLIDQYLYYLSRTQTTGGTTN TQTLGESQGGPNTMANQAKNWLPGPCYRQQRVSKTSAD NNNSEYSWTGATKYHLNGRDSLVNPGPAMTSHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPADPPTTENQSKLNSFITQYSTGQVSVEIEW ELQKENSKRWNPEIQYTSNYYKSTSVDFAVNTEGVYSE PRPIGTRYLTRNL |
| NP94 amino acid SEQ ID NO: 7 | MAADGYLPDWLEDNLSEGIREWWALKPGAPKPKANQQK QDDGRGLVLPGYKYLGPFNGLDKGEPVNAADAAALEHD KAYDQQLKAGDNPYLRYNHADAEFQERLQEDTSEGGNL GRAVFQAKKRVLEPLGLVEEGAKTAPGKKRPVEQSPQE PDSSSGIGKTGQQPAKKRLNEGQTGDSESVPDPQPLGE PPATPAAVGPTTMASGGGAPMADNNEGADGVGNASGNW HCDSQWLGDRVITTSTRTWALPTYNNHLYKQISSQSGA |

TABLE 2-continued

Variant AAV Capsid Sequences

| Description SEQ ID NO: | Sequence |
|---|---|
| | SNDNHYFGYSTPWGYEDENREHCHFSPRDWQRLINNNW GFRPKRLNEKLENIQVKEVTQNDGTTTIANNLTSTIQV FTDSEYQLPYVLGSAHQGCLPPEPADVFMIPQYGYLTL NNGSQAVGRSSFYCLEYFPSQMLRTGNNFTESYTFEDV PFHSSYAHSQSLDRLMNPLIDQYLYYLSRTNTPSGTTT QSRLQFSQAGASDIRDQSRNWLPGPCYRQQRVSKTSAD NNNSEYSWTGATKYHLNGRDSLVNPGPAMASHKDDEEK FFPQSGVLIFGKQGSEKTNVDIEKVMITDEEEIRTTNP VATEQYGSVSTNLQRGNRQAATADVNTQGVLPGMVWQD RDVYLQGPIWAKIPHTDGHFHPSPLMGGEGLKHPPPQI LIKNTPVPANPSTTESAAKFASFITQYSTGQVSVEIEW ELQKENSKRWNPEIQYTSNYNKSVNVDFTVDTNGVYSE PRPIGTRYLTRNL |
| NP6 nucleotide SEQ ID NO: 8 | ATGGCTGCCGATGGTTATCTTCCAGATTGGCTCGAGGA CAACCTTAGTGAAGGAATTCGCGAGTGGTGGGACTTGA AACCTGGAGCCCCGAAGCCCAAAGCCAACCAGCAAAAG CAGGACGACGGCCGGGGTCTGGTGCTTCCTGGCTACAA GTACCTCGGACCCTTCAACGGACTCGACAAGGGGGAGC CCGTCAACGCGGCGGACGCAGCGGCCCTCGAGCACGAC AAGGCCTACGACCAGCAGCTCAAAGCGGGTGACAATCC GTACCTGCGGTATAACCACGCCGACGCCGAGTTTCAGG AGCGTCTGCAAGAAGATACGTCTTTTGGGGGCAACCTC GGGCGAGCAGTCTTCCAGGCCAAGAAGCGGGTTCTGA ACCTCTCGGTCTGGTTGAGGAAGGCGCTAAGACGGCTC CTGGAAAGAAACGTCCGGTAGAGCAGTCGCCACAAGAG CCAGACTCCTCCTCGGGCATTGGCAAGACAGGCCAGCA GCCCGCTAAAAAGAGACTCAATTTTGGTCAGACTGGCG ACTCAGAGTCAGTCCCCGACCCACAACCTCTCGGAGAA CCTCCAGCAACCCCCGCTGCTGTGGGACCTACTACAAT GGCTTCAGGCGGTGGCGCACCAATGGCAGACAATAACG AAGGCGCCGACGGAGTGGGTAATGCCTCAGGAAATTGG CATTGCGATTCCACATGGCTGGGCGACAGAGTCATCAC CACCAGCACCCGAACCTGGGCCCTGCCCACCTACAACA ACCACCTCTACAAACAAATTTCCAGCCAATCAGGAGCC TCGAACGACAATCACTACTTTGGCTACAGCACCCCTTG GGGGTATTTTGATTTCAACAGATTCCACTGCCACTTTT CACCACGTGACTGGCAGCGACTCATCAACAACAATTGG GGATTCCGGCCCAAGAGACTCAGCTTCAAGCTCTTCAA CATCCAGGTCAAGGAGGTCACGCAGAATGAAGGCACCA AGACCATCGCCAATAACCTTACCAGCACCATCCAGGTG TTTACGGACTCGGAGTATCAGCTCCCGTACGTGCTCGG CTCGGCGCATCAAGGATGCCTCCCGCCGTTCCCAGCAG ACGTCTTCATGGTGCCACAGTATGGATACCTCACCCTC AACAACCGCAGTCAGGCACTAGGACGCTCTTCATTTTA CTGCCTGGAGTACTTTCCTTCTCAGATGCTGCGTACCG GAAACAACTTTACCTTCAGCTACACTTTTGAGGACGTT CCTTTCCACAGCAGCTACGCTCACAGCCAGAGTCTGGA CCGTCTCATGAATCCTCTGATTGACCAGTACCTGTATT ACTTGAGCAGAACAAACACTCCAAGTGGAACCACCACG CAGTCAAGGCTTCAGTTTTCTCAGGCCGGAGCGAGTGA CATTCGGGACCAGTCTAGGAACTGGCTTCCTGGACCCT GTTACCGCCAGCAGCGAGTATCAAAGACATCTGCGGAT AACAACAACAGTGAATACTCGTGGACTGGAGCTACCAA GTACCACCTCAATGGCAGAGACTCTCTGGTGAATCCGG GCCCGGCCATGGCAAGCCACAAGGACGATGAAGAAAAG TTTTTTCCTCAGAGCGGGGTTCTCATCTTTGGAAAGCA AGGCTCAGAGAAAACAAATGTGGACATTGAAAAGGTTA TGATTACAGACGAAGAGGAAATCAGGACAACCAATCCC GTGGCTACGGAGCAGTATGGTTCTGTATCTACCAACCT CCAGAGAGGCAACAGACAAGCAGCTACCGCAGATGTCA ACACACAAGGCGTTCTTCCAGGCATGGTCTGGCAGGAC AGAGATGTGTACCTTCAGGGGCCCATCTGGGCAAAGAT TCCACACACGGACGGACATTTTCACCCGTCTCCGCTGA TGGGCGGCTTTGGCCTGAAACATCCTCCGCCTCAGATC CTGATCAAGAACACGCCTGTACCTGCGGATCCTCCGAC CACCTTCAACCAGTCAAAGCTGAACTCTTTCATCACTC AGTATTCTACTGGCCAAGTCAGCGTGGAGATCGAGTGG GAGCTGCAGAAGGAAAACAGCAAGCGCTGGAATCCCGA GATCCAGTACACCTCCAACTACTACAAATCTACAAGTG TGGACTTTGCTGTTAATACAGAAGGCGTGTACTCTGAA CCCCGCCCCATTGGCACCCGTTACCTCACCCGTAATCT GTAA |
| NP20 nucleotide SEQ ID NO: 9 | ATGGCTGCCGATGGTTATCTTCCAGATTGGCTCGAGGA CAACCTCTCTGAGGGCATTCGCGAGTGGTGGGACTTGA AACCTGGAGCCCCGAAACCCAAAGCCAACCAGCAAAAG CAGGACGACGGCCGGGGTCTGGTGCTTCCTGGCTACAA GTACCTCGGACCCTTCAACGGACTCGACAAGGGGGAGC CCGTCAACGCGGCGGATGCAGCGGCCCTCGAGCACGAC AAGGCCTACGACCAGCAGCTCAAAGCGGGTGACAATCC GTACCTGCGGTATAACCACGCCGACGCCGAGTTTCAGG AGCGTCTGCAAGAAGATACGTCTTTTGGGGGCAACCTC GGGCGAGCAGTCTTCCAGGCCAAGAAGCGGGTTCTGA ACCTCTCGGTCTGGTTGAGGAAGGCGCTAAGACGGCTC CTGGAAAGAAACGTCCGGTAGAGCAGTCGCCACAAGAG CCAGACTCCTCCTCGGGCATCGGCAAGACAGGCCAGCA GCCCGCTAAAAAGAGACTCAATTTTGGTCAGACTGGCG ACTCAGAGTCAGTCCCCGACCCACAACCTCTCGGAGAA CCTCCAGCAACCCCCGCTGCTGTGGGACCTACTACAAT GGCTTCAGGCGGTGGCGCACCAATGGCAGACAATAACG AAGGCGCCGACGGAGTGGGTAATGCCTCAGGAAATTGG CATTGCGATTCCCAATGGCTGGGCGACAGAGTCATCAC CACCAGCACCCGAACCTGGGCCCTGCCCACCTACAACA ACCACCTCTACAAACAAATTTCCAGCCAATCAGGAGCC TCGAACGACAATCACTACTTTGGCTACAGCACCCCTTG GGGGTATTTTGACTTCAACAGATTCCACTGCCACTTTT CACCACGTGACTGGCAGCGACTCATCAACAACAACTGG GGATTCCGGCCCAAGAGACTCAGCTTCAAGCTCTTCAA CATCCAGGTCAAGGAGGTCACGCAGAATGAAGGCACCA AGACCATCGCCAATAACCTTACCAGCACCATCCAGGTG TTTACGGACTCGGAGTACCAGCTGCCGTACGTTCTCGG CTCTGCCCACCAGGGCTGCCTGCCTCCGTTCCCGGCGG ACGTGTTCATGATTCCCAGTACGGCTACCTAACACTC AACAACCGTAGTCAGGCCGTGGGACGCTCCTCCTTCTA CTGCCTGGAATACTTTCCTTCGCAGATGCTGAGAACCG GCAACAACTTCCAGTTTACTTACACCTTCGAGGACGTG CCTTTCCACAGCAGCTACGCTCACAGCCAGAGTCTGGA CCGTCTCATGAATCCTCTCATCGACCAGTACCTGTATT ACTTGAGCAGAACAAATACTCCAAGTGGAACCACCACG CAGTCAAGGCTTCAGTTTTCTCAGGCCGGAGCGAGTGA CATTCGGGACCAGTCTAGGAACTGGCTTCCTGGACCCT GTTACCGCCAGCAGCGAGTATCAAAGACATCTGCGGAT AACAACAACAGTGAATACTCGTGGACTGGAGCTACCAA GTACCACCTCAATGGCAGAGACTCTCTGGTGAATCCGG GCCCGGCCATGGCAAGCCACAAGGACGATGAAGAAAAG TTTTTTCCTCAGAGCGGGGTTCTCATCTTTGGAAAGCA AGGCTCAGAGAAAACAAATGTGGACATTGAAAAGGTTA TGATTACAGACGAAGAGGAAATCAGGACAACCAATCCC GTGGCTACGGAGCAGTATGGTTCTGTATCTACCAACCT CCAGAGAGGCAACAGACAAGCAGCTACCGCAGATGTCA ACACACAAGGCGTCTTCCAGGCATGGTCTGGCAGGAC AGAGATGTGTACCTTCAGGGGCCCATCTGGGCAAAGAT TCCACACACGGACGGACATTTTCACCCCTCTCCCCTCA TGGGTGGATTCGGACTTAAACACCCTCCTCCACAGATT CTCATCAAGAACACCCCCGGTACCTGCGAATCCTTCGAC CACCTTCAGTGCGGCAAAGTTTGCTTCTTCATCACAC AGTACTCCACGGGACAGGTCAGCGTGGAGATCGAGTGG GAGCTGCAGAAGGAAAACAGCAAACGCTGGAATCCCGA AATTCAGTACACTTCCAACTACAACAAGTCTGTTAATG TGGACTTTACTGTAGACACTAATGGTGTTTATAGTGAA CCTCGCCCTATTGGAACCCGGTATCTCACACGAAACTT GTAA |
| NP22 nucleotide SEQ ID NO: 10 | ATGGCTGCCGATGGTTATCTTCCAGATTGGCTCGAGGA CAACCTTTCTGAAGGCATTCGTGAGTGGTGGGCTCTGA AACCTGGAGTCCCTCAACCCAAAGCCAACCAGCAAAAG CAGGACGACGGCCGGGGTCTGGTGCTTCCTGGCTACAA GTACCTCGGACCCTTCAACGGACTCGACAAGGGGGAGC CCGTCAACGCGGCGGACGCAGCGGCCCTCGAGCACGAC AAGGCCTACGACCAGCAGCTGCAGGCGGGTGACAATCC GTACCTGCGGTATAACCACGCCGACGCCGAGTTTCAGG AGCGTCTGCAAGAAGATACGTCTTTTGGGGGCAACCTC GGGCGAGCAGTCTTCCAGGCCAAGAAGCGGGTTCTGA ACCTCTCGGTCTGGTTGAGGAAGGCGCTAAGACGGCTC CTGGAAAGAAGAGGCCTGTAGAGCACTCTCCTGTGGAG CCAGACTCCTCCTCGGGAACCGGAAAGGCGGGCCAGCA GCCTGCAAGAAAAAGATTGAATTTTGGTCAGACTGGAG |

TABLE 2-continued

Variant AAV Capsid Sequences

| Description SEQ ID NO: | Sequence |
|---|---|
| | ACGCAGACTCAGTCCCAGACCCTCAACCAATCGGAGAA<br>CCTCCCGCAGCCCCCTCAGGTGTGGGATCTCTTACAAT<br>GGCTGCAGGCGGTGGCGCACCAATGGCAGACAATAACG<br>AGGGTGCCGATGGAGTGGGTAATTCCTCAGGAAATTGG<br>CATTGCGATTCCCAATGGCTGGGCGACAGAGTCATCAC<br>CACCAGCACCCGAACCTGGGCCCTGCCCACTTACAACA<br>ACCATCTCTACACGCAAATCTCCAGCCAATCAGGAGCT<br>TCAAACGACAACCACTACTTTGGCTACAGCACCCCTTG<br>GGGGTATTTTGACTTTAACAGATTCCACTGCCACTTCT<br>CACCCACGTGACTGGCACCCACTCATTAACAACAACTGG<br>GGATTCCGGCCCAAGAAACTCAGCTTCAAGCTCTTCAA<br>CATCCAAGTTAAAGAGGTCACGCAGAATGATGGCACCA<br>AGACCATCGCCAATAACCTCACCAGCACCATCCAGGTG<br>TTTACGGACTCGGAGTACCAGCTGCCGTACGTTCTCGG<br>CTCTGCCCACCAGGGCTGCCTGCCTCCGTTCCCGGCCC<br>ACGTGTTCATGATTCCGCAGTACGGCTACCTAACACTC<br>AACAACGGTAGTCAGGCCGTGGGACGCTCCTCCTTCTA<br>CTGCCTGGAATACTTTCCTTCGCAGATGCTGAGAACCG<br>GCAACAACTTCAGTTTACTTACACCCTTCGAGGACGTG<br>CCTTTCCACAGCAGCTACGCTCACAGCCAGAGTCTGGA<br>CCGTCTCATGAATCCTCTCATCGACCAGTACCTGTATT<br>ACTTGTCTCGGACTCAAACAACAGGAGGCACGACAAAT<br>ACGCAGACTCTGGGCTTCAGCCAAGGTGGGCCTAATAC<br>AATGGCCAATCAGGCAAAGAACTGGCTGCCAGGACCCT<br>GTTACCGCCAGCAGCGAGTATCAAAGACATCTGCGGAT<br>AACAACAACAGTGAATACTCGTGGACTGGAGCTACCAA<br>GTACCACCTCAATGGCAGAGACTCTCTGGTGAATCCGG<br>GCCCGGCCATGGCAAGCCACAAGGACGATGAAGAAAAG<br>TTTTTTCCTCAGAGCGGGGTTCTCATCTTTGGGAAGCA<br>AGGCTCAGAGAAAACAAATGTGGACATTGAAAAGGTCA<br>TGATTACAGACGAAGAGGAAATCAGGACAACCAATCCC<br>GTGGCTACGGAGCAGTATGGTTCTGTATCTACCAACCT<br>CCAGAGAGGCAACAGACAAGCAGCTACCGCAGATGTCA<br>ACACACAAGGCGTTCTTCCAGGCATGGTCTGGCAGGAC<br>AGAGATGTGTACCTTCAGGGGCCCATCTGGGCAAAGAT<br>TCCACACACGGACGGACATTTTCACCCCTCTCCCCTGA<br>TGGGCGGCTTTGGCCTGAAACATCCTCCGCCTCAGATC<br>CTGATCAAGAACACGCCTGTACCTGCGGATCCTCCGAC<br>CACCTTCAACCAGTCAAAGCTGAACTCTTTCATCACTC<br>AGTATTCTACTGGCCAAGTCAGCGTGGAGATCGAGTGG<br>GAGCTGCAGAAGGAAAACAGCAAGCGCTGGAATCCCGA<br>AATTCAGTACACTTCCAACTACAACAAGTCTGTTAATG<br>TGGACTTTACTGTGGACACTAATGGCGTGTATTCAGAG<br>CCTCGCCCCATTGGCACCAGATACCTGACTCGTAATCT<br>GTAA |
| NP36 nucleotide SEQ ID NO: 11 | ATGGCTGCCGATGGTTATCTTCCAGATTGGCTCGAGGA<br>CAACCTCTCTGAGGGCATTCGCGAGTGGTGGGCGCTGA<br>AACCTGGAGCCCCGAAGCCCAAAGCCAACCAGCAAAAG<br>CAGGACGACAGCAGGGGTCTTGTGCTTCCTGGGTACAA<br>GTACCTCGGACCCTTCAACGGACTCGACAAGGGAGAGC<br>CGGTCAACGAGGCAGACGCCGCGGCCTGCCGCGAC<br>AAAGCCTACGACCAGCAGCTCGACAGCGGAGACAACCC<br>GTACCTCAAGTACAACCACGCCGACGCGGAGTTCCAGG<br>AGCGGCTCAAAGAAGATACGTCTTTTGGGGGCAACCTC<br>GGGCGAGCAGTCTTCCAGGCCAAAAAGAGGCTTCTTGA<br>ACCTCTTGGTCTGGTTGAGGAACCTGTTAAGACGGCTC<br>CTGGAAAGAAACGTCCGGTAGAGCAGTCGCCACAAGAG<br>CCAGACTCCTCCTCGGGCATCGGCAAGACAGGCCAGCA<br>GCCTGCAAGAAAAAGATTGAATTTTGGTCAGACTGGAG<br>ACGCAGACTCAGTACCTGACCCCTCGGACAC<br>CCACCAGCAGCCCCTCTGGTCTGGGAACTAATACGAT<br>GGCTACAGGCAGTGGCGCACCAATGGCAGACAATAACG<br>AGGGCGCCGACGGAGTGGGTAATTCCTCGGGAAATTGG<br>CATTGCGATTCCACATGGCTGGGCGACAGAGTCATCAC<br>CATCAGCACCCGAACCTGGGCCCTGCCCACTTACAACA<br>ACCACCTCTACAAACAAATTTCCAGCCAATCAGGAGCC<br>TCGAACGACAACCACTACTTTGGCTACAGCACCCCTTG<br>GGGGTATTTTGACTTTAACAGATTCCACTGCCACTTCT<br>CACCCACGTGACTGGCAGCGACTCATCAACAACAACTGG<br>GGATTCCGGCCCAAGAAACTCAGCTTCAAGCTCTTCAA<br>CATCCAGGTCAAGGAGGTCACGCAGAATGAAGGCACCA<br>AGACCATCGCCAATAACCTCACCAGCACCATCCAGGTG<br>TTTACGGACTCGGAGTATCAGCTCCCGTACGTGCTCGG |

| Description SEQ ID NO: | Sequence |
|---|---|
| | GTCGGCGCATCAAGGATGCCTCCCGCCGTTCCCAGCAG<br>ACGTCTTCATGGTGCCACAGTATGGATACCTCACCCTG<br>AACAACGGGAGTCAGGCAGTAGGACGCTCTTCATTTTA<br>CTGCCTGGAGTACTTTCCTTCTCAGATGCTGCGTACCG<br>GAAACAACTTTACCTTCAGCTACACTTTTGAGGACGTT<br>CCTTTCCACAGCAGCTACGCTCACAGCCAGAGTCTGGA<br>CCGTCTCATGAATCCTCTTATCGACCAGTACCTGTATT<br>ACTTGAGCAGAACAAACACTCCAAGTGGAACCACCACG<br>CAGTCAAGGCTTCAGTTTTCTCAGGCCGGAGCGAGTGA<br>CATTCGGGACCAGTCTAGGAACTGGCTTCCTGGACCCT<br>GTTACCGCCAGCAGCGAGTATCAAAGACATCTGCGGAT<br>AACAACAACAGTGAATACTCGTGGACTGGAGCTACCAA<br>GTACCACCTCAATGGCAGAGACTCTCTGGTGAATCCGG<br>GCCCGGCCATGGCAAGCCACAAGGACGATGAAGAAAAG<br>TTTTTTCCTCAGAGCGGGGTTCTCATCTTTGGGAAGCA<br>AGGCTCAGAGAAAACAGATGTGGACATTGAAAAGGTCA<br>TGATTACAGACGAAGAGGAAATCAGGACAACCAATCCC<br>GTGGCTACGGAGCAGTATGGTTCTGTATCTACCAACCT<br>CCAGAGAGGCAACAGACAAGCAGCTACCGCAGATGTCA<br>ACACACAAGGCGTTCTTCCAGGCATGGTCTGGCAGGAC<br>AGAGATGTGTACCTTCAGGGGCCCATCTGGGCAAAGAT<br>TCCACACACGGACGGACATTTTCACCCCTCTCCCCTCA<br>TGGGTGGATTCGGACTTAAACACCCTCCTCCACAGATT<br>CTCATCAAGAACACCCCGGTACCTGCGAATCCTTCGAC<br>CACCTTCAGTGCGGCAAAGTTTGCTTCTTCATCACAC<br>AGTACTCCACGGGACAGGTCAGCGTGGAGATCGAGTGG<br>GAGCTGCAGAAGGAAAACAGCAAACGCTGGAATCCCGA<br>AATTCAGTACACTTCCAACTACAACAAGTCTGTTAATG<br>TGGACTTTACTGTGGACACTAATGGCGTGTATTCAGAG<br>CCTCGCCCCATTGGCACCAGATACCTGACTCGTAATCT<br>GTAA |
| NP66 nucleotide SEQ ID NO: 12 | ATGGCTGCCGATGGTTATCTTCCAGATTGGCTCGAGGA<br>CAACCTTAGTGAAGGAATTCGCGAGTGGTGGGACTTGA<br>AACCTGGAGCCCCGAAGCCCAAAGCCAACCAGCAAAAG<br>CAGGACGACGCCGGGGGTCTGGTGCTTCCTGGCTACAA<br>GTACCTCGGACCCTTCAACGGACTCGACAAGGGGGAGC<br>CGGTCAACGCGGCGGACGCAGCGGCCCTCGAGCACGAC<br>AAGGCCTACGACCAGCAGCTCAAAGCGGGTGACAATCC<br>GTACCTGCGGTATAACCACGCGGACGCCGAGTTTCAGG<br>TAGCGTCTGCAAGAAGATACGTCTTTTGGGGGCAACCT<br>CGGGCGAGCAGTCTTCCAGGCCAAGAAGCGGGTTCTCG<br>AACCTCTCGGTCTGGTTGAGGAAGGCGCTAAGACGGCT<br>CCTGGAAAGAAACGTCCGGTAGAGCAGTCGCCACAAGA<br>GCCAGACTCCTCCTCGGGCATCGGCAAGACAGGCCAGC<br>AGCCCGCTAAAAAGAGACTCAATTTTGGTCAGACTGGC<br>GACTCAGAGTCAGTCCCCGACCCACAACCCTCGGAGAA<br>CCTCCAGCCACCCCCGCTGCTGTGGGACCTACTACAAT<br>GGCTTCAGGCGGTGGCGCACCAATGGCAGACAATAACG<br>AAGGCGCCGACGGAGTGGGTAATGCCTCAGGAAATTGG<br>CATTGCGATTCCACATGGCTGGGCGACAGAGTCATCAC<br>CACCAGCACCCGAACCTGGGCCCTGCCCACCTACAACA<br>ACCACCTCTACAAACAAATTTCCAGCCAATCAGGAGCC<br>TCGAACGACAATCACTACTTTGGCTACAGCACCCCTTG<br>GGGGTATTTTGACTTCAACAGATTCCACTGCCACTTTT<br>CACCACGTGACTGGCAGCGACTCATCAACAACAACTGG<br>GGATTCCGGCCCAAGAGACTCAGCTTCAAGCTCTTCAA<br>CATCCAGGTCAAGGAGGTCACGCAGAATGAAGGCACCA<br>AGACCATCGCCAATAACCTCACCAGCACCATCCAGGTG<br>TTTACGGACTCGGAGTACCAGCTGCCGTACGTTCTCGG<br>CTCTGCCCACCAGGGCTGCCTGCCTCCGTTCCCGGCCG<br>ACGTGTTCATGATTCCCAGTACGGCTACCTAACACTC<br>AACAACGGTAGTCAGGCCGTGGGACGCTCCTCCTTCTA<br>CTGCCTGGAATACTTTCCTTCGCAGATGCTGAGAACCG<br>GCAACAACTTCACTTTACTTACACCCTTCGAGGACGTG<br>CCTTTCCACAGCAGCTACGCCCACAGCCAGAGCTTGGA<br>CCGGCTGATGAATCCTCTGATTGACCAGTACCTGTACT<br>ACTTGTCTCGGACTCAAACAACAGGAGGCACGACAAAT<br>ACGCAGACTCTGGCCTTCAGCCAAGGTGGGCCTAATAC<br>AATGGCCAATCAGGCAAAGAACTGGCTGCCAGGACCCT<br>GTTACCGCCAGCAGCGAGTATCAAAGACATCTGCGGAT<br>AACAACAACAGTGAATACTCGTGGACTGGAGCTACCAA<br>GTACCACCTCAATGGCAGAGACTCTCTGGTGAATCCGG<br>GCCCGGCCATGGCAAGCCACAAGGACGATGAAGAAAAG |

TABLE 2-continued

Variant AAV Capsid Sequences

| Description SEQ ID NO: | Sequence |
|---|---|
| | TTTTTTCCTCAGAGCGGGGTTCTCATCTTTGGGAAGCA AGGCTCAGAGAAAACAAATGTGGACATTGAAAAGGTCA TGATTACAGACGAAGAGGAAATCAGGACAACCAATCCC GTGGCTACGGAGCAGTATGGTTCTGTATCTACCAACCT CCAGAGAGGCAACAGACAAGCAGCTACCGCAGATGTCA ACACACAAGGCGTTCTTCCAGGCATGGTCTGGCAGGAC AGAGATGTGTACCTTCAGGGGCCCATCTGGGCAAAGAT TCCACACACGGACGGACATTTTCACCCGTCTCCGCTGA TGGGCGGCTTTGGCCTGAAACATCCTCCGCCTCAGATC CTGATCAAGAACACGCCTGTACCTGCGGATCCTCCGAC CACCTTCAACCAGTCAAAGCTGAACTCTTTCATCACTC AGTATTCTACTGGCCAAGTCAGCGTGGAGATCGAGTGG GAGCTGCAGAAGGAAAACAGCAAGCGCTGGAACCCCGA GATCCAGTACACCTCCAACTACTACAAATCTACAAGTG TGGACTTTGCTGTTAATACAGAAGGCGTGTACTCTGAA CCCCGCCCCATTGGCACCCGTTACCTCACCCGTAATCT GTAA |
| NP81 nucleotide SEQ ID NO: 13 | ATGGCTGCCGATGGTTATCTTCCAGATTGGCTCGAGGA CACTCTCTCTGAAGGAATAAGACAGTGGTGGAAGCTCA AACCTGGCCCACCACCACCAAAGCCCGCAGAGCGGCAT AAGGACGACAGCAGGGGTCTTGTGCTTCCTGGGTACAA GTACCTCGGACCCTTCAACGGACTCGACAAGGGAGAGC CGGTCAACGAGGCAGACGCGCGGCCCTCGAGCACGAC AAAGCCTACGACCGGCAGCTCGACAGCGGAGACAACCC GTACCTCAAGTACAACCACGCCGACGCGGAGTTTCAGG AGCGCCTTAAAGAAGATACGTCTTTTGGGGGCAACCTC GGACGAGCAGTCTTCCAGGCGAAAAGAGGGTTCTTGA ACCTCTGGGCCTGGTTGAGGAACCTGTTAAGACGGCTC CGGGAAAAAAGAGGCCGGTAGAGCACTCTCCTGTGGAG CCAGACTCCTCCTCAGGAACCGGAAAGGCGGGCCAGCA GCCTGCAAGAAAAAGATTGAATTTTGGTCAGACTGGAG ACGCAGACTCAGTACCTGACCCCCAGCCTCTCGGACAG CCACCAGCAGCCCCTCTGGTCTGGGAACTAATACGAT GGCTACAGGCAGTGGCGCACCAATGGCAGACAATAACG AGGGCGCCGACGGAGTGGGTAATTCCTCGGGAAATTGG CATTGCGATTCCACATGGATGGGCGACAGAGTCATCAC CACCAGCACCCGAACCTGGGCCCTGCCCACCTACAACA ACCACCTCTACAAACAAATTTCCAGCCAATCAGGAGCC TCGAACGACAATCACTACTTTGGCTACAGCACCCCTTG GGGGTATTTTGACTTCAACAGATTCCACTGCCACTTCT CACCACGTGACTGGCAGCGACTCATTAACAACAACTGG GGATTCCGGCCCAAGAAACTCAGCTTCAAGCTCTTCAA CATCCAAGTTAAGGAGGTCACGCAGAATGAAGGCACCA AGACCATCGCCAATAACCTCACCAGCACCATCCAGGTG TTTACGGACTCGGAGTACCAGCTGCCGTACGTTCTCGG CTCTGCCCACCAGGGCTGCCTGCCTCCGTTCCCGGCGG ACGTGTTCATGATTCCCCAGTACGGCTACCTAACACTC AACAACGGTAGTCAGGCCGTGGGACGCTCCTCCTTCTA CTGCCTGGAATACTTTCCTTCGCAGATGCTGAGAACCG GCAACAACTTCCAGTTTACTTACACCTTCGAGGGCGTG CCTTTCCACAGCAGCTACGCCCACAGCCAGAGCTTGGA CCGGCTGATGAATCCTCTGATTGACCAGTACCTGTACT ACTTGTCTCGGACTCAAACAACAGGAGGCACGACAAAT ACGCAGACTCTGGGCTTCAGCCAAGGTGGGCCTAATAC AATGGCCAATCAGGCAAAGAACTGGCTGCCAGGACCCT GTTACCGCCAGCAGCGAGTATCAAAGACATCTGCGGAT AACAACAACAGTGAATACTCGTGGACTGGAGCTACCAA GTACCACCTCAATGGCAGAGACTCTCTGGTGAATCCGG GCCCGGCCATGACAAGCCACAAGGACGATGAAGAAAAG TTTTTTCCTCAGAGCGGGGTTCTCATCTTTGGGAAGCA AGGCTCAGAGAAAACAAATGTGGACATTGAAAAGGTTA TGATTACAGACGAAGAGGAAATCAGGACAACCAATCCC GTGGCTACGGAGCAGTATGGTTCTGTATCTACCAACCT CCAGAGAGGCAACAGACAAGCAGCTACCGCAGATGTCA ACACACAAGGCGTTCTTCCAGGCATGGTCTGGCAGGAC AGAGATGTGTACCTTCAGGGGCCCATCTGGGCAAAGAT TCCACACACGGACGGACATTTTCACCCCTCTCCCCTCA TGGGTGGATTCGGACTTAAACACCCTCCTCCACAGATT CTCATCAAGAACACCCCGGTACCTGCGAATCCTTCGAC CACCTTCAGTGCGGCAAAGTTTGCTTCCTTCATCACAC AGTACTCCACGGGACAGGTCAGCGTGGAGATCGAGTGG GAGCTGCAGAAGGAAAACAGCAAACGCTGGAATCCCGA AATTCAGTACACTTCCAACTACAACAAGTCTGTTAATG |
| | TGGACTTTACTGTGGACACTAATGGCGTGTATTCAGAG CCTCGCCCCATTGGCACCAGATACCTGACTCGTAATCT GTAA |
| NP94 nucleotide SEQ ID NO: 14 | ATGGCTGCCGATGGTTATCTTCCAGATTGGCTCGAGGA CAACCTTAGTGAAGGAATTCGCGAGTGGTGGGCTTTGA AACCTGGAGCCCCGAAACCCAAAGCCAACCAGCAAAAG CAGGACGACGGCCGGGGTCTGGTGCTTCCTGGCTACAA GTACCTCGGACCCTTCAACGGACTCGACAAGGGGGAGC CCGTCAACGCGGCGGATGCAGCGGCCCTCGAGCACGAC AAGGCCTACGACCAGCAGCTCAAAGCGGGTGACAATCC GTACCTGCGGTATAACCACGCCGACGCCGAGTTTCAGG AGCGTCTGCAAGAAGATACGTCTTTTGCGCGCAACCTC GCGCGAGCAGTCTTCCAGGCCAAGAAGCGGGTTCTCGA ACCTCTCGGTCTGGTTGAGGAAGGCGCTAAGACGGCTC CTGGAAAGAAACGTCCGGTAGAGCAGTCGCCCACAAGAG CCAGACTCCTCCTCGGGCATCGGCAAGACAGGCCAGCA GCCCGCTAAAAAGAGACTCAATTTTGGTCAGACTGGCG ACTCAGAGTCAGTCCCCGACCCACAACCTCTCGGAGAA CCTCCAGCAACCCCCGCTGCTGTGGGACCTACTACAAT GGCTTCAGGCGGTGGCGCACCAATGGCAGACAATAACG AAGGCGCCGACGGAGTGGGTAATGCCTCAGGAAATTGG CATTGCGATTCCCAATGGCTGGGCGACAGAGTCATCAC CACCAGCACCCGAACCTGGGCCCTGCCCACCTACAACA ACCACCTCTACAAACAAATTTCCAGCCAATCAGGAGCC TCGAACGACAATCACTACTTTGGCTACAGCACCCCCTTG GGGGTATTTTGACTTCAACAGATTCCACTGCCACTTTT CACCACGTGACTGGCAAAGACTCATCAACAACAACTGG GGATTCCGACCCAAGAGACTCAACTTCAAGCTCTTTAA CATTCAAGTCAAAGAGGTCACGCAGAATGACGGTACGA CGACGATTGCCAATAACCTTACCAGCACCATCCAGGTG TTTACGGACTCGGAGTACCAGCTGCCGTACGTTCTCGG CTCTGCCCACCAGGGCTGCCTGCCTCCGTTCCCGGCGG ACGTGTTCATGATTCCGCAATACGGCTACCTGACGCTC AACAACGGGAGTCAGGCAGTAGGACGCTCTTCATTTTA CTGCCTGGAGTACTTTCCTTCTCAGATGCTGCGTACCG GAAACAACTTTACCTTCAGCTACACTTTTGAGGACGTT CCTTTCCACAGCAGCTACGCTCACAGCCAGAGTCTGGA CCGTCTCATGAATCCTCTCATCGACCAGTACCTGTATT ACTTGAGCAGAACTCAAACCACTGGAGGCACTGCAAAC ACCCAAACCCTGGGCTTCAGTCAAGGTGGCCCTAACAC CATGGCAAATCAGGCCAAAAACTGGTTACCAGGACCCT GTTACCGCCAGCAGCGAGTATCAAAGACATCTGCGGAT AACAACAACAGTGAATACTCGTGGACTGGAGCTACCAA GTACCACCTCAATGGCAGAGACTCTCTGGTGAATCCGG GCCCGGCCATGGCAAGCCACAAGGACGATGAAGAAAAG TTTTTTCCTCAGAGCGGGGTTCTCATCTTTGGGAAAGCA AGGCTCAGAGAAACAAATGTGGACATTGAAAAGGTTA TGATTACAGACGAAGAGGAAATCAGGACAACCAATCCC GTGGCTACGGAGCAGTATGGTTCTGTATCTACCAACCT CCAGAGAGGCAACAGACAAGCAGCTACCGCAGATGTCA ACACACAAGGCGTTCTTCCAGGCATGGTCTGGCAGGAC AGAGATGTGTACCTTCAGGGGCCCATCTGGGCAAAGAT TCCACACACGGACGGACATTTTCACCCCTCTCCCCTCA TGGGTGGATTCGGACTTAAACACCCTCCTCCACAGATT CTCATCAAGAACACCCCGGTACCTGCGAATCCTTCGAC CACCTTCAGTGCGGCAAAGTTTGCTTCCTTCATCACAC AGTACTCCACGGGACAGGTCAGCGTGGAGATCGAGTGG GAGCTGCAGAAGGAAAACAGCAAACGCTGGAATCCCGA AATTCAGTACACTTCCAACTACAACAAGTCTGTTAATG TGGACTTTACTGTAGACACTAATGGTGTTTATAGTGAA CCTCGCCCTATTGGAACCCGGTATCTCACACGAAACTT GTAA |

In some embodiments, the variant AAV capsid polypeptides of the invention exhibit increased transduction in human muscle tissue or cells as compared to non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%.

In some embodiments, the variant AAV capsid polypeptides of the invention exhibit increased tropism in human muscle tissue or cells as compared to non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%.

In some embodiments, the variant AAV capsid polypeptides of the invention further exhibit an enhanced neutralization profile as compared to non-variant parent capsid polypeptides. In some embodiments, the variant AAV capsid polypeptides of the invention further exhibit an enhanced neutralization profile against pooled human immunoglobulins as compared to non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%.

In some embodiments, the variant AAV capsid polypeptides of the invention further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides of the invention further exhibit increased transduction or tropism in one or more non-muscle human tissues as compared to non-variant parent capsid polypeptides. In some embodiments, the variant AAV capsid polypeptides further exhibit increased transduction in one or more non-muscle human tissues as compared to a vector encoding non-variant parent capsid polypeptides. In some embodiments, the variant AAV capsid polypeptides further exhibit increased tropism in one or more non-muscle human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides of the invention further exhibit increased transduction or tropism in one or more non-muscle human tissues as compared to non-variant parent capsid polypeptides. In some embodiments, the variant AAV capsid polypeptides further exhibit increased transduction in one or more non-muscle human tissues as compared to a vector encoding non-variant parent capsid polypeptides. In some embodiments, the variant AAV capsid polypeptides further exhibit increased tropism in one or more non-muscle human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides contain a VP1 comprising AAV1. In some embodiments, the variant AAV capsid polypeptides contain a VP2 comprising AAV1. In some embodiments, the variant AAV capsid polypeptides contain a VP3 comprising AAV1, AAV2, and AAV8. In some embodiments, the variant AAV capsid polypeptides contain a VP1 comprising AAV3b and AAV8. In some embodiments, the variant AAV capsid polypeptides contain a VP2 comprising AAV2, AAV3b, and AAV9. In some embodiments, the variant AAV capsid polypeptides contain a VP3 comprising AAV2, AAV3b, and AAV8. In some embodiments, the variant AAV capsid polypeptides contain capsid sequences from AAV1, AAV6 and/or AAV8.

In some embodiments, the variant AAV capsid polypeptide sequence is selected from the group consisting of AAV-NP6 (SEQ ID NO: 1), AAV-NP20 (SEQ ID NO: 2), AAV-NP22, (SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7). For NP66, the unique region of VP1 is composed of AAV1, the unique region of VP2 is composed of AAV1, and VP3 is composed of AAV1, AAV2, and AAV8, as well as further de novo mutations (Thr at position 473). For NP22, the unique region of VP1 is composed of AAV3b and AAV8, VP2 is composed of AAV8, AAV3b and AAV6, VP3 is composed of AAV9_hu14, AAV3b, AAV8 and AAV2 as well as further de novo mutations (Ile at position 200; Leu at position 213). NP94 has an AAV8-based unique region of VP1, a unique region of VP2 entirely from AAV1, and a mixed VP3 with contributions from AAV1, AAV3b, AAV2, and AAV8. In some embodiments, the variant AAV capsid polypeptide comprises a sequence where VP1 is composed of AAV1 sequences, VP2 is composed of AAV1 sequences, and VP3 is composed of AAV1, AAV2, and AAV8 sequences. In some embodiments, the variant AAV capsid polypeptide comprises further de novo mutations. In some embodiments, the variant AAV capsid polypeptide comprises a sequence where VP1 is composed of AAV3b and AAV8 sequences, VP2 is composed of AAV8, AAV3b and AAV6 sequences, VP3 is composed of AAV9_hu14, AAV3b, AAV8 and AAV2 sequences. In some embodiments, the variant AAV capsid polypeptides comprise further de novo mutations. In some embodiments, the variant AAV capsid polypeptides comprise a sequence where VP1 comprises an AAV8-based unique region of VP1, a unique region of VP2 entirely from AAV1, and a mixed VP3 with sequences from AAV1, AAV3b, AAV2, and AAV8. In some embodiments, the variant AAV capsid polypeptides exhibit about 99%, about 98%, about 97%, about 96%, about 95%, about 94%, about 93%, about 92%, about 91%, or about 90% identity to non-variant parent capsid polypeptides. In some embodiments, the variant AAV capsid polypeptides exhibit about 99%, about 98%, about 97%, about 96%, about 95%, about 94%, about 93%, about 92%, about 91%, or about 90% identity to AAV-NP6 (SEQ ID NO: 1), AAV-NP20 (SEQ ID NO: 2), AAV-NP22, (SEQ ID NO: 3), AAV-NP36 (SEQ ID NO: 4), AAV-NP66 (SEQ ID NO: 5), AAV-NP81 (SEQ ID NO: 6), and/or AAV-NP94 (SEQ ID NO: 7). In some embodiments, the variant AAV capsid polypeptides exhibit about 99%, about 98%, about 97%, about 96%, about 95%, about 94%, about 93%, about 92%, about 91%, or about 90% identity to one or more subregions of AAV-NP6 (SEQ ID NO: 1), AAV-NP20 (SEQ ID NO: 2), AAV-NP22, (SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7).

The present invention also provides for generating variant AAV capsid polypeptides, such as AAV-NP66 (SEQ ID NO: 5), AAV-NP22 (SEQ ID NO: 3), and AAV-NP94 (SEQ ID NO: 7). These methods employ known techniques of library generation; however, the methods are novel in that they employ replication competent AAV vectors' during the variant AAV capsid polypeptide generation (i.e., selection and evolution of the variant AAV capsid polypeptides). The present invention provides methods for generating variant AAV capsid polypeptides, wherein the variant AAV capsid polypeptides exhibit increased transduction or tropism in human muscle tissue or cells as compared to non-variant parent capsid polypeptides, the method comprising:

a) generating a library of variant AAV capsid polypeptide genes, wherein said variant AAV capsid polypeptide genes include a plurality of variant AAV capsid polypeptide genes comprising sequences from more than one non-variant parent capsid polypeptide;

b) generating an AAV vector library by cloning said variant AAV capsid polypeptide gene library into AAV vectors, wherein said AAV vectors are replication competent AAV vectors;

c) screening said AAV vector library from b) for variant AAV capsid polypeptides exhibiting increased transduction or tropism in human muscle tissue or cells as compared to a non-variant parent capsid polypeptide; and d) selecting said variant AAV capsid polypeptides from c).

In some embodiments, the method further comprises e) determining the sequence of said variant AAV capsid polypeptides from d).

In some embodiments, the variant AAV capsid polypeptides generated by screening methods of the invention exhibit increased transduction in human muscle tissue or cells as compared to a vector encoding non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%.

In some embodiments, the variant AAV capsid polypeptides generated by screening methods of the invention exhibit increased tropism in human muscle tissue or cells as compared to a vector encoding non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%.

In some embodiments, the variant AAV capsid polypeptides generated by screening methods of the invention further exhibit an enhanced neutralization profile as compared to a vector encoding non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%.

In some embodiments, the variant AAV capsid polypeptides generated by screening methods of the invention further exhibit increased transduction or tropism in one or more non-muscle human tissues as compared to a vector encoding non-variant parent capsid polypeptides. In some embodiments, the variant AAV capsid polypeptides further exhibit increased transduction in one or more non-muscle human tissues as compared to a vector encoding non-variant parent capsid polypeptides. In some embodiments, the variant AAV capsid polypeptides further exhibit increased tropism in one or more non-muscle human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides generated by screening methods of the invention further exhibit increased transduction or tropism in one or more non-muscle human tissues as compared to a vector encoding non-variant parent capsid polypeptides. In some embodiments, the variant AAV capsid polypeptides further exhibit increased transduction in one or more non-muscle human tissues as compared to a vector encoding non-variant parent capsid polypeptides. In some embodiments, the variant AAV capsid polypeptides further exhibit increased tropism in one or more non-muscle human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

Transduction can be measured by techniques known in the art, including, for example, immunohistochemical analysis, including those described in Example 2 below, as well as other methods known in the art. In vitro transduction analysis can be performed in human muscle stem cells, human myotubes and mouse myoblasts, again as described in the art or as described in Example 2 below, including for example by measuring GFP expression (or another marker gene) in order to determine transduction. In vivo or ex vivo transduction analysis can be measured by techniques known in the art, including, for example, Firefly luciferase-based assays, again as described in the art or as described in Example 2 below, including for example by measuring luciferase expression (or another marker gene) in order to determine transduction. In some embodiments, marker expression from an AAV vector packaged with the variant AAV capsid polypeptides is compared to marker expression from an AAV vector packaged with the non-variant parent capsid polypeptides in order to determine changes in transduction efficiency. In some embodiments, the transduction is compared for different cell types in order to determine tropism, i.e., compare transduction from an AAV vector packaged with the variant AAV capsid polypeptide to transduction from an AAV packaged with the non-variant capsid polypeptide in at least two different cell types in order to determine tropism for a particular cell type, sometimes referred to as a tropism profile. In some embodiments, the at least one cell type is human muscle tissue or human muscle cells. In some embodiments, the at least one cell type is human muscle tissue or human muscle cells, including heart cells. In some embodiments, at least a second cell type includes but is not limited to blood cells, blood stem cells, liver cells, gonads, germ cells, joint tissue or cells, pancreas (including β-islet cells), spleen tissue or cells, the gastrointestinal tract (e.g., epithelium and/or smooth muscle), lung tissue or cells and/or kidney tissue or cells.

Such methods for generating the variant AAV capsid polypeptides include DNA shuffling of capsid proteins, which begins with families of capsid genes from an array or plurality of AAV pseudo-species (for example, AAV1, AAV2, AAV3b, AAV4, AAV5, AAV6, AAV7, AAV8, AAV9, AAV 9_hu14, bovine AAV, avian AAV), that are enzymatically shuffled to create a diverse library of capsid genes that can be cloned back into an AAV shuttle plasmid and utilized to produce live replicating viral libraries (see, for example, FIG. 1A). To maximize the likelihood that a shuffled capsids (i.e., variant AAV capsid polypeptides) could functionally transduce human skeletal muscle—as compared to muscles of model organisms typically used for pre-clinical evaluation—the invention contemplates performing two simultaneous screens in primary human skeletal muscle stem cells (huMSC) and human muscle myotube short-term cultures. In some embodiments, surgical skeletal muscle resections from human patients are digested and purified by fluorescent activated cell sorting (FACS) to isolate a defined huMSC population that is CD31−CD34−CD45−EGFR+ITBG1+Pax7+ for use in screening. These huMSC populations can be maintained and cultured in stem state or differentiated in short-term cultures to produce human myotubes (see, for example, FIG. 1C), each with highly defined media. In some embodiments, cells of each type are pooled at equal ratios from the human patient biopsies to maximize cellular/patient variety, and replicating screens (see, for example, FIG. 1D) and carried for six rounds of selection (see, for example, FIG. 1E) with diversity monitoring by sequencing beginning at round 3 and each round thereafter until the end of the screens. In some embodiments, characterization of the selected shuffled capsid variant sequences demonstrates diverse parental contribution.

Figure 2:
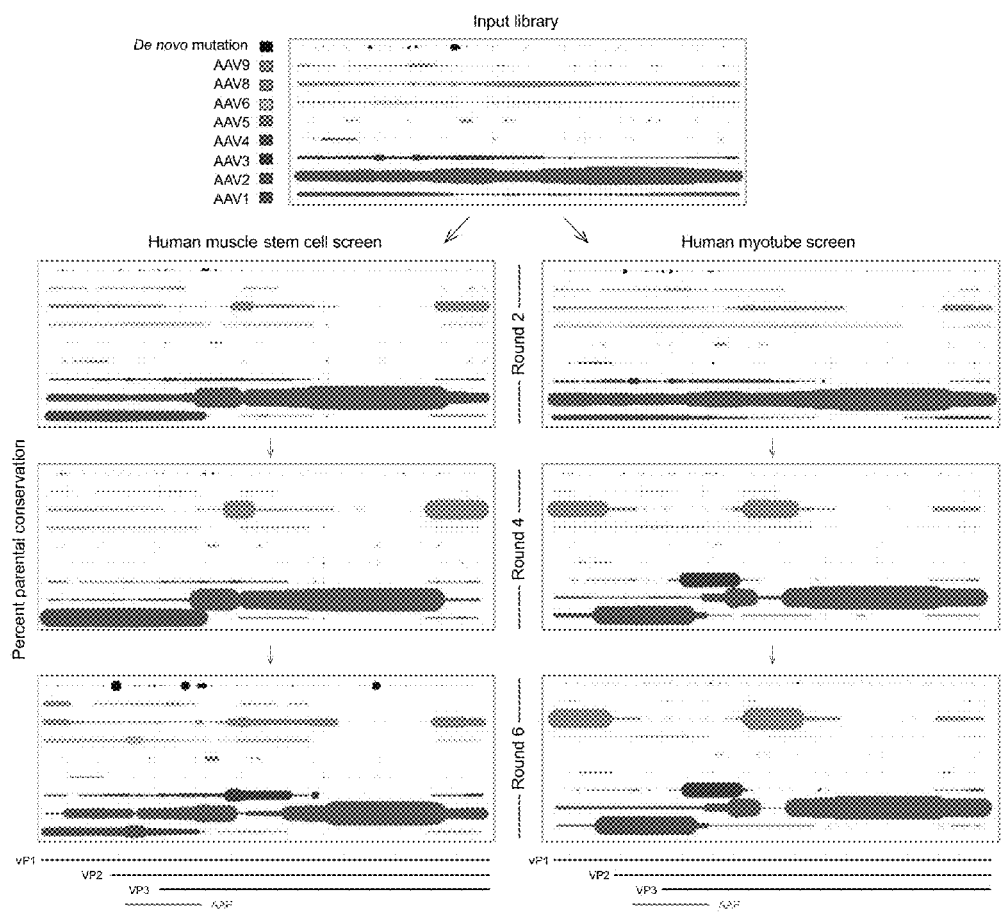
FIG. 2 shoes the percent parental conservation at each amino acid position during screen progression. Using PacBio long-range sequencing and bioinformatic analyses, positional assessments were performed to calculate percent conservation among amino acids from parental serotypes or de novo mutations for each amino acid position among all capsids at each round of the hMuSC and myotube screens. Dot diameter represents the percent of all capsids at that position that share the identical amino acid at that position from the eight parental serotypes. Each parent is colored as is shown in the legend (same color scheme used in FIG. 3A, B) and de novo mutations that evolved during the screen are shown in black. VP1, VP2, VP3 and AAP ORFs are shown below for reference.

At the completion of both screens, variants are chosen from each screened human cell type for full Sanger sequencing and phylogenetic comparisons to parental serotypes (i.e., parental non-variant capsid polypeptide sequences). In some embodiments, the parental non-variant capsid polypeptide sequences are those that went into the initial library. The most highly selected variants (for example, those that exhibit the highest increase in transduction and/or tropism) from each screen are isolated and vectorized with expression constructs, in some cases for use in subsequent validation experiments. In some embodiments, in order to assess the genetic contribution of each parental AAV serotype (i.e., non-variant parent capsid polypeptide) to the evolved capsids (i.e., variant AAV capsid polypeptides) selected from each screen, crossover mapping can be performed (see, for example, FIG. 2C) and bioinformatic prediction analyses (see, for example, FIG. 2D) to calculate enrichment scores for likelihood of parental (i.e., non-variant parent capsid polypeptide) contribution to each position in the new capsids (i.e., variant AAV capsid polypeptides). Both methodologies demonstrated the highly shuffled nature of the evolved capsid variants and highlighted both unique and shared domains present in selected capsids. In some embodiments, the parental capsids (i.e., non-variant parent capsid polypeptides) that contribute the most to the evolved variants include AAV1, AAV2, AAV3b, AAV8, and AAV9_hu14. In some embodiments, the variant AAV capsid polypeptides comprise regions from AAV1, AAV2, AAV3b, AAV8, and AAV9_hu14. In some embodiments, no variants (i.e., variant AAV capsid polypeptide) have capsid fragment regions from AAV4, 5, bovine or avian. In some embodiments, diverse shuffling was achieved and maintained along the length of Cap, including VP1, VP2 and VP3.

In vitro characterizations are used to demonstrate the significant increase in transduction by variant AAV capsid polypeptides over control serotypes (i.e., non-variant parent capsid polypeptides) in various muscle-derived cell lines.

For such analyses, large-scale ultrapure productions of AAV vectorized variants (AAV vectors composed of variant AAV capsid polypeptides) can be carried out and those capable of producing high titers sufficient for eventual clinical use (for example, variants NP6, NP22, NP36, NP66, NP81 and NP94) are considered further for validation. In some embodiments, further validation includes FLuc transduction efficiency assessments in vitro in huMSCs and human myotubes (see, for example, FIG. 3A), as well as in mouse myoblasts from normal and dystrophic mice (see, for example, FIG. 3B) with comparisons to the current best muscle-tropic AAV serotypes 1, 6 and 8. In some embodiments, in primary huMSCs, shuffled variants (i.e., variant AAV capsid polypeptides) exhibiting significantly increased functional transduction over vectors encoding AAV1, AAV6, and/or AAV8 non-variant parent capsids, by luciferase assay, can be selected by the present invention. In some embodiments, in human myotubes, shuffled variants (i.e., variant AAV capsid polypeptides) exhibiting significantly increased functional transduction over AAV1, AAV6, and/or AAV8, can be selected by the present invention. In some embodiments, in both normal and dystrophic mouse myoblasts, shuffled variants (i.e., variant AAV capsid polypeptides) exhibit highly significant increased transduction over all three control serotypes (i.e., AAV1, AAV6 or AAV8).

In order to examine the activity of the AAV vectors encoding the variant AAV capsid polypeptides of the invention, in one embodiment, chimeric humanized muscle xenografts are employed. Chimeric humanized muscle xenografts are a powerful surrogate for assessing potential skeletal muscle transduction in humans in vivo. To more rigorously assess the transduction capabilities of shuffled (i.e., variant AAV capsid polypeptides) and control AAV capsids (i.e., non-variant parent capsid polypeptides) in an in vivo setting, variants can be characterized using chimeric humanized muscle mouse xenograft model (as described in G. W. Charville, T. H. Cheung, B. Yoo, P. J. Santos, G. K. Lee, J. B. Shrager, T. A. Rando, *Stem cell reports* 5, 621-632 (2015); incorporated by reference herein for all purposes). In this novel model, primary FACS-isolated human muscle stem cells (see, for example, FIG. 1B) from patients are transplanted by direct intramuscular injection into the hind limbs of recipient immune-deficient mice. In this method, the human stem cells fuse with that of the mouse during engraftment, and create multi-nucleated chimeric muscle fibers upon differentiation over several months (see, for example FIG. 5B). Large cohorts of xenografted mice can be produced and then administered shuffled (i.e., AAV vectors encoding variant parent capsid polypeptides) or control rAAV variants (i.e., AA vectors encoding variant parent capsid polypeptides) by direct intramuscular injection and assessed for transduction in time-course studies, including studies for 1-month, 2-months, 3-months, 4-months, 5-months, or 6-months or more. In some embodiments, the AAV vector encoding a non-variant parent capsid polypeptide is the first vector to uncoat and express, but the AAV vector encoding a variant parent capsid polypeptide produces the highest sustained transduction levels. In some embodiments, the AAV vector encoding a non-variant parent capsid polypeptide exhibits decreasing expression with time. In some embodiments, transplantation efficiency and species-specific transduction are controlled for by simultaneous performance of the same transduction time course experiment in strain- and gender-matched non-transplanted immune-deficient mice.

In order to examine the activity of the AAV vectors encoding the variant AAV capsid polypeptides of the invention, further validation can be performed using ex vivo human skeletal muscle explants. Ex vivo human skeletal muscle explant transductions are employed to validate the significantly increased expression in human skeletal muscle specifically. Samples for use in ex vivo analyses and/or assays can include but are not limited to human skeletal muscle isolation from surgical specimens. Such human skeletal muscle specimens can be obtained from both male and female patients by surgical isolation from latissimus dorsi, serratus anterior, pectoralis major, rectus abdominis or any other skeletal muscle group. Samples for use in ex vivo analyses and/or assays can include but are not limited to non-human primate skeletal muscle isolation. Such samples can include Rhesus macaque skeletal muscle specimens isolated from the biceps femoris or any other skeletal muscle group.

In some embodiments, human skeletal muscle stem cells can be used for in vitro analyses and/or assays.

While chimeric humanized muscle xenografts are powerful tools to model human-like in vivo systems, they are limited in their ability to truly define expected transduction in human patients given the continued presence of mouse cells, as well as the chimeric nature of the fusion product fibers which express both mouse and human protein simultaneously. To overcome these limitations and more accurately predict eventual muscle transduction in human patients, transduction of live human skeletal muscle fiber explants from surgical resections ex vivo is contemplated by the methods of the invention. Muscle issue is obtained from the muscle of subjects via surgical procedures and employed for ex vivo transduction analyses. For such methods, skeletal muscle resections are digested and individual muscle fibers isolated for 24-hours, 48-hours, or 72-hours in culture and AAV vectors are administered within 30-minutes, 1-hour, 2-hours, 3-hours or 4-hours of removal of the muscle tissue from the subject. In some embodiments, skeletal muscle resections are digested and individual muscle fibers isolated for 48-hours in culture and AAV vectors are administered within 1 hour of removal of the muscle tissue from the subject. In some embodiments, ex vivo nonhuman primate skeletal muscle explant transduction can also be employed for further validation.

In some embodiments, increased transduction of AAV vectors encoding variant parent capsid polypeptides are exhibited in both dividing (myoblasts) and non-dividing (myotubes and myofibers) human skeletal muscle cell types. In some embodiments, increased transduction of AAV vectors encoding variant parent capsid polypeptides are exhibited in dividing (myoblasts). In some embodiments, increased transduction of AAV vectors encoding variant parent capsid polypeptides are exhibited in non-dividing (myotubes and myofibers) human skeletal muscle cell types.

AAV Vector Elements

The nucleic acid insert (also referred to as a heterologous nucleotide sequence) can be operably linked to control elements directing the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter can be operably linked to nucleic acid insert (also referred to as a heterologous nucleotide sequence) encoding the heterologous gene product, and allowing for selectively or preferentially producing a gene product in a particular cell type(s) or tissue(s). In some embodiments, an inducible promoter can be operably linked to the heterologous nucleic acid.

In some embodiments, the nucleic acid is packaged with the variant AAV capsid polypeptides of the invention. In some embodiments, the nucleic acid insert or packaged nucleic acid is at least 50, 100, 200, 300, 400, 500, 600, 700, 800, 900, 1000, 1100, 1200, 1300, 1400, or 1500 nucleic acids in length. In some embodiments, the nucleic acid insert or packaged nucleic acid is at least 50 nucleic acids to at least 1500 nucleic acids. In some embodiments, the nucleic acid insert or packaged nucleic acid is at least 100 nucleic acids to at least 1400 nucleic acids. In some embodiments, the nucleic acid insert or packaged nucleic acid is at least 200 nucleic acids to at least 1100 nucleic acids. In some embodiments, the nucleic acid insert or packaged nucleic acid is at least 300 nucleic acids to at least 1000 nucleic acids. In some embodiments, the nucleic acid insert or packaged nucleic acid is at least 100 nucleic acids to at least 900 nucleic acids. In some embodiments, the nucleic acid insert or packaged nucleic acid is at least 200 nucleic acids to at least 900 nucleic acids. In some embodiments, the nucleic acid insert or packaged nucleic acid is at least 300 nucleic acids to at least 900 nucleic acids. In some embodiments, the nucleic acid insert or packaged nucleic acid is at least 100 nucleic acids to at least 600 nucleic acids.

In some embodiments, the AAV vector packaged by the variant AAV capsid polypeptides is at least about 2000 nucleic acids in total length and up to about 5000 nucleic acids in total length. In some embodiments, the AAV vector packaged by the variant AAV capsid polypeptides is about 2000 nucleic acids, about 2400 nucleic acids, about 2800 nucleic acids, about 3000 nucleic acids, about 3200 nucleic acids, about 3400 nucleic acids, about 3600 nucleic acids, about 3800 nucleic acids, about 4000 nucleic acids, about 4200 nucleic acids, about 4400 nucleic acids, about 4600 nucleic acids, about 4700 nucleic acids, or about 4800 nucleic acids. In some embodiments, the AAV vector packaged by the variant AAV capsid polypeptides is between about 2000 nucleic acids (2 kb) and about 5000 nucleic acids (5 kb). In some embodiments, the AAV vector packaged by the variant AAV capsid polypeptides is between about 2400 nucleic acids (2.4 kb) and about 4800 nucleic acids (4.8 kb). In some embodiments, the AAV vector packaged by the variant AAV capsid polypeptides is between about 3000 nucleic acids (3 kb) and about 5000 nucleic acids (5 kb). In some embodiments, the AAV vector packaged by the variant AAV capsid polypeptides is between about 3000 nucleic acids (3 kb) and about 4000 nucleic acids (4 kb).

Purified infectious AAV virions contain three major structural proteins designated VP1, VP2, and VP3 (87, 73, and 62 kDa, respectively) in an approximate ratio of 1:1:8.

The AAV vectors or AAV virions disclosed herein can also include conventional control elements operably linked to the nucleic acid insert (also referred to as a heterologous nucleotide sequence) in a manner permitting transcription, translation and/or expression in a cell transfected with the AAV vector or infected with the AAV virion produced according to the present invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., Cell, 41:521-530 (1985)), the SV40 promoter, the dihydrofolate reductase promoter, the beta-actin promoter, the phosphoglycerol kinase (PGK) promoter, and the EF1 promoter (Invitrogen). Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clonetech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., (1996) *Proc. Natl. Acad. Sci. USA,* 93:3346-3351), the tetracycline-repressible system (Gossen et al., (1992) *Proc. Natl. Acad. Sci. USA,* 89:5547-5551), the tetracycline-inducible system (Gossen et al., (1995) *Science,* 268:1766-1769, see also Harvey et al., (1998) *Curr. Opin. Chem. Biol.,* 2:512-518), the RU486-inducible system (Wang et al., (1997) *Nat. Biotech.,* 15:239-243 and Wang et al., (1997)

*Gene Ther.,* 4:432-441) and the rapamycin-inducible system (Magari et al., (1997) *J. Clin. Invest.,* 100:2865-2872). Other types of inducible promoters useful in this context are those regulated by a specific physiological state, e.g., temperature, acute phase, a particular differentiation state of the cell, or in replicating cells only.

In another embodiment, the native promoter for the nucleic acid insert (also referred to as a heterologous nucleotide sequence) will be used. The native promoter may be preferred when it is desired that expression of the nucleic acid insert (also referred to as a heterologous nucleotide sequence) should mimic the native expression. The native promoter may be used when expression of the nucleic acid insert (also referred to as a heterologous nucleotide sequence) must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the nucleic acid insert (also referred to as a heterologous nucleotide sequence) includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., Nat. Biotech., 17:241-245 (1999)). Examples of promoters that are tissue-specific are known for liver (albumin, Miyatake et al., (1997) *J. Virol.,* 71:5124-32; hepatitis B virus core promoter, Sandig et al., (1996) *Gene Ther.,* 3:1002-9; alpha-fetoprotein (AFP), Arbuthnot et al., (1996) *Hum. Gene Ther.,* 7:1503-14), bone osteocalcin (Stein et al., (1997) *Mol. Biol. Rep.,* 24:185-96); bone sialoprotein (Chen et al., (1996) *J. Bone Miner. Res.,* 11:654-64), lymphocytes (CD2, Hansal et al., (1998) *J. Immunol.,* 161:1063-8; immunoglobulin heavy chain; T cell receptor chain), neuronal such as neuron-specific enolase (NSE) promoter (Andersen et al., (1993) *Cell. Mol. Neurobiol.,* 13:503-15), neurofilament light-chain gene (Piccioli et al., (1991) *Proc. Natl. Acad. Sci. USA,* 88:5611-5), and the neuron-specific vgf gene (Piccioli et al., (1995) *Neuron,* 15:373-84), among others.

In various embodiments, AAV vectors or AAV virions carrying one or more therapeutically useful nucleic acid inserts (also referred to as a heterologous nucleotide sequence) also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

Host Cells and Packaging

Host cells are necessary for generating infectious AAV vectors as well as for generating AAV virions based on the disclosed AAV vectors. Accordingly, the present invention provides host cells for generation and packaging of AAV virions based on the AAV vectors of the present invention. A variety of host cells are known in the art and find use in the methods of the present invention. Any host cells described herein or known in the art can be employed with the compositions and methods described herein.

The present invention provides host cells, e.g., isolated (genetically modified) host cells, comprising a subject nucleic acid. A subject host cell can be an isolated cell, e.g., a cell in in vitro culture. A subject host cell is useful for producing a subject AAV vector or AAV virion, as described below. Where a subject host cell is used to produce a subject AAV virion, it is referred to as a "packaging cell." In some embodiments, a subject host cell is stably genetically modified with a subject AAV vector. In other embodiments, a subject host cell is transiently genetically modified with a subject AAV vector.

In some embodiments, a subject nucleic acid is introduced stably or transiently into a host cell, using established techniques, including, but not limited to, electroporation, calcium phosphate precipitation, liposome-mediated transfection, baculovirus infection, and the like. For stable transformation, a subject nucleic acid will generally further include a selectable marker, e.g., any of several well-known selectable markers such as neomycin resistance, and the like.

Generally, when delivering the AAV vector according to the present invention by transfection, the AAV vector is delivered in an amount from about 5 µg to about 100 µg DNA, about 10 to about 50 µg DNA to about $1 \times 10^4$ cells to about $1 \times 10^{13}$ cells, or about $1 \times 10^5$ cells. However, the relative amounts of vector DNA to host cells may be adjusted, taking into consideration such factors as the selected vector, the delivery method and the host cells selected and such adjustments are within the level of skill of one in the art.

In some embodiments, the host cell for use in generating infectious virions can be selected from any biological organism, including prokaryotic (e.g., bacterial) cells, and eukaryotic cells, including, insect cells, yeast cells and mammalian cells. A subject host cell is generated by introducing a subject nucleic acid (i.e., AAV vector) into any of a variety of cells, e.g., mammalian cells, including, e.g., murine cells, and primate cells (e.g., human cells). Particularly desirable host cells are selected from among any mammalian species. In some embodiments, cells include without limitation, cells such as A549, WEHI, 10T1/2, BHK, MDCK, COS 1, COS 7, BSC 1, BSC 40, BMT 10, WI38, HeLa, CHO, 293, Vero, NIH 3T3, PC12, Huh-7 Saos, C2C12, RAT1, Sf9, L cells, HT1080, human embryonic kidney (HEK), human embryonic stem cells, human adult tissue stem cells, pluripotent stem cells, induced pluripotent stem cells, reprogrammed stem cells, organoid stem cells, bone marrow stem cells, HLHepG2, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirement for the cell used is it is capable of infection or transfection by an AAV vector. In some embodiments, the host cell is one that has Rep and Cap stably transfected in the cell, including in some embodiments a variant AAV capsid polypeptide as described herein. In some embodiments, the host cell expresses a variant AAV capsid polypeptide of the invention or part of an AAV vector as described herein, such as a heterologous nucleic acid sequence contained within the AAV vector.

In some embodiments, the preparation of a host cell according to the invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods providing the desired nucleotide sequence.

In some embodiments, introduction of the AAV vector into the host cell may also be accomplished using techniques known to the skilled artisan and as discussed throughout the specification. In a preferred embodiment, standard transfection techniques are used, e.g., $CaPO_4$ transfection or electroporation, and/or infection by hybrid adenovirus/AAV vectors into cell lines such as the human embryonic kidney cell line HEK293 (a human kidney cell line containing functional adenovirus E1 genes providing trans-acting E1 proteins).

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV Rep proteins. In other embodiments, a subject host cell further comprises an AAV vector. An AAV virion can be generated using a subject host cell. Methods of generating an AAV virion are described in, e.g., U.S. Patent Publication No. 2005/0053922 and U.S. Patent Publication No. 2009/0202490.

In addition to the AAV vector, in exemplary embodiments, the host cell contains the sequences driving expression of the AAV capsid polypeptide (including variant AAV capsid polypeptides and non-variant parent capsid polypeptides) in the host cell and Rep sequences of the same serotype as the serotype of the AAV Inverted Terminal Repeats (ITRs) found in the nucleic acid insert (also referred to as a heterologous nucleotide sequence), or a cross-complementing serotype. The AAV Cap and Rep sequences may be independently obtained from an AAV source and may be introduced into the host cell in any manner known to one of skill in the art or as described herein. Additionally, when pseudotyping an AAV vector in an AAV8 capsid for example, the sequences encoding each of the essential Rep proteins may be supplied by AAV8, or the sequences encoding the Rep proteins may be supplied by different AAV serotypes (e.g., AAV1, AAV2, AAV3, AAV4, AAV5, AAV6, AAV7, and/or AAV9).

In some embodiments, the host cell stably contains the capsid protein under the control of a suitable promoter (including, for example, the variant AAV capsid polypeptides of the invention), such as those described above. In some embodiments, the capsid protein is expressed under the control of an inducible promoter. In some embodiments, the capsid protein is supplied to the host cell in trans. When delivered to the host cell in trans, the capsid protein may be delivered via a plasmid containing the sequences necessary to direct expression of the selected capsid protein in the host cell. In some embodiments, when delivered to the host cell in trans, the vector encoding the capsid protein (including, for example, the variant AAV capsid polypeptides of the invention) also carries other sequences required for packaging the AAV, e.g., the Rep sequences.

In some embodiments, the host cell stably contains the Rep sequences under the control of a suitable promoter, such as those described above. In some embodiments, the essential Rep proteins are expressed under the control of an inducible promoter. In another embodiment, the Rep proteins are supplied to the host cell in trans. When delivered to the host cell in trans, the Rep proteins may be delivered via a plasmid containing the sequences necessary to direct expression of the selected Rep proteins in the host cell. In some embodiments, when delivered to the host cell in trans, the vector encoding the capsid protein (including, for example, the variant AAV capsid polypeptides of the invention) also carries other sequences required for packaging the AAV vector, e.g., the Rep sequences.

In some embodiments, the Rep and Cap sequences may be transfected into the host cell on a single nucleic acid molecule and exist stably in the cell as an unintegrated episome. In another embodiment, the Rep and Cap sequences are stably integrated into the chromosome of the cell. Another embodiment has the Rep and Cap sequences transiently expressed in the host cell. For example, a useful nucleic acid molecule for such transfection comprises, from 5' to 3', a promoter, an optional spacer interposed between the promoter and the start site of the Rep gene sequence, an AAV Rep gene sequence, and an AAV Cap gene sequence.

Although the molecule(s) providing Rep and capsid can exist in the host cell transiently (i.e., through transfection), in some embodiments, one or both of the Rep and capsid proteins and the promoter(s) controlling their expression be stably expressed in the host cell, e.g., as an episome or by integration into the chromosome of the host cell. The methods employed for constructing embodiments of the invention are conventional genetic engineering or recombinant engineering techniques such as those described in the references above.

In some embodiments, the packaging host cell can require helper functions in order to package the AAV vector of the invention into an AAV virion. In some embodiments, these functions may be supplied by a herpesvirus. In some embodiments, the necessary helper functions are each provided from a human or non-human primate adenovirus source, and are available from a variety of sources, including the American Type Culture Collection (ATCC), Manassas, Va. (US). In some embodiments, the host cell is provided with and/or contains an E1a gene product, an E1b gene product, an E2a gene product, and/or an E4 ORF6 gene product. In some embodiments, the host cell may contain other adenoviral genes such as VAI RNA. In some embodiments, no other adenovirus genes or gene functions are present in the host cell.

Heterologous Nucleic Acid, Nucleic Acid Gene Products, and Polypeptide Gene Products In various embodiments, the invention provides variant AAV capsid polypeptides capable of forming capsids capable of packaging a variety of therapeutic molecules, including nucleic acids and polypeptides. In some embodiments, the therapeutic molecule is a vaccine. In various embodiments, the invention provides for AAV vectors capable of containing nucleic acid inserts, including for example, transgene inserts or other nucleic acid inserts. This allows for vectors capable of expressing polypeptides. Such nucleic acids can comprise heterologous nucleic acid, nucleic acid gene products, and polypeptide gene products. Features of the nucleic acid inserts are described below.

In some embodiments, the AAV vectors described herein contain nucleic acid inserts. In some embodiments, the nucleic acid insert includes but is not limited to nucleic acid sequences selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the expression cassette is a CRISPR/CAS expression system.

In some embodiments, a nucleic acid insert comprises a heterologous nucleic acid comprising a nucleotide sequence encoding a heterologous gene product, e.g., a nucleic acid gene product or a polypeptide gene product. In some embodiments, the gene product is an interfering RNA (e.g., shRNA, siRNA, miRNA). In some embodiments, the gene product is an aptamer. The gene product can be a self-complementary nucleic acid. In some embodiments, the gene product is a polypeptide.

Suitable heterologous gene product includes interfering RNA, antisense RNA, ribozymes, and aptamers. Where the gene product is an interfering RNA (RNAi), suitable RNAi include RNAi that decrease the level of a target polypeptide in a cell.

In some embodiments, exemplary polypeptides, nucleic acids, or other therapeutic molecules include those useful in the treatment of rare sarcoglycanopathies and dystrophinopathies like Duchenne muscular dystrophy, limb girdle muscle disease, and spinal muscular atrophy, as well as other muscle tissue related diseases. Exemplary muscle tissue related diseases include but are not limited to Acid Maltase Deficiency (AMD), Amyotrophic Lateral Sclerosis (ALS), Andersen-Tawil Syndrome, Becker Muscular Dystrophy (BMD), Becker Myotonia Congenita, Bethlem Myopathy, Bulbospinal Muscular Atrophy (Spinal-Bulbar Muscular Atrophy), Carnitine Deficiency, Carnitine Palmityl Transferase Deficiency (CPT Deficiency), Central Core Disease (CCD), Centronuclear Myopathy, Charcot-Marie-Tooth Disease (CMT), Congenital Muscular Dystrophy (CMD), Congenital Myasthenic Syndromes (CMS), Congenital Myotonic Dystrophy, Cori Disease (Debrancher Enzyme Deficiency), Debrancher Enzyme Deficiency, Dejerine-Sottas Disease (DSD), Dermatomyositis (DM), Distal Muscular Dystrophy (DD), Duchenne Muscular Dystrophy (DMD), Dystrophia Myotonica (Myotonic Muscular Dystrophy), Emery-Dreifuss Muscular Dystrophy (EDMD), Endocrine Myopathies, Eulenberg Disease (Paramyotonia Congenita), Facioscapulohumeral Muscular Dystrophy (FSH or FSHD), Finnish (Tibial) Distal Myopathy, Forbes Disease (Debrancher Enzyme Deficiency), Friedreich's Ataxia (FA), Fukuyama Congenital Muscular Dystrophy, Glycogenosis Type 10, Glycogenosis Type 11, Glycogenosis Type 2, Glycogenosis Type 3, Glycogenosis Type 5, Glycogenosis Type 7, Glycogenosis Type 9, Gowers-Laing Distal Myopathy, Hauptmann-Thanheuser MD (Emery-Dreifuss Muscular Dystrophy), Hereditary Inclusion-Body Myositis, Hereditary Motor and Sensory Neuropathy (Charcot-Marie-Tooth Disease), Hyperthyroid Myopathy, Hypothyroid Myopathy, Inclusion-Body Myositis (IBM), Inherited Myopathies, Integrin-Deficient Congenital Muscular Dystrophy, Kennedy Disease (Spinal-Bulbar Muscular Atrophy), Kugelberg-Welander Disease (Spinal Muscular Atrophy), Lactate Dehydrogenase Deficiency, Lambert-Eaton Myasthenic Syndrome (LEMS), Limb-Girdle Muscular Dystrophy (LGMD), Lou Gehrig's Disease (Amyotrophic Lateral Sclerosis), McArdle Disease (Phosphorylase Deficiency), Merosin-Deficient Congenital Muscular Dystrophy, Metabolic Diseases of Muscle, Mitochondrial Myopathy, Miyoshi Distal Myopathy, Motor Neurone Disease, Muscle-Eye-Brain Disease, Myasthenia Gravis (MG), Myoadenylate Deaminase Deficiency, Myofibrillar Myopathy, Myophosphorylase Deficiency, Myotonia Congenita (MC), Myotonic Muscular Dystrophy (MMD), Myotubular Myopathy (MTM or MM), Nemaline Myopathy, Nonaka Distal Myopathy, Oculopharyngeal Muscular Dystrophy (OPMD), Paramyotonia Congenita, Pearson Syndrome, Periodic Paralysis, Peroneal Muscular Atrophy (Charcot-Marie-Tooth Disease), Phosphofructokinase Deficiency, Phosphoglycerate Kinase Deficiency, Phosphoglycerate Mutase Deficiency, Phosphorylase Deficiency, Phosphorylase Deficiency, Polymyositis (PM), Pompe Disease (Acid Maltase Deficiency), Progressive External Ophthalmoplegia (PEO), Rod Body Disease (Nemaline Myopathy), Spinal Muscular Atrophy (SMA), Spinal-Bulbar Muscular Atrophy (SBMA), Steinert Disease (Myotonic Muscular Dystrophy), Tarui Disease (Phosphofructokinase Deficiency), Thomsen Disease (Myotonia COngenita), Ullrich Congenital Muscular Dystrophy, Walker-Warburg Syndrome (Congenital Muscular Dystrophy), Welander Distal Myopathy, Werdnig-Hoffmann Disease (Spinal Muscular Atrophy), and ZASP-Related Myopathy.

In some embodiments, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-.beta.), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, VEGF, an anti-VEGF antibody, a soluble VEGFR, Factor VIII (FVIII), Factor IX (FIX), and a member of the hedgehog family (sonic hedgehog, Indian hedgehog, and desert hedgehog, etc.).

In some embodiments, useful therapeutic products encoded by the heterologous nucleic acid sequence include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor alpha superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

In some embodiments, useful heterologous nucleic acid sequence products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors alpha and beta., interferons (alpha, beta, and gamma), stem cell factor, flk-2/flt3 ligand. Gene products produced by the immune system are also useful in the present invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

In some embodiments, useful heterologous nucleic acid sequence products include any one of the receptors for the hormones, growth factors, cytokines, lymphokines, regulatory proteins and immune system proteins. Useful heterologous nucleic acid sequences also include receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses the use of gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MyoD and myogenin, ETS-box containing proteins, TFE3, E2F, ATF1, ATF2, ATF3, ATF4, ZF5, NFAT, CREB, HNF-4 C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

In some embodiments, useful heterologous nucleic acid sequence products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes useful in enzyme replacement therapy, and which are useful in a variety of conditions resulting from deficient activity of enzyme. For example, enzymes containing mannose-6-phosphate may be utilized in therapies for lysosomal storage diseases (e.g., a suitable gene includes that encoding β-glucuronidase (GUSB)).

In some embodiments, useful heterologous nucleic acid sequence products include those used for treatment of hemophilia, including hemophilia B (including Factor IX) and hemophilia A (including Factor VIII and its variants, such as the light chain and heavy chain of the heterodimer and the B-deleted domain; U.S. Pat. No. 6,200,560 and U.S. Pat. No. 6,221,349). The Factor VIII gene codes for 2351 amino acids and the protein has six domains, designated from the amino to the terminal carboxy terminus as A1-A2-B-A3-C1-C2 (Wood et al., (1984) *Nature,* 312:330; Vehar et al., (1984) *Nature* 312:337; and Toole et al., (1984) *Nature,* 342:337). Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, releasing the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, used to reduce overexpression of a target.

In some embodiments, the present invention provides methods for treatment of a stem cell disorder, for example a disorder in either bone marrow stem cells or adult tissue stem cells (i.e., somatic stem cells). In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, the disorder for treatment is a disorder in any one or more organoid stem cells (i.e., stem cells derived from any organ or organ system of interest within the body). In some embodiments, the treatment is in vivo (for example, administration of the variant AAV capsid polypeptides is directly to the subject). In some embodiments, the treatment is ex vivo (for example, administration of the variant AAV capsid polypeptides is to stem cells isolated from the subject and the treated stem cells are then returned to the subject).

Reduction and/or modulation of expression of a heterologous nucleic acid sequence is particularly desirable for treatment of hyperproliferative conditions characterized by hyperproliferating cells, such as cancers and psoriasis. Target polypeptides include those polypeptides produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are used as target antigens for autoimmune disease. Other tumor-associated polypeptides can be used as target polypeptides such as polypeptides found at higher levels in tumor cells including the polypeptide recognized by monoclonal antibody 17-1A and folate binding polypeptides.

In some embodiments, suitable therapeutic polypeptides and proteins include those useful for treating individuals suffering from autoimmune diseases and disorders by conferring a broad based protective immune response against targets that are associated with autoimmunity including cell receptors and cells producing "self"-directed antibodies. T cell mediated autoimmune diseases include Rheumatoid arthritis (RA), multiple sclerosis (MS), Sjogren's syndrome, sarcoidosis, insulin-dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T-cell receptors (TCRs) that bind to endogenous antigens and initiate the inflammatory cascade associated with autoimmune diseases.

In some embodiments, heterologous nucleic acid sequences encode for immunogens useful to immunize (i.e., useful as, for example, a vaccine) a human or non-human animal against other pathogens including bacteria, viruses, fungi, parasitic microorganisms or multicellular parasites infecting human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative *bacilli* include enterobacteriaceae; *pseudomonas*, acinetobacteria and *eikenella*; melioidosis; *salmonella; shigella; haemophilus; moraxella; H. ducreyi* (causes chancroid); *brucella* species (brucellosis); *Francisella tularensis* (causes tularemia); *Yersinia pestis* (plague) and other *Yersinia* (pasteurella); *Streptobacillus moniliformis* and spirillum; Gram-positive bacilli include *Listeria monocytogenes; Erysipelothrix rhusiopathiae; Corynebacterium diphtheria* (causes diphtheria); cholera; *Bacillus. anthracia* (causes anthrax); donovanosis (granuloma inguinale; caused by *Klebsiella granulomatis*); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever; Rocky Mountain spotted fever; Q fever (*Coxiella burnetti*); and Rickettsialpox. Examples of *mycoplasma* and chlamydial infections include: *Mycoplasma pneumoniae*; lymphogranuloma venereum (caused by *Chlamydia trachomatis*); psittacosis; and perinatal chlamydial infections. Pathogenic eukaryotes encompassing pathogenic protozoans and helminths and infections produced thereby include: amebiasis (caused by *Entamoeba histolpica*); malaria (caused by *Plasmodium*); Leishmaniasis (caused by *Leishmania*); trypanosomiasis (caused by *Trypanosoma*); toxoplasmosis (caused by *Toxoplasma gondii*); *Pneumocystis carinii*; babesiosis (caused by *Babesia*); giardiasis (caused by *Giardia lamblia*); trichinosis (caused by roundworms of the genus *Trichinella*); filariasis (caused by roundworms of Filarioidea); schistosomiasis (carried by fresh water snails infected with one of the five varieties of the parasite *Schistosoma*); nematodes (Nematoda), trematodes or flukes (Platyhelminthes); and cestode (Cestoidea; tapeworm) infections. Examples of viruses include, but are not limited to, human immunodeficiency virus (HIV; e.g., HIV-1 and HIV-2), influenza (e.g., influenza A, influenza B, and influenza C), parainfluenza hepatitis virus (e.g., hepatitis A, hepatitis B, hepatitis C, hepatitis D, and hepatitis E), herpes viruses (HSV; HHV; e.g., herpes virus types 1, 2, 3, 4, 5, 6A, 6B, 7, and 8, including herpes simplex virus types 1 and 2, aka, HSV-1; HSV-2), varicella-zoster virus (HHV-3), Epstein Barr virus (HHV-4), Roseolovirus (HHV-6A and HHV-6B); Rous sarcoma virus, cytomegalovirus (HHV-5), Kaposi's sarcoma-associated herpesvirus; KSHV; HHV-8), papovirus (e.g., human papilloma virus; HPV; HPV-1, HPV-2, HPV-16, and HPV-18), parvovirus (e.g., Parvovirus B19), orthomyxovirus, paramyxovirus (e.g., morbillivirus, respirovirus, rubulavirus, ferlavirus, pneumovirus, and metapneumovirus), picornavirus (e.g., foot-and-mouth disease virus, aquamavirus A, encephalomyocarditis virus, theilovirus, cosavirus A, cadicivirus A, enterovirus A, enterovirus B, enterovirus C, enterovirus D, enterovirus E, enterovirus F, enterovirus G, enterovirus H, enterovirus J, rhinovirus A, rhinovirus B, rhinovirus C, aichivirus A, aichivirus B, aichivirus C, melegrivirus A, human parechovirus, ljungan virus, and salivirus A), togavirus (e.g., flavivirus, alphavirus, and rubivirus), Cowpox virus, Horsepox virus, Crimean-Congo hemorrhagic fever virus, Dengue virus, Eastern equine encephalitis virus, Ebola virus, Hantaan virus, Human coronavirus, Human enterovirus 68, Human enterovirus 70, non-HIV retroviruses, rhinovirus, respiratory syncytial virus (RSV), SARS coronavirus, Human spumaretrovirus, Human T-lymphotropic virus, Isfahan virus, Japanese encephalitis virus, Lassa virus, Lymphocytic choriomeningitis virus, MERS coronavirus, measles virus, Mengo encephalomyocarditis virus, Monkeypox virus, mumps virus, Norwalk virus, Pichinde virus, Poliovirus, Rabies virus, rotavirus (e.g., rotavirus A, rotavirus B, and rotavirus C), Rubella virus, St. louis encephalitis virus, Toscana virus, Uukuniemi virus, Venezuelan equine encephalitis virus, Western equine encephalitis virus, West Nile virus, Yellow fever virus, and ZIKA virus, as well as any other viruses known to those of skill in the art.

Methods for Generating an AAV Virion

In various embodiments, the invention provides a method for generating an AAV virion of the invention. A variety of methods for generating AAV virions are known in the art and can be used to generate AAV virions comprising the AAV vectors described herein. Generally, the methods involve inserting or transducing an AAV vector of the invention into a host cell capable of packaging the AAV vector into an AAV virion. Exemplary methods are described and referenced below; however, any method known to one of skill in the art can be employed to generate the AAV virions of the invention.

An AAV vector comprising a heterologous nucleic acid and used to generate an AAV virion can be constructed using methods that are well known in the art. See, e.g., Koerber et al. (2009) *Mol. Ther.*, 17:2088; Koerber et al. (2008) *Mol Ther.*, 16: 1703-1709; as well as U.S. Pat. Nos. 7,439,065, 6,951,758, and 6,491,907. For example, the heterologous sequence(s) can be directly inserted into an AAV genome with the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in*

Biotechnology 3:533-539; Muzyczka, N. (1992) *Curr. Topics Microbiol. Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

In order to produce AAV virions, an AAV vector is introduced into a suitable host cell using known techniques, such as by transfection. A number of transfection techniques are generally known in the art. See, e.g., Graham et al. (1973) *Virology,* 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome-mediated gene transfer (Mannino et al. (1988) *BioTechniques* 6:682-690), lipid-mediated transduction (Feigner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing AAV virions include any species and/or type of cell that can be, or have been, used as recipients of a heterologous AAV DNA molecule, and can support the expression of required AAV production cofactors from helper viruses. Such host cells can include but are not limited to microorganisms, yeast cells, insect cells, and mammalian cells, that can be, or have been, used as recipients of a heterologous DNA molecule. The term includes the progeny of the original cell transfected. Thus, a "host cell" as used herein generally refers to a cell transfected with an exogenous DNA sequence. Cells from the stable human cell line, HEK293 (readily available through, e.g., the American Type Culture Collection under Accession Number ATCC CRL1573) can be used. The human cell line HEK293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The HEK293 cell line is readily transfected, and provides a convenient platform in which to produce AAV virions.

Methods of producing an AAV virion in insect cells are known in the art, and can be used to produce a subject AAV virion. See, e.g., U.S. Patent Publication No. 2009/0203071; U.S. Pat. No. 7,271,002; and Chen (2008) *Mol. Ther.* 16:924.

In some embodiments, the AAV virion or AAV vector is packaged into an infectious virion or virus particle, by any of the methods described herein or known in the art.

In some embodiments, the variant AAV capsid polypeptide allows for similar packaging as compared to a non-variant parent capsid polypeptide.

In some embodiments, an AAV vector packaged with the variant AAV capsid polypeptides transduce into cells in vivo better than a vector packaged from non-variant parent capsid polypeptides.

In some embodiments, the AAV vector packaged with the variant AAV capsid polypeptides transduce into cells in vitro better than a vector packaged from non-variant parent capsid polypeptides.

In some embodiments, the variant AAV capsid polypeptides result in nucleic acid expression higher than a nucleic acid packaged from non-variant parent capsid polypeptides.

In some embodiments, the AAV vector packaged with said variant AAV capsid polypeptides result in transgene expression better than a transgene packaged from non-variant parent capsid polypeptides.

Pharmaceutical Compositions & Dosing

The present invention provides pharmaceutical compositions useful in treating subjects according to the methods of the invention as described herein. Further, the present invention provides dosing regimens for administering the described pharmaceutical compositions. The present invention provides pharmaceutical compositions comprising: a) a subject AAV vector or AAV virion, as described herein as well as therapeutic molecules packaged by or within capsids comprising variant polypeptides as described herein; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro, (2000) *Remington: The Science and Practice of Pharmacy,* 20th edition, Lippincott, Williams, & Wilkins; *Pharmaceutical Dosage Forms and Drug Delivery Systems* (1999) H. C. Ansel et al., eds., 7$^{th}$ ed., Lippincott, Williams, & Wilkins; and *Handbook of Pharmaceutical Excipients* (2000) A. H. Kibbe et al., eds., 3$^{rd}$ ed. Amer. Pharmaceutical Assoc.

A subject composition can comprise a liquid comprising a subject variant AAV capsid polypeptide of the invention or AAV virion comprising a variant AAV capsid polypeptide in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have opthalmically compatible pH and osmolality.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound. Preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Useful carriers include Vaseline®, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the AAV vector or AAV virion and methods and uses of are known in the art (see, e.g., *Remington: The Science and Practice of Pharmacy* (2003) 20$^{th}$ ed., Mack Publishing Co., Easton, Pa.; *Remington's Pharmaceutical Sciences* (1990) 18$^{th}$ ed., Mack Publishing Co., Easton, Pa.; *The Merck Index* (1996) 12$^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Doses can vary and depend upon whether the treatment is prophylactic or therapeutic, the type, onset, progression, severity, frequency, duration, or probability of the disease treatment is directed to, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within about 1 hour to about 2 hours, about 2 hours to about 4 hours, about 4 hours to about 12 hours, about 12 hours to about 24 hours or about 24 hours to about 72 hours after a subject has been identified as having the disease targeted for treatment, has one or more symptoms of the disease, or has been screened and is identified as positive as set forth herein even though the subject does not have one or more symptoms of the disease. In some embodiments, the invention as disclosed herein can be practiced within about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 36 hours, about 48 hours, or about 72 hours or more. Of course, methods and uses of the invention can be practiced about 1 day to about 7 days, about 7 days to about 14 days, about 14 days to about 21 days, about 21 days to about 48 days or more, months or years after a subject has been identified as having the disease targeted for treatment, has one or more symptoms of the disease, or has been screened and is identified as positive as set forth herein. In some embodiments, the invention as disclosed herein can be practiced within about 1 day, about 2 days, about 3 days, about 4 days, about 5 days, about 6 days, about 7 days, about 8 days, about 9 days, about 10 days, about 11 days, about 12 days, about 14 days, about 21 days, about 36 days, or about 48 days or more.

In some embodiments, the present invention provides kits with packaging material and one or more components therein. A kit typically includes a label or packaging insert including a description of the components or instructions for use in vitro, in vivo, or ex vivo, of the components therein. A kit can contain a collection of such components, e.g., a variant AAV capsid polypeptide, an AAV vector, or AAV virion and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying the manufacturer, lot numbers, manufacturer location and date, expiration dates. Labels or inserts can include information identifying manufacturer information, lot numbers, manufacturer location and date. Labels or inserts can include information on a disease a kit component may be used for. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another incompatible treatment protocol or therapeutic regimen and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Method of Treating a Disease

The present invention also provides methods for treatment of disease in a subject by administering the AAV vectors and/or nucleic acids of the present invention, where AAV vectors and/or nucleic acids described herein packaged within a functional AAV capsid, wherein the functional AAV capsid comprises one or more variant AAV capsid polypeptides of the present invention. In an exemplary embodiment, the invention provides a method of administering a pharmaceutical composition of the invention to a subject in need thereof to treat a disease of a subject. In various embodiments, the subject is not otherwise in need of administration of a composition of the invention. In some embodiments, the invention provides methods for vaccine administration.

In some embodiments, the variant AAV capsid polypeptides package a therapeutic expression cassette comprised of a heterologous nucleic acid comprising a nucleotide sequence encoding a heterologous gene product, such as for example a therapeutic protein or vaccine. In some embodiments, the AAV virion or AAV vector comprises a therapeutic expression cassette comprised of a heterologous nucleic acid comprising a nucleotide sequence encoding a heterologous gene product, such as for example a therapeutic protein or vaccine.

In some embodiments, the variant AAV capsid polypeptides of the invention are employed as part of vaccine delivery. Vaccine delivery can include delivery of any of the therapeutic proteins as well as nucleic acids described herein. In some embodiments, variant AAV capsid polypeptides of the invention are employed as part of a vaccine regimen and dosed according to the methods described herein.

In some embodiments, the variant AAV capsid polypeptides, the AAV virions, or AAV vectors of the invention are used in a therapeutic treatment regimen.

In some embodiments, the variant AAV capsid polypeptides, the AAV virions, or AAV vectors of the invention are used for therapeutic polypeptide production.

In some cases, a subject variant AAV capsid polypeptides or AAV vector, when introduced into the cells of a subject, provides for high level production of the heterologous gene product packaged by the variant AAV capsid polypeptides or encoded by the AAV vector. For example, a heterologous polypeptide packaged by the variant AAV capsid polypeptides or encoded by the AAV can be produced at a level of from about 1 µg to about 50 µg or more.

In some cases, subject variant AAV capsid polypeptides, AAV virion, or AAV vector, when introduced into a subject, provide for production of the heterologous gene product packaged by the variant AAV capsid polypeptides or encoded by the AAV vector in at least about 10%, at least about 15%, at least about 20%, at least about 25%, at least about 30%, at least about 35%, at least about 40%, at least about 50% at least about 60%, at least about 70%, at least about 80%, or more than 80%, of the target cells.

In some embodiments, the present invention provides a method of treating a disease, the method comprising administering to an individual in need thereof an effective amount of a therapeutic molecule packaged by the variant AAV capsid polypeptides or subject AAV vector as described above.

Subject variant AAV capsid polypeptides or subject AAV vectors can be administered systemically, regionally or locally, or by any route, for example, by injection, infusion, orally (e.g., ingestion or inhalation), or topically (e.g., transdermally). Such delivery and administration methods include intravenously, intramuscularly, intraperitoneally, intradermally, subcutaneously, intracavity, intracranially, transdermally (topical), parenterally, e.g. transmucosally or rectally. Exemplary administration and delivery routes include intravenous, intraperitoneal, intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, and intralymphatic.

In some cases, a therapeutically effective amount of a therapeutic molecule packaged by the variant AAV capsid polypeptides or a subject AAV vectors is an amount that, when administered to an individual in one or more doses, is effective to slow the progression of the disease or disorder in the individual, or is effective to ameliorate symptoms. For example, a therapeutically effective amount of a therapeutic molecule packaged by the variant AAV capsid polypeptides or a subject AAV vectors can be an amount that, when administered to an individual in one or more doses, is effective to slow the progression of the disease by at least about 15%, at least about 20%, at least about 25%, at least about 30%, at least about 40%, at least about 50%, at least about 60%, at least about 70%, at least about 80%, or more than about 80%, compared to the progression of the disease in the absence of treatment with the therapeutic molecule packaged by the variant AAV capsid polypeptides or AAV vectors.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Improvement of clinical symptoms can also be monitored by one or more methods known to the art, and used as an indication of therapeutic effectiveness. Clinical symptoms may also be monitored by anatomical or physiological means, such as indirect ophthalmoscopy, fundus photography, fluorescein angiopathy, optical coherence tomography, electroretinography (full-field, multifocal, or other), external eye examination, slit lamp biomicroscopy, applanation tonometry, pachymetry, autorefaction, or other measures of functional vision. In some embodiments, a therapeutic molecule (including, for example, a vaccine) packaged by the variant AAV capsid polypeptides, a subject AAV vector, or AAV virus, when introduced into a subject, provides for production of the heterologous gene product for a period of time of from about 2 days to about 6 months, e.g., from about 2 days to about 7 days, from about 1 week to about 4 weeks, from about 1 month to about 2 months, or from about 2 months to about 6 months. In some embodiments, therapeutic molecules (including, for example, a vaccine) packaged by the variant AAV capsid polypeptides, a subject AAV vector or virus, when introduced into a subject provides for production of the heterologous gene product encoded for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years. In some embodiments, the administration regimen is part of a vaccination regimen.

Multiple doses of a subject AAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject AAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors. In some embodiments, the administration regimen is part of a vaccination regimen.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine a virion dose range to treat a patient having a particular disease or disorder based on the aforementioned factors, as well as other factors. Generally, doses will range from at least about, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

In some embodiments, the variant AAV polypeptides of the present invention can be employed to reduce the amount of total AAV vector or other therapeutic molecule administered to a subject, wherein less total AAV vector or other therapeutic molecule is administered to a subject when said AAV vector or other therapeutic molecule is transduced using variant AAV capsid polypeptides as compared to the amount of AAV vector or other therapeutic molecule administered to a subject when the AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total vector or other therapeutic molecule administered to a subject is reduced by about 5%, about 10%, about 15%, about 20%, about 25%, about 30%, about 35%, about 40%, about 50%, about 55%, about 60%, about 65%, about 70%, about 75%, about 80% or more when an AAV vector or other therapeutic molecule is transduced using variant AAV capsid polypeptides as compared to when an AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total AAV vector or other therapeutic molecule administered to a subject is reduced by about 5% to about 80%, about 10% to about 75%, about 15% to about 65%, about 20% to about 60%, or about 10% to about 50% when the AAV vector or other therapeutic molecule is transduced using variant AAV capsid polypeptides as compared to when the AAV vector or other therapeutic molecule is transduced using non-variant parent capsid polypeptides in order to obtain a similar therapeutic effect (i.e., both dosages induce similar therapeutic effects or indistinguishable therapeutic effects).

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

With regard to a disease or symptom thereof, or an underlying cellular response, a detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Disclosed methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of an AAV vector or AAV virion as described herein. The invention therefore provides combinations where a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of an AAV vector or AAV virion as described herein, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

Non-limiting particular examples of diseases treatable in accordance with the invention include those set forth herein as well as a lung disease (e.g., cystic fibrosis), a blood coagulation or bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency or defect, choroideremia, and other diseases of the eye), and a disease of a solid organ (e.g., brain, liver, kidney, heart), as well as muscle diseases including not limited to Acid Maltase Deficiency (AMD), Amyotrophic Lateral Sclerosis (ALS), Andersen-Tawil Syndrome, Becker Muscular Dystrophy (BMD), Becker Myotonia Congenita, Bethlem Myopathy, Bulbospinal Muscular Atrophy (Spinal-Bulbar Muscular Atrophy), Carnitine Deficiency, Carnitine Palmityl Transferase Deficiency (CPT Deficiency), Central Core Disease (CCD), Centronuclear Myopathy, Charcot-Marie-Tooth Disease (CMT), Congenital Muscular Dystrophy (CMD), Congenital Myasthenic Syndromes (CMS), Congenital Myotonic Dystrophy, Cori Disease (Debrancher Enzyme Deficiency), Debrancher Enzyme Deficiency, Dejerine-Sottas Disease (DSD), Dermatomyositis (DM), Distal Muscular Dystrophy (DD), Duchenne Muscular Dystrophy (DMD), Dystrophia Myotonica (Myotonic Muscular Dystrophy), Emery-Dreifuss Muscular Dystrophy (EDMD), Endocrine Myopathies, Eulenberg Disease (Paramyotonia Congenita), Facioscapulohumeral Muscular Dystrophy (FSH or FSHD), Finnish (Tibial) Distal Myopathy, Forbes Disease (Debrancher Enzyme Deficiency), Friedreich's Ataxia (FA), Fukuyama Congenital Muscular Dystrophy, Glycogenosis Type 10, Glycogenosis Type 11, Glycogenosis Type 2, Glycogenosis Type 3, Glycogenosis Type 5, Glycogenosis Type 7, Glycogenosis Type 9, Gowers-Laing Distal Myopathy, Hauptmann-Thanheuser MD (Emery-Dreifuss Muscular Dystrophy), Hereditary Inclusion-Body Myositis, Hereditary Motor and Sensory Neuropathy (Charcot-Marie-Tooth Disease), Hyperthyroid Myopathy, Hypothyroid Myopathy, Inclusion-Body Myositis (IBM), Inherited Myopathies, Integrin-Deficient Congenital Muscular Dystrophy, Kennedy Disease (Spinal-Bulbar Muscular Atrophy), Kugelberg-Welander Disease (Spinal Muscular Atrophy), Lactate Dehydrogenase Deficiency, Lambert-Eaton Myasthenic Syndrome (LEMS), Limb-Girdle Muscular Dystrophy (LGMD), Lou Gehrig's Disease (Amyotrophic Lateral Sclerosis), McArdle Disease (Phosphorylase Deficiency), Merosin-Deficient Congenital Muscular Dystrophy, Metabolic Diseases of Muscle, Mitochondrial Myopathy, Miyoshi Distal Myopathy, Motor Neurone Disease, Muscle-Eye-Brain Disease, Myasthenia Gravis (MG), Myoadenylate Deaminase Deficiency, Myofibrillar Myopathy, Myophosphorylase Deficiency, Myotonia Congenita (MC), Myotonic Muscular Dystrophy (MMD), Myotubular Myopathy (MTM or MM), Nemaline Myopathy, Nonaka Distal Myopathy, Oculopharyngeal Muscular Dystrophy (OPMD), Paramyotonia Congenita, Pearson Syndrome, Periodic Paralysis, Peroneal Muscular Atrophy (Charcot-Marie-Tooth Disease), Phosphofructokinase Deficiency, Phosphoglycerate Kinase Deficiency, Phosphoglycerate Mutase Deficiency, Phosphorylase Deficiency, Phosphorylase Deficiency, Polymyositis (PM), Pompe Disease (Acid Maltase Deficiency), Progressive External Ophthalmoplegia (PEO), Rod Body Disease (Nemaline Myopathy), Spinal Muscular Atrophy (SMA), Spinal-Bulbar Muscular Atrophy (SBMA), Steinert Disease (Myotonic Muscular Dystrophy), Tarui Disease (Phosphofructokinase Deficiency), Thomsen Disease (Myotonia Congenita), Ullrich Congenital Muscular Dystrophy, Walker-Warburg Syndrome (Congenital Muscular Dystrophy), Welander Distal Myopathy, Werdnig-Hoffmann Disease (Spinal Muscular Atrophy), and ZASP-Related Myopathy.

Ocular diseases that can be treated or prevented using a subject method include, but are not limited to, selected from acute macular neuroretinopathy; macular telangiectasia; Behcet's disease; choroidal neovascularization; diabetic uveitis; histoplasmosis; macular degeneration, such as acute macular degeneration, Scorsby's macular dystrophy, early or intermediate (dry) macular degeneration, or a form of advanced macular degeneration, such as exudative macular degeneration or geographic atrophy; edema, such as macular edema, cystoid macular edema and diabetic macular edema; multifocal choroiditis; ocular trauma affecting a posterior ocular site or location; ocular tumors; retinal disorders, such as central retinal vein occlusion, diabetic retinopathy (including proliferative and non-proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy; epiretinal membrane disorders; central or branch retinal vein occlusion; anterior ischemic optic neuropathy, non-retinopathy diabetic retinal dysfunction; retinitis pigmentosa; retinoschisis; and glaucoma.

In one embodiment, a method or use of the invention includes: (a) providing an AAV virion whose capsid comprises the variant AAV capsid polypeptides prepared as described herein, wherein the AAV virion comprises a heterologous nucleic acid sequence, wherein the heterologous nucleic acid sequence is operably linked to an expression control element conferring transcription of said nucleic acid sequence; and (b) administering an amount of the AAV virion to the mammal such that said heterologous nucleic acid is expressed in the mammal.

In one embodiment, a method or use of the invention includes: (a) providing a therapeutic molecule (including, for example, a vaccine) packaged by variant AAV capsid polypeptides prepared as described herein, wherein the therapeutic molecule comprises a heterologous nucleic acid sequence, wherein the heterologous nucleic acid sequence is operably linked to an expression control element conferring transcription of said nucleic acid sequence; and (b) administering an amount of the therapeutic molecule (including, for example, a vaccine) packaged by variant AAV capsid polypeptides to the mammal such that said heterologous nucleic acid is expressed in the mammal.

In another embodiment, a method or use of the invention includes delivering or transferring a heterologous polynucleotide sequence into a mammal or a cell of a mammal, by administering a heterologous polynucleotide packaged by the variant AAV capsid polypeptides, a plurality of heterologous polynucleotides packaged by variant AAV capsid polypeptides, an AAV virion prepared as described herein, or a plurality of AAV virions comprising the heterologous nucleic acid sequence to a mammal or a cell of a mammal, thereby delivering or transferring the heterologous polynucleotide sequence into the mammal or cell of the mammal. In some embodiments, the heterologous nucleic acid sequence encodes a protein expressed in the mammal, or where the heterologous nucleic acid sequence encodes an inhibitory sequence or protein that reduces expression of an endogenous protein in the mammal.

By way of example, respecting hemophilia, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than about 5% of normal is needed. With respect to treating such a hemophilic subject, a typical dose is at least $1 \times 10^{10}$ AAV vector genomes (vg) per kilogram (vg/kg) of the weight of the subject, or between about $1 \times 10^{10}$ to about $1 \times 10^{11}$ vg/kg of the weight of the subject, or between about $1 \times 10^{11}$ to about $1 \times 10^{12}$ vg/kg of the weight of the subject, or between about $1 \times 10^{12}$ to about $1 \times 10^{13}$ vg/kg of the weight of the subject, to achieve a desired therapeutic effect.

EXAMPLES

Example 1

Novel Recombinant Adeno-Associated Virus Capsids with Enhanced Human Skeletal Muscle Tropism Purpose:

The goal this study was to evolve new recombinant AAV (rAAV) capsids which have the ability to transduce human skeletal muscle cells at levels greater than existing AAV serotypes to enable therapeutic levels of nucleic acid delivery for muscle gene therapies and intramuscularly-delivered vaccines.

Technical Description:

We utilized wild-type replicating AAV libraries of $1 \times 10^5$ variants via DNA shuffling of ten different parental AAV capsids (AAVs 1, 2, 3b, 4, 5, 6, 8, 9_hu14, avian, bovine). Our AAV capsid libraries selectively replicate in human cells when co-administered with wild-type adenovirus type 5, making primary human skeletal muscle cells excellent tools to allow for selection of capsids with tropism for human muscle. Screens were carried out for six rounds of selection in one of two screens, one being in a pool of primary human skeletal muscle stem cells from six patients, and the other in a pool of human skeletal muscle myotubes derived from stem cells from the same six patients. The top 5 highly selected variants from each screen were sequenced and vectorized into either ssAAV-EF1a-GFP-P2A-FLuc or scAAV-CAG-RLuc expression preparations. These candidates were tested alongside control serotypes that represent the current best of muscle tropism, AAVs 1, 6 and 8. All variant and control AAVs were assessed for human muscle transduction with in vitro, in vivo and ex vivo characterization. The best performing variants for clinical use were identified to be AAV-NP66 (SEQ ID NO: 5) and AAV-NP22 (SEQ ID NO: 3) that have transduction profiles significantly higher than controls in human skeletal muscle explants ex vivo.

AAV Vectors:

Current AAV capsids with some demonstrated tropism to skeletal muscle fibers include: AAV1, AAV6, and AAV8. However, many of these initial tropism and transduction studies were performed in mice and non-human primates, and these results do not necessarily correlate with human tropism and transduction. More importantly, very high levels of transduction are needed for muscle gene therapy trials as there are physical limitations to how much AAV can be delivered in a single intramuscular injection which is further complicated by the fact that injections need to span the length of the muscle to correct defects along the muscle length. If an AAV had superior human skeletal muscle transduction, a lower dose and fewer injections would be needed to achieve therapeutic relevance. Similarly for use as a vaccine delivery tool, high efficiency transduction and stability is needed to achieve robust secretion of antibodies encoded within the AAV to reach therapeutic levels of circulating antibodies in the blood. Our new AAV capsids screened and evolved on human skeletal muscle cells demonstrate significantly improved human skeletal muscle transduction over controls in humanized mice in vivo, in numerous human muscle cell cultures in vitro, and most importantly in human skeletal muscle explants ex vivo.

Example 2

Bioengineered Viral Platform for Human Skeletal Muscle Therapeutics Delivery Paradigms Abstract Skeletal muscle is ideal for vaccine and gene therapy administration as it is easily accessible by intramuscular injection. Indeed, recombinant adeno-associated viral (rAAV) vectors have begun being tested in clinical trials for intramuscular passive vaccination for HIV and influenza. However, greater human muscle transduction is needed for therapeutic efficacy than is possible with existing serotypes. To bioengineer capsids with therapeutic levels of transduction, we utilized a directed evolution approach to screen libraries of shuffled AAV capsids in pools of surgically resected human skeletal muscle cells from five patients. Six rounds of directed evolution were performed in various muscle cell types and evolved variants from each screen were validated against existing serotypes rAAV1, 6 and 8. We found that evolved variants NP22 and NP66 had significantly increased primary human and rhesus skeletal muscle fiber transduction from surgical explants ex vivo, in chimeric humanized mouse muscle in vivo, and in various primary and immortalized myogenic cell lines in vitro. We demonstrated reduced seroreactivity compared to controls against normal human serum from 50 donors. These capsids represent powerful tools for human muscle expression and secretion of therapeutic quantities of antibodies in passive vaccines or transgenes in human muscle gene therapy.

Introduction

Skeletal muscle is the largest internal organ in the human body. Therefore, it represents a desirable platform for expressing and secreting proteins (1) of interest into the general circulation. For example, recombinant adeno-associated virus (rAAV) phase I/II clinical trials for hemophilia B (2) and alpha-1 antitrypsin deficiency (3-6) utilized muscle as a target tissue for expressing secreted factors into the bloodstream. More recently, rAAV has received considerable attention for its proposed and current use in human clinical trials as a delivery vector for passive vaccines against HIV (7-9) and influenza (10-14).

AAV has numerous characteristics that define its desirability as a vaccine and gene therapy vector; most importantly, it has an impressive safety record after demonstrated use in over 162 clinical trials (15). When vectorized, it transduces both dividing and non-dividing cells and shows stable expression in quiescent tissues through unintegrated episomes. Despite the ability of rAAV to transduce a variety of tissues, skeletal muscle has historically been one of the most challenging to transduce at levels sufficient to provide therapeutic expression of delivered products. Indeed, naturally occurring rAAV serotypes (rAAV 1, 2, 6, and 8) have seen limited success clinically for intramuscular delivery of transgene products in gene therapy trials for skeletal muscle disorders (3-6, 16), or for expressing secreted proteins into the bloodstream (2-6). This stemmed from the fact that preclinical modeling with rAAV to determine the best serotypes for transducing target tissues was done in animal models—typically mice—which often recapitulate neither the tissue and cell tropism each rAAV has in humans nor the transduction capabilities which can be expected at treatment.

Importantly, rAAV vectors can be bioengineered to improve upon both the transduction level and cellular tropism achievable with naturally occurring serotypes. Indeed, several studies established multi-serotype capsid shuffling approaches for directed evolution of new AAV serotypes with novel properties (17, 18). Although AAV library generation by various methods is widespread (19), our methodology is unique in that it utilizes replicating AAV throughout the entire selection and evolution process. In contrast to non-replicating AAV screens, selection approaches that use replicating AAV are at an advantage in that receptor binding and uptake are not the only parameters under selection (15, 20). With replicating screens, every step in the intracellular trafficking and expression cascade is under selection, all of which heavily influence the efficiency of cell and species-specific transduction properties of rAAV post-entry. A good example is the difference between rAAV2 and rAAV8, where equal numbers of each virion will enter mouse hepatocytes in the liver, but the transduction efficiency and eventual expression can differ by 10-20 fold (21-24). Additionally, results from recent hemophilia B gene therapy clinical trials in humans clearly demonstrated that current animal modeling data are not always predictive of patient outcomes (22, 25). Interestingly, single capsid mutations have been shown to affect transduction post-entry and even post-uncoating in the nucleus (26). Taken together, these data support the use of replicating AAV screens whenever possible.

Numerous preclinical studies and one ongoing clinical trial have begun piloting the use of existing rAAVs as vectors to deliver antibody expression cassettes in passive vaccine approaches for HIV/SIV (7-9), influenza (10-14), henipavirus (27), and human papilloma virus (28-31). The promise of passive immunoprotection against pathogenic viruses has renewed the interest in obtaining rAAV capsids capable of highly efficient intramuscular delivery. Given the poor human skeletal muscle transduction with existing rAAV serotypes, we sought to bioengineer a clinical candidate that could efficiently transduce human skeletal muscle at levels sufficient to express therapeutic levels of broad-spectrum antibodies for passive vaccine approaches or for muscle gene therapies. Using muscle as a platform for antibody expression, we will bypass the need to produce an endogenous adaptive immune response as with traditional vaccination. To accomplish this goal, we utilized directed evolution by DNA gene shuffling to screen for capsids with high efficiency skeletal muscle transduction in primary human skeletal muscle cells specifically.

Results

Ultra-complex AAV Capsid Library Screening in Primary Human Skeletal Muscle Cells DNA shuffling of capsid proteins begins with families of capsid genes from an array of AAV pseudo-species that are enzymatically shuffled and recombined to create a library of chimeras that can be cloned into an AAV shuttle vector to produce live replicating viral libraries (FIG. 1A). We constructed a diverse library from 10 different parental serotypes (1-6, 8, 9_hu14, avian, bovine). To maximize the likelihood that our eventual shuffled capsids could functionally transduce human skeletal muscle—as compared to those from model organisms typically used for pre-clinical evaluation—we performed two simultaneous screens in both primary human skeletal muscle stem cells (hMuSCs) and human muscle myotubes. Surgical skeletal muscle specimens from five patients were digested and fluorescence-activated cell sorting (FACS) was used to isolate a defined hMuSC population that was $CD31^-CD34^-CD45^-EGFR^+ITGB1^+$(32) (FIG. 1B). This hMuSC population can be maintained in an undifferentiated and proliferative state (FIG. 1C), or can be differentiated in short-term cultures to produce human myotubes (32). These cell types were separately pooled at equal ratios from five patient explants to maximize cellular/patient variation for screening. Replicating screens (FIG. 1D) were carried out for six rounds of selection (FIG. 1E) with diversity monitoring via Sanger sequencing until the end of the screens when selection pressure plateaued (FIG. 6A, B).

Figures 7A, 7B:
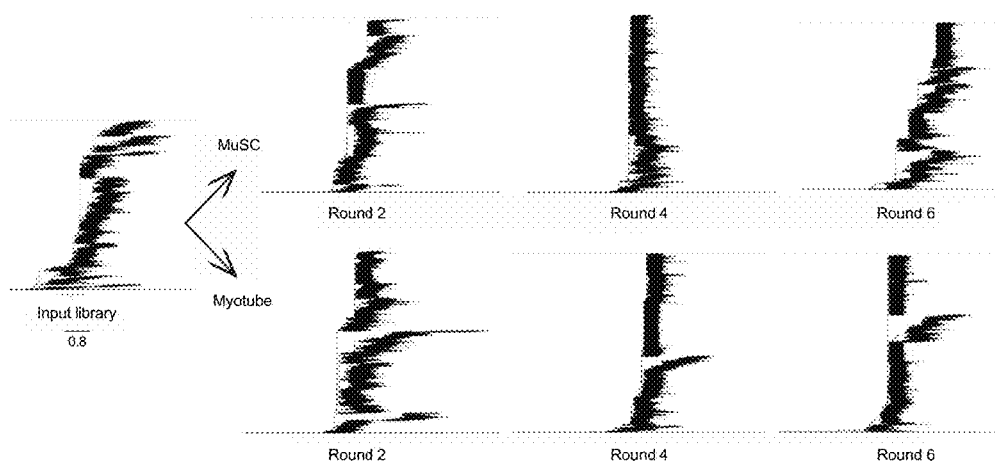
FIG. 7A-FIG. 7B shows round-by-round phylogenetic trees of all variants by PacBio long-range sequencing. (A) Comparative phylogenies showing genetic relatedness at the amino acid level among the parental serotypes in the library and all library variants. The decreasing diversity and increasing enrichment going from the unselected AAV library through rounds 2, 4 and 6 for each screen (human MuSC and myotube) are shown. (B) Raw and filtered CCS read counts used to generate panel (A) are shown.

Structural and Computational Modeling Identify Key Functional Motifs from Parental Serotypes At the completion of both screens, the input library and every other round from each screen were deep sequenced using PacBio long-range sequencing. Round-to-round positional analyses for each screen identified selection of key residues as the screens progressed (FIG. 2), and was far more informative than traditional phylogenetic representations that root the tree on the nearest full-length parental sequence, thereby masking functionally important residues within full-length capsid relatedness (FIG. 7). For example, although AAV2 was the most highly represented parental sequence in the input library, evolved chimeras rapidly converged on non-AAV2 amino acids within just 2 rounds of screening. In the myotube screen, rapid selection occurred for the unique region of VP1 converging on AAV8, as well as the unique region of VP2 and nearly all of AAP from AAV1. VP3 selection heavily favored N-terminal AAV1 contributions, followed by AAV3b, then AAV8 and lastly AAV2 at the C-terminal end. The muscle stem cell screen displayed a different pattern wherein the unique region of VP1 is nearly all AAV1, even as early as round 2. Much of the VP2 and VP3 parental contributions are similar to the myotube variants. An exception occurred in the C-terminal end of VP3 that showed enrichment for AAV8 rather than AAV2 sequences.

Several of the most highly selected variants from each screen were isolated and vectorized with *Renilla* and Firefly Luciferase (RLuc/FLuc) expression constructs for subsequent validation experiments. To assess the genetic contribution of each parental AAV serotype to individual evolved capsids selected from each screen, we performed fragment crossover mapping (FIG. 3A) and predictive fragment conservation analyses (FIG. 6C) to calculate enrichment scores for the likelihood of parental contribution to shuffled fragments in the new capsids. These complementary methodologies demonstrated that diverse shuffling was achieved and maintained along the length of Cap, including VP1, VP2, VP3 and AAP. The parental serotypes that contributed most to the evolved variants included AAV1, 2, 3b, 6, 8 and 9_hu14. No variants had appreciable capsid fragment regions from AAV4, 5, bovine or avian. Three-dimensional structural capsid mapping of shuffled variants (FIG. 3B) revealed both diverse structural meta-heterogeneity in hypervariable regions but also micro-conservation within key structural domains such as the cylinder, canyon and various symmetry axes.

Figure 4A:
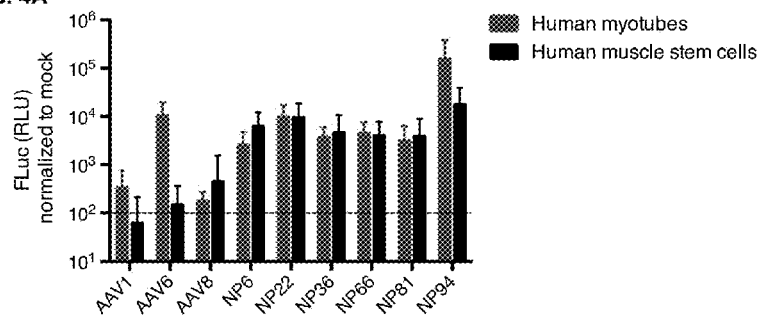
FIG. 4A-FIG. 4C provides in vitro validation of superior muscle transduction and seroreactivity. (A) Transduction assessments by FLuc expression of the best performing vectorized variants in primary human muscle stem cells (black) and human myotubes (red) compared to known muscle-tropic control rAAV serotypes 1, 6 and 8. Each cell type was assayed in three separate experiments, each performed in technical duplicate or triplicate (n=6-9 for each bar). Dotted line represents limit of detection in relative luminescence units (RLU) as determined by standard dilutions. Data represent mean±SD. (B) Transduction assessments by FLuc expression of best performing vectorized variants in normal mouse myoblasts (red) and dystrophic $Mdx^{5cv}$ mouse myoblasts (black) compared to control rAAV serotypes 1, 6 and 8. Each cell type was assayed in three separate experiments, each performed in technical duplicate or triplicate (n=6-9 for each bar). (C) Seroreactivity ELISA assay for presence of anti-AAV antibodies in normal human serum from 50 US adults. Each individual patient was assayed in technical triplicates with data points representing the mean minus background for each patient.

Enhanced Muscle Cell Transduction and Immunologic Properties of Bioengineered Variants Large-scale ultrapure productions of all vectorized variants were carried out and those capable of producing high titers sufficient for eventual clinical use (variants NP6, NP22, NP36, NP66, NP81 and NP94) were considered further for validation. We began with FLuc transduction efficiency assessments in vitro in primary hMuSCs and human myotubes, as well as mouse myoblasts from wildtype and dystrophic $Mdx^{5cv}$ mice with comparisons to known muscle-tropic rAAV serotypes 1, 6 and 8. In pooled primary hMuSCs isolated from five patients (FIG. 4A), all six shuffled variants showed significantly increased functional transduction that ranged from a 62 to 284-fold improvement over rAAV1 (p<0.05), a 26 to 118-fold improvement over rAAV6 (p<0.05), and variants NP6, NP22, NP66 and NP94 showed a 10 to 45-fold improvement over rAAV8 (p<0.03). Variants NP36 and NP81 showed a 9-fold improvement in transduction over rAAV8 but did not reach statistical significance. In pooled human myotube cultures differentiated from primary hMuSCs (FIG. 4A), all six shuffled variants showed significantly increased functional transduction that ranged from a 7 to 464-fold improvement over rAAV1 (p<0.01), a 14 to 871-fold improvement over rAAV8 (p<0.02), and NP94 showed a 15-fold improvement over rAAV6 but did not reach statistical significance.

Figure 4B:
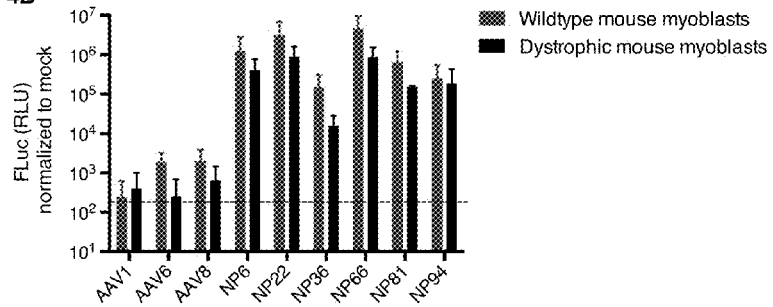

In C2C12 mouse myoblasts (FIG. 4B), all shuffled variants showed highly significant increased functional transduction that ranged from a 610 to 18,730-fold improvement over rAAV1 (p<0.02), an 80 to 2,451-fold improvement over rAAV6 (p<0.02), and a 73 to 2,237-fold improvement over rAAV8 (p<0.02). Similarly, in dystrophic mouse myoblasts from $Mdx^{5cv}$ mice (FIG. 4A), all shuffled variants showed significant increased functional transduction that ranged from a 39 to 2,174-fold improvement over rAAV1 (p<0.03), a 63 to 3,479-fold improvement over rAAV6 (p<0.04), and a 25 to 1,390-fold improvement over rAAV8 (p<0.03). Each of the four cell types used for in vitro transduction tests was assayed in three separate experimental replicates and each of those performed in technical duplicate or triplicate. Importantly, results from these four different muscle lines highlighted the striking differences in transduction levels that can be seen in different species, different cell types, different disease states, and primary versus immortalized cell lines.

Figure 4C:
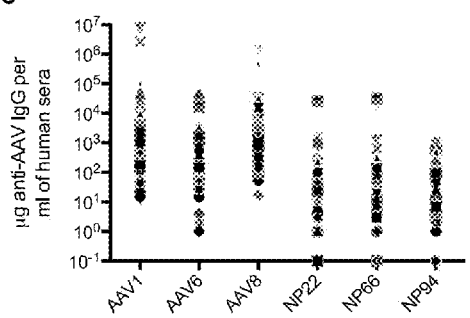
Figure 8A:
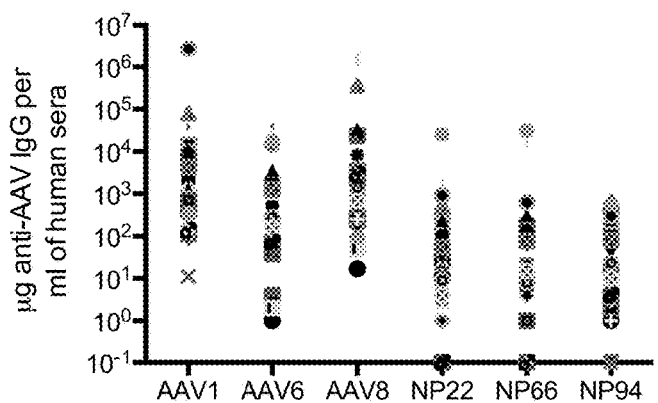
FIG. 8A-FIG. 8C shows seroreactivity profiling by gender and neutralization assays. Seroreactivity ELISA assay for presence of anti-AAV antibodies in normal human serum from 50 US adults. (A) Male patients. (B) Female patients. Each patient was assayed in technical triplicates with data points representing the mean minus background. (C) Pooled primary human myotube cultures from five patients were used to assess rAAV neutralization in the presence of increasing concentrations of pooled human immunoglobulins (IVIG mg/mL). Each rAAV variant was normalized to its own 'no IVIG' FLuc expression control sample.
Figure 8B:
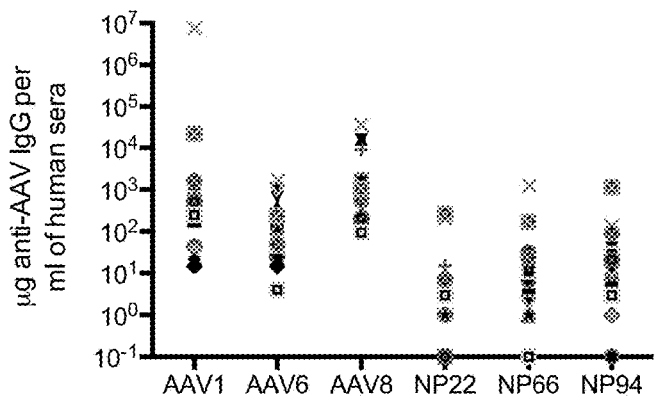
Figure 8C:
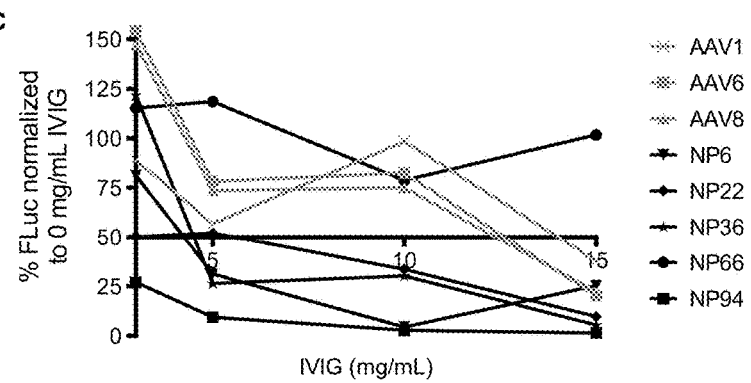

An advantage of the in vitro systems for characterization is the ability to perform binding seroreactivity assays as well as titered neutralization assays to predict the likelihood of humoral neutralization by patients with pre-existing cross-reacting anti-AAV capsid antibodies. Individual human serum samples from 50 healthy adults of each gender and varied ethnicities (see FIG. 11 for details) were assessed for seroreactivity by indirect ELISA against the best performing capsid variants from the in vitro transduction assays and control serotypes (FIG. 4C, 8A, 8B). All three shuffled variants—NP22, NP66 and NP94—had greatly reduced seroreactivity compared to all 3 muscle-tropic controls rAAV1, 6 and 8. Neutralization assays demonstrated that NP66 was the most resistant capsid to neutralization when assessed on pools of primary human myotube cultures from five patients for transduction in the presence of increasing levels of pooled human immunoglobulins (FIG. 8C). In summary, based on the superior seroreactivity, neutralization and in vitro transduction results from shuffled variants NP22, NP66, NP94 and control AAV6, we decided to move forward with these four capsid serotypes for additional, more stringent, preclinical validation.

Figure 5A:
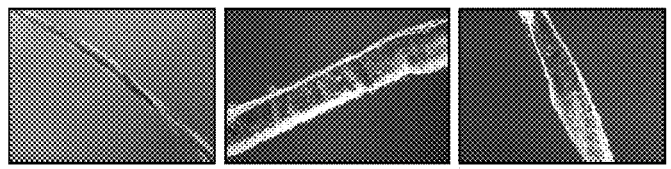
FIG. 5A-FIG. 5K shows validation of human and non-human primate primary skeletal muscle transduction ex vivo. (A) Representative brightfield images of primary human skeletal muscle fibers used in B-K. Magnifications were 10× and 20×. (B) RLuc imaging at 48-hrs of human female p. major fibers transduced ex vivo with PBS, rAAV6, NP22, NP66 or NP94 expressing scAAV-CAG-RLuc. Mean radiance (p/s/cm$^2$/sr) is displayed below each treatment triplicate. (C) RLuc assay on lysed p. major fibers at 48-hrs. Data represent mean±SD. p<0.005=; p<0.0001=, as determined by Student's unpaired two-tailed t-test assuming equal variance. (D) RLuc imaging at 48-hrs of human male l. dorsi fibers transduced with same conditions as B. (E) RLuc assay on lysed l. dorsi fibers at 48-hrs. Data represent mean±SD. p<0.0001=**. (F) RLuc imaging at 48-hrs of rhesus b. femoris fibers transduced with same conditions as B. (G) RLuc assay on lysed b. femoris fibers at 48-hrs. Data represent mean±SD. p<0.02=*; p<0.0002=***. (H) RLuc imaging at 48-hrs on 1 replicate (due to small sample size) of human r. abdominis muscle fibers transduced with same conditions as B. (I) RLuc assay on lysed r. abdominis fibers 48-hrs post-transduction. (J) RLuc imaging on 1 replicate of human l. dorsi fibers transduced with same conditions as B. (K) RLuc assay on lysed l. dorsi fibers 48-hrs post-transduction.
Figure 5B:
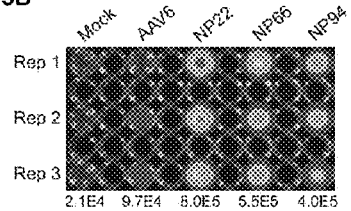
Figure 5C:
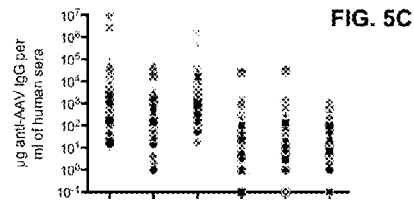

Humanized Muscle Xenografts are Surrogates for Assessing Muscle Transduction in Human Cells In Vivo To more rigorously assess the human skeletal muscle transduction capabilities of our chosen shuffled and control AAV capsids in an in vivo setting, we characterized our variants in a chimeric humanized muscle mouse xenograft model (32). Primary hMuSCs from five patients were pooled at equal ratios and transplanted by direct intramuscular injection into the hind limbs of pre-injured recipient immune-deficient NSG mice. Upon transplantation, the hMuSCs fuse with host myofibers of the mouse, generating chimeric, multi-nucleated myofibers containing both mouse and human nuclei (32). Large cohorts of xenografted NSG mice and gender-matched non-transplanted control NSG mice were produced and administered shuffled or control rAAV variants expressing FLuc by direct intramuscular injection (1E9/leg) and assessed weekly for transduction in time-course studies over two months via non-invasive luciferase live imaging (33) (FIG. 5A-C). Control rAAV6 was the first vector to uncoat and express but variant NP66 rapidly followed and produced the highest sustained transduction levels in xenografted mice, rather than the decreasing expression over time seen with rAAV6. Strikingly, rAAV6 outperformed the shuffled variants when no human muscle fibers were present, further highlighting the importance of performing preclinical studies in human cells and human xenograft systems whenever possible to prevent misleading results which are mouse-specific.

Enhanced Human Skeletal Muscle Explant Transduction by Evolved Variants Ex Vivo

Figure 5D:
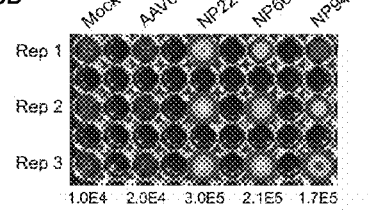
Figure 5E:
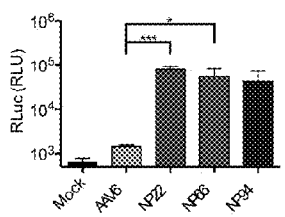
Figure 5F:
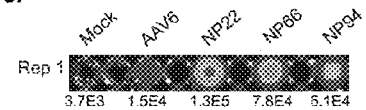
Figure 5G:
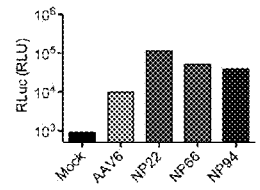
Figure 5H:
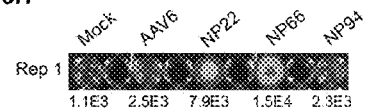
Figure 5I:
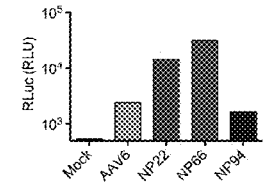

While chimeric humanized muscle xenograft mice are powerful tools to model human-like in vivo systems, they are limited in their ability to truly define expected transduction in human patients given the continued presence of mouse cells, as well as the chimeric nature of the fusion product fibers which express both mouse and human proteins simultaneously in syncytia. To overcome these limitations and more accurately predict eventual muscle transduction in human patients, we sought to transduce human skeletal muscle fiber explants from surgical resections ex vivo. Skeletal muscle fibers (FIG. 9A) from four adult patients (two male and two female) were used for ex vivo explant transduction assessments. Initial transduction analyses began with our 3 top performing variants NP22, NP66 and NP94 compared to the best muscle-tropic control serotype rAAV6. Skeletal muscle resections were digested and individual muscle fibers were isolated within 1-hr of removal from each patient for 48-hr culture and transduction comparisons with scAAV-CAG-RLuc (3E8 vg/well) on 300 fibers per condition. Human patient-1 was a 61-year-old female from whom fibers of pectoralis major muscle were excised and transduced in triplicate. By live fiber luciferase imaging 48-hr post-administration (FIG. 5B), variants NP22, NP66 and NP94 all showed significantly increased transduction over rAAV6 controls. To more accurately quantify the increased transduction, given the dense cellular structure of muscle fibers, luciferase assays were also performed on lysed muscle fibers (FIG. 5C). Compared to rAAV6 controls, variants NP22 ($p<0.0001$), NP66 ($p<0.001$) and NP94 ($p<0.005$) showed significantly increased human skeletal muscle fiber transduction that ranged from a 5 to 14-fold average increase. Two additional patients of each gender and with varied muscle groups were used to confirm the results seen from the initial patient: patient-2 was a 58-year-old female and patient-3 was a 60-year-old male from whom fibers from the rectus abdominis and latissimus dorsi muscles, respectively, were excised and transduced (FIG. 5F-1). Despite differences in their gender and muscle type, both patients again demonstrated a significant 4 to 13-fold improvement in transduction with our shuffled variants NP22, NP66 and NP94 over rAAV6 by live fiber imaging and luciferase assays on lysed muscle fibers.

To further characterize the efficiency of the newly evolved variants, we performed the same sets of transduction experiments in a fourth human sample and compared to all muscle-tropic serotypes, rAAV1, rAAV6 and rAAV8. Patient-4 was a 71-year-old male from whom fibers from the latissimus dorsi muscle were excised and transduced as before. Here again, all three shuffled variants demonstrated significantly increased transduction by live fiber imaging (FIG. 5D), as well as luciferase assays on lysed fibers (FIG. 5E), over all three control serotypes ($p<0.0001$). More specifically, NP22 demonstrated an 84-fold increase over AAV8, a 45-fold increase over AAV6 and a 25-fold increase over AAV1. NP66 demonstrated a 26-fold increase over AAV8, a 14-fold increase over AAV6 and an 8-fold increase over AAV1. Finally, NP94 demonstrated a 14-fold increase over AAV8, an 8-fold increase over AAV6 and a 4-fold increase over AAV1. Individual muscle fiber staining revealed AAV uptake along the entire length of the fiber (FIG. 9D).

Figure 5J:
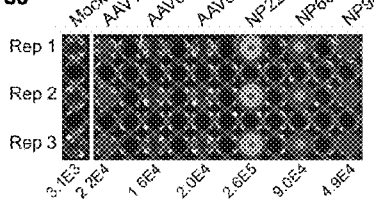
Figure 5K:
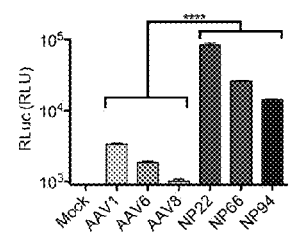

Rhesus Skeletal Muscle Explant Transductions Support the Use of NP22 and NP66 for preclinical Vaccine Testing Given the superior tropism and transduction capabilities of shuffled variants NP22, NP66 and NP94 in human skeletal muscle settings in vitro, in vivo and ex vivo, the next step in moving these variants to the clinic for use as vaccine vectors would be to determine efficacy in prophylactic experiments in non-human primates. To justify preclinical testing in non-human primates, we asked whether the same enhanced transduction observed in human skeletal muscle tissues could be reproduced in muscle from rhesus macaques. Mimicking our ex vivo transduction studies from four human patients, we surgically resected live biceps femoris skeletal muscle explants from a healthy 20-year-old male rhesus macaque. The skeletal muscle tissue (FIG. 9E) was digested and individual muscle fibers were isolated for administration of scAAV-CAG-RLuc within 1-hr of surgical excision followed by 48-hr culture. Again, variants NP22 ($p<0.0002$) and NP66 ($p<0.02$) showed highly a significant 30 to 57-fold improvement in transduction over rAAV6 by live fiber luciferase imaging (FIG. 5J) and luciferase assays on lysed fibers (FIG. 5K).

Discussion

Muscle is increasingly being recognized as a key secretory organ (1) and is among the most easily accessible tissues for localized vector administration. Therefore, muscle represents an ideal tissue platform for expression of desired therapeutic factors, including either neutralizing antibodies or proteins deficient in muscle disorders. Indeed, an ideal HIV vaccine would be administered intramuscularly in an EpiPen-style auto-injection format. This would bypass the need for intravenous administration by healthcare professionals in hospitals, and instead allow for administration in the field. Patients, particularly in developing countries where the need for an effective HIV vaccine is greatest, could administer their own vaccine at distribution centers. An added advantage to rAAV as a vaccine delivery modality is the remarkable heat-tolerance rAAV capsids display, with thermal stability up to 85° C. for some serotypes (34), allowing for potentially minimal refrigeration needs. Additionally, studies have demonstrated that rAAV can effectively be desiccated or lyophilized and later resuspended (35), offering additional ways to maintain stability and further reduce the cost of vaccine shipments to the developing world.

An exciting possibility with our new capsid variants that transduce human skeletal muscle at such high levels would be to decrease patient doses while still enabling therapeutic levels of antibody or transgene expression. This could bypass several hurdles to rAAV being an effective passive vaccine delivery tool or vector for future muscle gene therapy trials: a) reduced potential for the generation of anti-antibody responses to rAAV-delivered antibodies like those shown for anti-HIV and anti-SIV broadly neutralizing antibodies (36); b) decreased likelihood for neutralizing anti-capsid antibody binding (37, 38) since fewer circulating rAAV capsids would be present; c) reduced cost of production per patient as current treatments have ballooned to over $1 million dollars per patient (39, 40); and d) reduced probability for capsid-specific T cell responses against transduced muscle fibers (37). In addition, given the highly favorable seroreactivity profiles of all three variants—NP22, NP66 and NP94—greater numbers of patients may be eligible to receive treatment than compared to control serotypes. This correlates well with neutralization where NP66 was also superior at evading neutralization in muscle cells among all other shuffled variants, and indeed is missing two highly antigenic residues (V708 (41) and N717 (42)) present on rAAV1 and 6, known muscle tropic parents under consideration for use in passive vaccines and currently used for muscle gene therapies. For perspective, rAAV1 is second only to rAAV2 in terms of pre-existing neutralizing antibodies (35-70% vs. 60-70%) in the human population, and rAAV6 is close behind at ~50% (43, 44).

In addition to use in passive vaccines administered intramuscularly, the significantly increased transduction of both dividing (myoblasts) and non-dividing (myotubes and myofibers) human skeletal muscle cell types make our new capsids uniquely suited for use in future gene therapy clinical trials treating genetic diseases of muscle such as dystrophinopathies like Duchenne muscular dystrophy (16), and sarcoglycanopathies (45) via gene transfer. Further, the muscle gene-editing field could benefit immensely from use of these new rAAV capsids given the already promising results delivering CRISPR/Cas9 systems to perform in vivo gene editing for dystrophinopathies with existing serotypes (46-48).

Shuffled NP22, NP66 and NP94 capsid sequences (FIG. 10) have many fragments from rAAV1, 6 and 8 parental sequences that have known muscle tropism, likely explaining why these variants were selected for so strongly in the muscle cell screens. Yet, each of these 3 shuffled capsids would be predicted to have highly unique comparative structures to one another given their divergent capsid sequence arrangements. NP22 is the most highly shuffled of the three, with the unique region of VP1 coming from rAAV3b and 8, the unique region of VP2 coming from rAAV8, 3b and 6, and finally VP3 with contributions from rAAV9_hu14, 3b, 8 and 2 as well as de novo mutations. NP66 is the least shuffled of the three, with the unique region of VP1 and VP2 coming solely from rAAV1, and a VP3 composed largely of AAV8 and 2 and several de novo mutations. NP94 has a rAAV8-based unique region of VP1, a unique region of VP2 entirely from rAAV1, and a mixed VP3 with contributions from rAAV1, 3b, 2 and 8. These diverse shuffled capsid arrangements likely play a role in the reduced seroreactivity our shuffled variants have over control serotypes.

Cumulatively, our results show the significantly increased human skeletal muscle transduction of shuffled AAV variants NP22, NP66 (and in some cases NP94) over control serotypes when assessed in various primary human muscle cell types in vitro, in human muscle xenografted mice in vivo, and both human and non-human primate skeletal muscle resections ex vivo. Our work demonstrated the value of utilizing human cells and human xenograft systems whenever possible for both screens and transduction validation studies given the striking differences in transduction demonstrated in vitro and in vivo between mouse and human muscle tissues.

Methods

Shuffled AAV capsid plasmid library generation. The shuffled AAV capsid library was generated as described (49) with minimal variations. The AAV capsid gene from serotypes 1, 2, 3b, 4, 5, 6, 8, 9_hu14, avian and bovine were PCR-amplified with Phusion High-Fidelity DNA Polymerase (NEB Cat#M0530) and cloned using a Zero Blunt TOPO PCR Cloning Kit (Invitrogen Cat#K2800) followed by Sanger sequencing of individual clones. Capsid genes were excised, mixed at 1:1 ratios and digested using DNaseI at various intervals from 1-30 min. These pooled reactions were separated on 1% (w/v) agarose gel, and fragments <1,000-bp were excised and used in a primer-less PCR reassembly step, followed by a second round of PCR including primers binding outside the capsid gene:

```
Fwd:
                        (SEQ ID NO: 15)
5'-GTCTGAGTGACTAGCATTCG-3'/

Rev:
                        (SEQ ID NO: 16)
5'-GCTTACTGAAGCTCACTGAG-3'
```

Full length shuffled capsid genes were cloned into a pAAV2 host plasmid. Ligations were transformed into numerous independent electro-competent cell aliquots and diluted 1:40 in LB culture with minimal ampicillin (50 g/mL) for minimal expansion. An aliquot was plated, and one hundred clones were picked and Sanger sequenced to validate library diversity. The pool of library plasmids was purified using an EndoFree Plasmid Mega Kit (Qiagen Cat#123811) and used to produce libraries of replication-competent AAV capsids.

AAV library production, vector production and titration. AAV library productions were produced using a $Ca_3(PO_4)_2$ transfection protocol (wtAAV library plasmid pool and pAd5 helper) in HEK293T cells (ATCC Cat#CRL-3216) followed by double cesium chloride density gradient purification and dialysis as previously described (50). AAV libraries were titered for Rep by TaqMan qPCR with the following primer/probe set:

```
Fwd:
                        (SEQ ID NO: 17)
5'-TTCGATCAACTACGCAGACAG-3'/

Rev:
                        (SEQ ID NO: 18)
5'-GTCCGTGAGTGAAGCAGATATT-3'

Probe:
                        (SEQ ID NO: 19)
5'/FAM/TCTGATGCTGTTTCCCTGCAGACA/BHQ-1/-3'
```

Recombinant AAV vector productions expressing Firefly (FLuc) or *Renilla* Luciferase (RLuc) were similarly produced as above but as triple transfections with pAd5 helper, AAV transfer vector (either ssAAV-EF1α-GFP-P2A-FLuc or scAAV-CAG-RLuc), and pseudotyping plasmids for each capsid of interest. The new scAAV-CAG-RLuc transfer vector was deposited to AddGene (ID 83280). AAV vectors were titered by TaqMan qPCR. The ssAAV-EF1α-GFP-P2A-FLuc vectors were titered on GFP with the following primer/probe set:

```
Fwd:
                                        (SEQ ID NO: 20)
5'-GACGTAAACGGCCACAAGTT-3'/

Rev:
                                        (SEQ ID NO: 21)
5'-GAACTTCAGGGTCAGCTTGC-3'

Probe:
                                        (SEQ ID NO: 30)
5'/FAM/CGAGGGCGATGCCACCTACG/BHQ-1/-3'
```

The scAAV-CAG-RLuc vectors were titered on CAG with the following primer/probe set:

```
Fwd:
                                        (SEQ ID NO: 22)
5'-GTTACTCCCACAGGTGAGC-3'/

Rev:
                                        (SEQ ID NO: 23)
5'-AGAAACAAGCCGTCATTAAACC-3'

Probe:
                                        (SEQ ID NO: 24)
5'/FAM/CTTCTCCTCCGGGCTGTAATTAGC/BHQ-1/-3'
```

Human skeletal muscle isolation from surgical specimens. Human skeletal muscle specimens from both male and female patients were surgically isolated from latissimus dorsi, *serratus* anterior, pectoralis major or *rectus abdominis* intraoperatively in accordance with the Stanford Institutional Review Board (IRB#15084). Muscle tissue was wrapped in sterile gauze and placed immediately on ice after isolation. Tissue processing for stem cell isolation or muscle fiber isolation always began within 1-hr of surgical excision.

Surgical non-human primate skeletal muscle isolation. Rhesus macaque skeletal muscle specimens from the biceps femoris were surgically isolated by the Stanford University Veterinary Pathology team in accordance with the Stanford Institutional Animal Care and Use Committee. Tissue was placed immediately in Collagenase-II after isolation and tissue processing for fiber isolation began within 1-hr of surgical excision.

Human skeletal muscle stem cell isolation and purification. Human skeletal muscle tissue was prepared as described (32) for the isolation of pure populations of stem cells by FACS with the surface marker profile CD31$^-$CD34$^-$CD45$^-$EGFR$^+$ITGB1$^+$(51). Sorted cells were assessed immediately post-sorting for adherence and viability as controls for sorting efficiency. In addition, a fraction of the sorted cells were routinely plated and stained for PAX7 to demonstrate purity of the sorted stem cell population as previously described (32).

Human skeletal muscle stem cell and myotube cultures. Plates were coated with extracellular matrix protein at 1:500 (V:V) in DMEM with 1% penicillin/streptomycin. The hMuSC medium was a 1:1 mixture of DMEM:MCDB medias supplemented with 20% FBS, 1% insulin-transferrin-selenium, 1% antibiotic/antimycotic, and 10-µM p38i (Cell Signaling Technology Cat#SB203580) to maintain the stem state, as described (32). Media for differentiating primary hMuSCs into myotubes lacked p38i and included a 2% horse serum starve instead of 20% FBS for 7-days. Immunofluorescence analysis of cultured hMuSCs was performed as described (32). All media was changed every two days.

Mouse skeletal muscle myoblast cultures. Wild-type C2C12 mouse myoblasts (ATCC Cat#CRL-1772) were maintained in DMEM supplemented with 10% FBS and 1% antibiotic/antimycotic. Dystrophic mouse myoblasts (Mdx$^{5cv}$) were maintained in Nutrient mixture F10 supplemented with 20% FBS, 1% antibiotic/antimycotic and 2.5 ng/ml recombinant human FGF on the same ECM-coated plates as the human cultures to improve adherence.

Animals. Adult NOD/SCID/IL2 receptor gamma chain (NSG) deficient female mice (NOD.Cg-Prkdc$^{scid}$Il2rg$^{tm1Wjl}$/SzJ, stock#005557) were obtained from The Jackson Laboratory. Mice were housed and maintained in the Stanford Institute of Medicine Barrier Facility. Skeletal muscle from a healthy, 20-year-old, 14.5-kg, intact male rhesus macaque (*Macaca mulatta*) was harvested immediately following humane euthanasia during an end-of-study time point.

Human muscle stem cell transplantation to generate chimeric muscles in mice. The tibialis anterior muscle of recipient NSG mice was pre-injured with a 50-µL direct intramuscular injection of 1.2% barium chloride (in PBS) 48-hr prior to transplantation as described (52). Cultured human muscle stem cells were released with Accutase at 25° C. and then counted, centrifuged, and resuspended in PBS for transplantation of 600K cells in a total volume of 60-µL per leg. Cell suspensions were kept on ice prior to transplantation. Cells were loaded into 100-µL Hamilton or micro-insulin syringes equipped with 30-gauge needles. After incising the skin overlying the anterior lower hind limb, cells were direct-injected into the tibialis anterior muscle via multiple injections down the length of the muscle, as previously described (32).

Immunohistochemical analysis of human engraftment and viral transduction in mouse muscles. Tibialis anterior muscles from xenografted or control mice were dissected, fixed for 4-hr in 4% PFA (in PBS) and rehydrated through a 5-30% sucrose series in PBS for 24-hr before freezing in OCT over a liquid nitrogen cooled isopentane bath. Muscle cross-sections were cut at 7-microns, collected onto Superfrost Plus glass slides and frozen until stained. After rehydrating with PBS, sections were permeabilized with 0.3% Triton X-100 for 10-min and washed with PBS. Sections were blocked for 1-hr in 10% goat serum in PBS with mouse-on-mouse blocking reagent (Vector Laboratories Cat#MKB-2213) according to manufacturer's instructions. Blocking solution was washed away with PBS and sections were incubated overnight with primary antibodies in PBS-T at 4° C. Sections were washed with PBS-T and incubated with secondary antibodies and Hoechst 33342 (1:1,000 V:V), for 1-hr at room temperature in PBS-T. Slides were washed with PBS and mounted with ProLong Gold Antifade under #1.5 coverslips. Primary antibodies used for staining sections: rat anti-laminin-2 monoclonal IgG (detecting human and mouse; clone 4H8-2; Abcam Cat#11576; 1:3,000 V:V), rabbit anti-GFP polyclonal IgG (Abcam Cat#6556; 1:500 V:V), and mouse anti-integrin beta-1 monoclonal IgG (human-specific; clone TS2/16; BioLegend Cat#303008; 1:100 V:V) conjugated to APC. Primary antibodies were detected with goat secondary antibodies recognizing rat (Invitrogen Cat#A-11007) or rabbit (Invitrogen Cat#A-11034) conjugated to Alexa Fluor dyes at 1:400 V:V. Confocal imaging was performed on a Leica TCS SP8-X WLL inverted confocal microscope with a 20× oil immersion objective and imaged with Leica AF software v3.3.0.10134. White light laser power was kept constant at: 405 nm 30%, 488 nm 9%, 594 nm 5% and 647 nm 10% for all images. Z-stacks were compressed using ImageJ v2.0.0 and overlaid in Adobe Photoshop CS6 v13.0.

Replication-competent shuffled AAV capsid library selection. Pooled human muscle stem cells from 5 patients (2-3E6 cells) or differentiated myotubes were initially transduced with 1E11 vg (MOI 20K for round 1) of AAV library in 20-mL media in 15-cm dishes. 5E8 PFU wild-type replication competent human Adenovirus-5 (hAd5) (in 500-μL volume, ATCC Cat#VR-5) was added to media 2-hr later. The media was changed 12-hours later after 3 dPBS washes. Cells were harvested 48-hr after hAd5 administration. Each sample was mixed with 1-mL of PBS and underwent three freeze—thaw cycles to ensure complete cell lysis, followed by hAd5 heat inactivation (65° C. for 30-min), and 5-min spin at 14,000×G at 4° C. This supernatant (~800-μl per round, MOI 1-5K) was then used for subsequent in vitro selection steps and PCR analysis. For PCR analysis, 20-μL of supernatant was used for AAV gDNA extraction using the MinElute Virus Spin Kit (Qiagen Cat#57704), followed by PCR amplification using:

```
Fwd:
                                         (SEQ ID NO: 25)
5'-TGGATGACTGCATCTTTGAA-3'/

Rev:
                                         (SEQ ID NO: 26)
5'-ATGGAAACTAGATAAGAAAGAA-3'
```

PCR to assess AAV amplification at each round was performed using Phusion high-fidelity polymerase and the following program: 98° C. 2-min, 30 cycles of 98° C. 20-sec, 55° C. 15-sec, 72° C. 1-min. AAV capsid ORFs from rounds 3-6 of the selection screens were cloned using a Zero Blunt TOPO Kit and 100 clones were sent for full Sanger sequencing to assess remaining library diversity with primers:

```
Fwd-1:
                                         (SEQ ID NO: 25)
5'-TGGATGACTGCATCTTTGAA-3'/

Fwd-2:
                                         (SEQ ID NO: 27)
5'-ATTGGCATTGCGATTCC-3'

Rev-1:
                                         (SEQ ID NO: 26)
5'-ATGGAAACTAGATAAGAAAGAA-3'
```

Vectorization and sequence contribution analysis of evolved AAV capsids. Contigs were assembled using Geneious R7 v7.1.9 software and clones selected for vectorization were PCR-amplified using:

```
Fwd
                                         (SEQ ID NO: 28)
5'-AAATCAGGTATGGCTGCCGATG-3'/

Rev:
                                         (SEQ ID NO: 29)
5'-AACGCCCGGGCTGTAGTTAATGATTAAGCCGCCATGCTACTTATC
TACGTAGCCATGGAAACTAGATAAGAAAG-3'
```

PCR amplicons were cloned using a Zero Blunt TOPO kit, sequence verified, released with enzyme digestion and cloned in-frame downstream of Rep into predigested recipient pCap packaging plasmid containing AAV2 Rep without ITRs using SwaI and XmaO restriction sites. AAV capsid genes were sequence verified and resultant contigs were analyzed using a custom Perl pipeline that assessed multiple sequence alignments using Clustal Omega (EMBL-EBI) to generate the overall serotype composition of the shuffled AAVs by comparison of DNA and amino acid sequences with the parental AAV serotypes based on maximum likelihood. Xover 3.0 DNA/protein shuffling pattern analysis software was used to generate parental fragment crossover maps of shuffled variants (53). Each parental serotype was color coded as follows: AAV1: red; AAV2: forest green; AAV3b: marine blue; AAV4: magenta; AAV5: tv blue; AAV6: green cyan; AAV8: orange; AAV9: pale green; bovine: purple; avian: deep salmon).

PacBio library preparation and long-Range sequencing. PacBio SMRT bell libraries were prepared following the "Procedure and Checklist-2 kb Template Preparation and Sequencing" protocol from PacBio using the SMRTbell Template Prep Kit v1.0 (Cat#100-259-100). PacBio 'Binding and Annealing' calculator determined appropriate concentrations for annealing and binding of SMRTbell libraries. SMRTbell libraries were annealed and bound to the P6 DNA polymerase for sequencing using the DNA/Polymerase Binding Kit P6 v2.0 (Cat#100-372-700). Bound SMRTbell libraries were loaded onto SMRT cells using standard MagBead protocols and the MagBead Buffer Kit v2.0 (Cat#100-642-800). The standard MagBead sequencing protocol is followed with the DNA Sequencing Kit 4.0 v2 (Cat#100-612-400, also known as P6/C4 chemistry). Sequencing data was collected for 6-hour movie times with 'Stage Start' not enabled. Circular consensus sequence (CCS) reads were generated using the PacBio SMRT portal and the RS_ReadsOfInsert.1 protocol, with filtering set at Minimum Full Pass=3 and Minimum Predicted Accuracy=95.

Bioinformatic assessment of PacBio sequences. CCS reads with sequence lengths from 2300-2350 bp were included in downstream bioinformatics analyses. Indels in CCS reads were corrected using an in-house algorithm that first assesses parental fragment identity to determine correct parental nucleotide sequences to compare for determining indels for correction. Single nucleotide polymorphisms that did not result in indels, were maintained. Corrected sequences in FASTA format were then aligned with MUSCLE (54). Phylogenetic analysis was conducted using the maximum-likelihood method in RAxML (55). Percent parental conservation was determined using an in-house algorithm that identifies the percentage of each parent on each aligned position in the shuffled library.

In vitro transduction analysis in human muscle stem cells, human myotubes and mouse myoblasts. 18K cells of each type were plated in 48-well coated plates in 500-μL of respective maintenance media. At 80% confluency, cells were transduced with ssAAV-EF1α-GFP-P2A-FLuc vectors at MOI 20K for 12-hr and media was replaced. FLuc levels were measured 3-days post-AAV administration using a Luciferase 1000 Assay System kit (Promega Cat#E4550) according to manufacturer's instructions and read on a Veritas luminometer. Experiments were performed in biological triplicate each with technical duplicates or triplicates.

Live in vivo transduction analysis by FLuc imaging and quantitation in mice. All mice having received intramuscular injections of 1E9 vg/leg of ssAAV-EF1α-GFP-P2A-FLuc pseudotyped with various capsid variants were imaged non-invasively (33) every 7-days on a Xenogen IVIS Spectrum imaging system (Caliper Life Sciences). D-luciferin substrate was administered at 120-mg/kg in saline by intraperitoneal injection and images were acquired 10-min later under inhalation isoflurane anesthesia. Living Image v4.5 software was used for image analysis and average radiance was quantified in p/s/cm$^2$/sr.

Ex vivo transduction analysis in human and rhesus skeletal muscle fiber explants. Human or rhesus skeletal muscle specimens were incubated in Collagenase-II (500-U per mL) in Ham's F10 with 10% horse serum and 1% penicillin/streptomycin for 80-min in a 60-rpm shaking water bath. Post-digest, DMEM with 20% FBS and 1% penicillin/streptomycin was added in equal volume and tissue was triturated with a glass pipet to separate single muscle fibers. 300 fibers were counted under a dissecting microscope and placed in each well of a 24-well plate in 1-mL media. Fibers were transduced with 3E8 vg/well of scAAV-CAG-RLuc in triplicate. RLuc levels were measured 48-hrs later using a *Renilla* Luciferase Assay System Kit (Promega Cat#E2820) according to manufacturer's instructions and read on a Veritas luminometer for quantitation, and a Xenogen IVIS Spectrum imaging system for visualization. Immunofluorescence analysis of single transduced human fibers was performed as previously described (32) using a rabbit anti-RLuc monoclonal IgG (Abeam Cat#185926; 1:1,000 V:V) and goat anti-rabbit Alexa Fluor 488 secondary. Imaging was performed on a Leica TCS SP8-X WLL inverted confocal microscope with 40× oil immersion objective and imaged with Leica AF software v3.3.0.10134. White light laser power was kept constant at: 405 nm 48%, 488 nm 75% for all images. Z-stacks were compressed using ImageJ v2.0.0 and overlaid in Adobe Photoshop CS6 v13.0. H&E staining on rhesus skeletal muscle sections was performed according to standard protocols. To obtain uncontracted single human muscle fibers for brightfield imaging, skeletal muscle specimens were digested as described above, transferred to Ham's F10 with 10% horse serum and triturated with a glass pipet to separate single fibers. Fibers were immediately fixed by transferring to 4% PFA (in PBS) and incubated for 10-min. Brightfield imaging was performed with a Keyence BZ-X700 microscope equipped with full BZ acquisition and analysis software.

Luminescence-based AAV neutralization assay against pooled human immunoglobulins. The IVIG neutralization assay was adopted from several previously described methods (17, 56), with modifications. Gammagard IVIG Liquid [100 mg/mL] (Baxter, Product Code#LE1500190, Lot#LE12P180AB) was used with a concentration range of 0-15 mg/mL. The transfer vector utilized was ssAAV-EF1α-GFP-P2A-FLuc. An identical number of genome-containing vector particles of each variant was incubated with increasing concentrations of IVIG at 37° C. for 1-hr. During this hour, differentiation media was changed to that lacking serum or antibiotics/antimycotics. 60K human myotubes were transduced and cultures were washed 12-hr later and cultured for 72-hr in differentiation media. Cells were harvested and analyzed for FLuc expression using a Luciferase 1000 Assay System Kit, according to manufacturer's protocol in white wall 96-well plates on a Veritas luminometer. Each serotype is normalized to its own 'no IVIG' control sample and assessed for the concentration of IVIG needed to decrease the FLuc signal by 50%.

Indirect seroreactivity ELISA assay for anti-AAV antibodies in normal human serum. Off-clot serum collected from peripheral blood of 50 healthy adults (see Table S1) in the United States was used as the primary antibody. Human IgG (Baxter, Cat#LE1500190, Lot#LE12P180AB) was used to prepare a standard curve (16 2-fold dilutions of 100-mg/ml stock IVIG in blocking buffer). Chimeric and control AAV capsids served as the ELISA antigens (5E8 vector genomes/well). Triplicates of human IgG standards and AAV samples were fixed to wells of 96-well immunoplates with 50 μl coating solution (13 mM $Na_2CO_3$, 35 mM $NaHCO_3$ in water, pH 9.6), the plates were sealed, and then incubated overnight at 4° C. Plates were washed 2× with PBS-T containing 0.05% Tween-20, and blocked with blocking buffer (PBS, 6% BSA, 0.05% Tween-20) for 1 hr at 25° C. The plates were washed 2× with PBS-T. Each human sera sample was diluted 1:400 in blocking buffer, and 50 μl was added to each of the experimental wells. Plates were incubated for 2 hr at 37° C. and then washed 2× in PBS-T. Polyclonal sheep anti-human IgG-HRP secondary antibody (GE Bioscience Cat#NA933V) was diluted 1:500 in wash buffer and 100 μl added to the wells to detect bound antibodies in the human sera. Plates were incubated again for 2 hr at 37° C. and washed 2× in PBS-T. OPD substrate (o-phenylenediaminedihydrochloride, Sigma Cat#P4664) was added in 100 μl/well in a 0.1M sodium citrate buffer and incubated at 25° C. for exactly 10 min. The reaction was stopped with 50 μL/well of 3M $H_2SO_4$ and the absorbance determined at 490-nm on a microplate reader (Bio-Rad, Hercules, Calif., USA). A set of "no AAV" blank wells was used to subtract background for non-specific binding of human serum and antibodies to the microplate wells. Standards were plotted using Four Parameter Logistic (4PL) curve fitting to determine the concentration of samples that fall within the linear range.

False-colored structural capsid mapping. Chimeric capsids were false-color mapped onto the AAV8 capsid structure 3RA8 (57) using Pymol v1.7.6.0. Mapped colors correspond to parental serotype colors used in the parental fragment crossover maps. Exterior capsid views have all chains represented, while cross-section views have chains surrounding a cylinder at the 5-fold symmetry axis removed exposing the capsid interior lumen.

Statistics. Statistical analyses were conducted with Prism v6 and Excel v14.5.8 software. Experimental differences were evaluated using a Student's unpaired two-tailed t-test assuming equal variance. P values <0.05 were considered statistically significant.

REFERENCES FOR EXAMPLE 2

1. Pedersen B K, and Febbraio M A. Muscles, exercise and obesity: skeletal muscle as a secretory organ. *Nature reviews Endocrinology.* 2012; 8(8):457-65.
2. Kay M A, Manno C S, Ragni M V, Larson P J, Couto L B, McClelland A, Glader B, Chew A J, Tai S J, Herzog R W, et al. Evidence for gene transfer and expression of factor I X in haemophilia B patients treated with an AAV vector. *Nature genetics.* 2000; 24(3):257-61.
3. Brantly M L, Chulay J D, Wang L, Mueller C, Humphries M, Spencer L T, Rouhani F, Conlon T J, Calcedo R, Betts M R, et al. Sustained transgene expression despite T lymphocyte responses in a clinical trial of rAAV1-AAT gene therapy. *Proceedings of the National Academy of Sciences of the United States of America.* 2009; 106(38): 16363-8.
4. Flotte T R, Brantly M L, Spencer L T, Byrne B J, Spencer C T, Baker D J, and Humphries M. Phase I trial of intramuscular injection of a recombinant adeno-associated virus alpha 1-antitrypsin (rAAV2-C B-hAAT) gene vector to AAT-deficient adults. *Human gene therapy.* 2004; 15(1):93-128.

5. Flotte T R, Trapnell B C, Humphries M, Carey B, Calcedo R, Rouhani F, Campbell-Thompson M, Yachnis A T, Sandhaus R A, McElvaney N G, et al. Phase 2 clinical trial of a recombinant adeno-associated viral vector expressing alpha1-antitrypsin: interim results. *Human gene therapy.* 2011; 22(10):1239-47.

6. Mueller C, Chulay J D, Trapnell B C, Humphries M, Carey B, Sandhaus R A, McElvaney N G, Messina L, Tang Q, Rouhani F N, et al. Human Treg responses allow sustained recombinant adeno-associated virus-mediated transgene expression. *The Journal of clinical investigation.* 2013; 123(12):5310-8.

7. Johnson P R, Schnepp B C, Zhang J, Connell M J, Greene S M, Yuste E, Desrosiers R C, and Clark K R. Vector-mediated gene transfer engenders long-lived neutralizing activity and protection against SIV infection in monkeys. *Nature medicine.* 2009; 15(8):901-6.

8. Balazs A B, Chen J, Hong C M, Rao D S, Yang L, and Baltimore D. Antibody-based protection against HIV infection by vectored immunoprophylaxis. *Nature.* 2012; 481(7379):81-4.

9. Balazs A B, Ouyang Y, Hong C M, Chen J, Nguyen S M, Rao D S, An D S, and Baltimore D. Vectored immunoprophylaxis protects humanized mice from mucosal HIV transmission. *Nature medicine.* 2014; 20(3):296-300.

10. Balazs A B, Bloom J D, Hong C M, Rao D S, and Baltimore D. Broad protection against influenza infection by vectored immunoprophylaxis in mice. *Nature biotechnology.* 2013; 31(7):647-52.

11. Limberis M P, Adam V S, Wong G, Gren J, Kobasa D, Ross T M, Kobinger G P, Tretiakova A, and Wilson J M. Intranasal antibody gene transfer in mice and ferrets elicits broad protection against pandemic influenza. *Science translational medicine.* 2013; 5(187):187ra72.

12. Limberis M P, Racine T, Kobasa D, Li Y, Gao G F, Kobinger G, and Wilson J M. Vectored expression of the broadly neutralizing antibody FI6 in mouse airway provides partial protection against a new avian influenza A virus, H7N9. *Clinical and vaccine immunology: CVI* 2013; 20(12):1836-7.

13. Lin J, Calcedo R, Vandenberghe L H, Bell P, Somanathan S, and Wilson J M. A new genetic vaccine platform based on an adeno-associated virus isolated from a rhesus macaque. *Journal of virology.* 2009; 83(24):12738-50.

14. Sipo I, Knauf M, Fechner H, Poller W, Planz O, Kurth R, and Norley S. Vaccine protection against lethal homologous and heterologous challenge using recombinant AAV vectors expressing codon-optimized genes from pandemic swine origin influenza virus (SOIV). *Vaccine.* 2011; 29(8):1690-9.

15. Gray S J, Blake B L, Criswell H E, Nicolson S C, Samulski R J, McCown T J, and Li W. Directed evolution of a novel adeno-associated virus (AAV) vector that crosses the seizure-compromised blood-brain barrier (BBB). *Molecular therapy: the journal of the American Society of Gene Therapy.* 2010; 18(3):570-8.

16. Bowles D E, McPhee S W, Li C, Gray S J, Samulski J J, Camp A S, Li J, Wang B, Monahan P E, Rabinowitz J E, et al. Phase 1 gene therapy for Duchenne muscular dystrophy using a translational optimized AAV vector. *Molecular therapy: the journal of the American Society of Gene Therapy.* 2012; 20(2):443-55.

17. Grimm D, Lee J S, Wang L, Desai T, Akache B, Storm T A, and Kay M A. In vitro and in vivo gene therapy vector evolution via multispecies interbreeding and retargeting of adeno-associated viruses. *Journal of virology.* 2008; 82(12):5887-911.

18. Li W, Asokan A, Wu Z, Van Dyke T, DiPrimio N, Johnson J S, Govindaswamy L, Agbandje-McKenna M, Leichtle S, Redmond D E, Jr., et al. Engineering and selection of shuffled AAV genomes: a new strategy for producing targeted biological nanoparticles. *Molecular therapy: the journal of the American Society of Gene Therapy.* 2008; 16(7):1252-60.

19. Kotterman M A, and Schaffer D V. Engineering adeno-associated viruses for clinical gene therapy. *Nature reviews Genetics.* 2014; 15(7):445-51.

20. Jang J H, Koerber J T, Kim J S, Asuri P, Vazin T, Bartel M, Keung A, Kwon I, Park K I, and Schaffer D V. An evolved adeno-associated viral variant enhances gene delivery and gene targeting in neural stem cells. *Molecular therapy: the journal of the American Society of Gene Therapy.* 2011; 19(4):667-75.

21. Davidoff A M, Gray J T, Ng C Y, Zhang Y, Zhou J, Spence Y, Bakar Y, and Nathwani A C. Comparison of the ability of adeno-associated viral vectors pseudotyped with serotype 2, 5, and 8 capsid proteins to mediate efficient transduction of the liver in murine and nonhuman primate models. *Molecular therapy: the journal of the American Society of Gene Therapy.* 2005; 11(6):875-88.

22. Nathwani A C, Tuddenham E G, Rangarajan S, Rosales C, McIntosh J, Linch D C, Chowdary P, Riddell A, Pie A J, Harrington C, et al. Adenovirus-associated virus vector-mediated gene transfer in hemophilia B. *The New England journal of medicine.* 2011; 365(25):2357-65.

23. Nathwani A C, Gray J T, McIntosh J, Ng C Y, Zhou J, Spence Y, Cochrane M, Gray E, Tuddenham E G, and Davidoff A M. Safe and efficient transduction of the liver after peripheral vein infusion of self-complementary AAV vector results in stable therapeutic expression of human FIX in nonhuman primates. *Blood.* 2007; 109(4):1414-21.

24. Nathwani A C, Gray J T, Ng C Y, Zhou J, Spence Y, Waddington S N, Tuddenham E G, Kemball-Cook G, McIntosh J, Boon-Spijker M, et al. Self-complementary adeno-associated virus vectors containing a novel liver-specific human factor I X expression cassette enable highly efficient transduction of murine and nonhuman primate liver. *Blood.* 2006; 107(7):2653-61.

25. Nathwani A C, Reiss U M, Tuddenham E G, Rosales C, Chowdary P, McIntosh J, Della Peruta M, Lheriteau E, Patel N, Raj D, et al. Long-term safety and efficacy of factor I X gene therapy in hemophilia B. *The New England journal of medicine.* 2014; 371(21):1994-2004.

26. Salganik M, Aydemir F, Nam H J, McKenna R, Agbandje-McKenna M, and Muzyczka N. Adeno-associated virus capsid proteins may play a role in transcription and second-strand synthesis of recombinant genomes. *Journal of virology.* 2014; 88(2):1071-9.

27. Ploquin A, Szecsi J, Mathieu C, Guillaume V, Barateau V, Ong K C, Wong K T, Cosset F L, Horvat B, and Salvetti A. Protection against henipavirus infection by use of recombinant adeno-associated virus-vector vaccines. *The Journal of infectious diseases.* 2013; 207(3):469-78.

28. Kuck D, Lau T, Leuchs B, Kern A, Muller M, Gissmann L, and Kleinschmidt J A. Intranasal vaccination with recombinant adeno-associated virus type 5 against human papillomavirus type 16 L1. *Journal of virology.* 2006; 80(6):2621-30.

29. Nieto K, Kern A, Leuchs B, Gissmann L, Muller M, and Kleinschmidt J A. Combined prophylactic and therapeutic intranasal vaccination against human papillomavirus type-16 using different adeno-associated virus serotype vectors. *Antiviral therapy.* 2009; 14(8):1125-37.

30. Nieto K, Stahl-Hennig C, Leuchs B, Muller M, Gissmann L, and Kleinschmidt J A. Intranasal vaccination with AAV5 and 9 vectors against human papillomavirus type 16 in rhesus macaques. *Human gene therapy.* 2012; 23(7):733-41.
31. Zhou L, Zhu T, Ye X, Yang L, Wang B, Liang X, Lu L, Tsao Y P, Chen S L, Li J, et al. Long-term protection against human papillomavirus e7-positive tumor by a single vaccination of adeno-associated virus vectors encoding a fusion protein of inactivated e7 of human papillomavirus 16/18 and heat shock protein 70. *Human gene therapy.* 2010; 21(1):109-19.
32. Charville G W, Cheung T H, Yoo B, Santos P J, Lee G K, Shrager J B, and Rando T A. Ex Vivo Expansion and In Vivo Self-Renewal of Human Muscle Stem Cells. *Stem cell reports.* 2015; 5(4):621-32.
33. Maguire K K, Lim L, Speedy S, and Rando T A. Assessment of disease activity in muscular dystrophies by noninvasive imaging. *The Journal of clinical investigation.* 2013; 123(5):2298-305.
34. Rayaprolu V, Kruse S, Kant R, Venkatakrishnan B, Movahed N, Brooke D, Lins B, Bennett A, Potter T, McKenna R, et al. Comparative analysis of adeno-associated virus capsid stability and dynamics. *Journal of virology.* 2013; 87(24):13150-60.
35. Croyle M A, Cheng X, and Wilson J M. Development of formulations that enhance physical stability of viral vectors for gene therapy. *Gene therapy.* 2001; 8(17):1281-90.
36. Martinez-Navio J M, Fuchs S P, Pedreno-Lopez S, Rakasz E G, Gao G, and Desrosiers R C. Host Anti-antibody Responses Following Adeno-associated Virus-mediated Delivery of Antibodies Against HIV and SIV in Rhesus Monkeys. *Molecular therapy: the journal of the American Society of Gene Therapy.* 2015.
37. Mingozzi F, and High K A. Immune responses to AAV vectors: overcoming barriers to successful gene therapy. *Blood.* 2013; 122(1):23-36.
38. Greig J A, Calcedo R, Grant R L, Peng H, Medina-Jaszek C A, Ahonkhai O, Qin Q, Roy S, Tretiakova A, and Wilson J M. Intramuscular administration of AAV overcomes pre-existing neutralizing antibodies in rhesus macaques. *Vaccine.* 2016.
39. Han X, and Ni W. Cost-Effectiveness Analysis of Glybera for The Treatment of Lipoprotein Lipase Deficiency. *Value in health: the journal of the International Society for Pharmacoeconomics and Outcomes Research.* 2015; 18(7):A756.
40. Morrison C. $1-million price tag set for Glybera gene therapy. *Nature biotechnology.* 2015; 33(3):217-8.
41. Lochrie M A, Tatsuno G P, Christie B, McDonnell J W, Zhou S, Surosky R, Pierce G F, and Colosi P. Mutations on the external surfaces of adeno-associated virus type 2 capsids that affect transduction and neutralization. *Journal of virology.* 2006; 80(2):821-34.
42. McCraw D M, O'Donnell J K, Taylor K A, Stagg S M, and Chapman M S. Structure of adeno-associated virus-2 in complex with neutralizing monoclonal antibody A20. *Virology.* 2012; 431(1-2):40-9.
43. Calcedo R, Vandenberghe L H, Gao G, Lin J, and Wilson J M. Worldwide epidemiology of neutralizing antibodies to adeno-associated viruses. *The Journal of infectious diseases.* 2009; 199(3):381-90.
44. Boutin S, Monteilhet V, Veron P, Leborgne C, Benveniste O, Montus M F, and Masurier C. Prevalence of serum IgG and neutralizing factors against adeno-associated virus (AAV) types 1, 2, 5, 6, 8, and 9 in the healthy population: implications for gene therapy using AAV vectors. *Human gene therapy.* 2010; 21(6):704-12.
45. Foust K D, Wang X, McGovern V L, Braun L, Bevan A K, Haidet A M, Le T T, Morales P R, Rich M M, Burghes A H, et al. Rescue of the spinal muscular atrophy phenotype in a mouse model by early postnatal delivery of SMN. *Nature biotechnology.* 2010; 28(3):271-4.
46. Tabebordbar M, Zhu K, Cheng J K, Chew W L, Widrick J J, Yan W X, Maesner C, Wu E Y, Xiao R, Ran F A, et al. In vivo gene editing in dystrophic mouse muscle and muscle stem cells. *Science.* 2016; 351(6271):407-11.
47. Nelson C E, Hakim C H, Ousterout D G, Thakore P I, Moreb E A, Castellanos Rivera R M, Madhavan S, Pan X, Ran F A, Yan W X, et al. In vivo genome editing improves muscle function in a mouse model of Duchenne muscular dystrophy. *Science.* 2016; 351(6271):403-7.
48. Long C, Amoasii L, Mireault A A, McAnally J R, Li H, Sanchez-Ortiz E, Bhattacharyya S, Shelton J M, Bassel-Duby R, and Olson E N. Postnatal genome editing partially restores dystrophin expression in a mouse model of muscular dystrophy. *Science.* 2016; 351(6271):400-3.
49. Kienle E, Senis E, Borner K, Niopek D, Wiedtke E, Grosse S, and Grimm D. Engineering and evolution of synthetic adeno-associated virus gene therapy vectors via DNA family shuffling. *Journal of Visualized Experiments.* 2012; 62(3819):1-11.
50. Grimm D. Production methods for gene transfer vectors based on adeno-associated virus serotypes. *Methods.* 2002; 28(2):146-57.
51. Liu L, Cheung T H, Charville G W, and Rando T A. Isolation of skeletal muscle stem cells by fluorescence-activated cell sorting. *Nature protocols.* 2015; 10(10): 1612-24.
52. Casar J C, Cabello-Verrugio C, Olguin H, Aldunate R, Inestrosa N C, and Brandan E. Heparan sulfate proteoglycans are increased during skeletal muscle regeneration: requirement of syndecan-3 for successful fiber formation. *Journal of cell science.* 2004; 117(Pt 1):73-84.
53. Huang W, Johnston W A, Boden M, and Gillam E M. ReX: A suite of computational tools for the design, visualization, and analysis of chimeric protein libraries. *BioTechniques.* 2016; 60(2):91-4.
54. Edgar R C. MUSCLE: multiple sequence alignment with high accuracy and high throughput. *Nucleic Acids Res.* 2004; 32(5):1792-7.
55. Stamatakis A, Ludwig T, and Meier H. RAxML-III: a fast program for maximum likelihood-based inference of large phylogenetic trees. *Bioinformatics.* 2005; 21(4): 456-63.
56. Arbetman A E, Lochrie M, Zhou S, Wellman J, Scallan C, Doroudchi M M, Randlev B, Patarroyo-White S, Liu T, Smith P, et al. Novel caprine adeno-associated virus (AAV) capsid (AAV-Go.1) is closely related to the primate AAV-5 and has unique tropism and neutralization properties. *Journal of virology.* 2005; 79(24):15238-45.
57. Nam H J, Gurda B L, McKenna R, Potter M, Byrne B, Salganik M, Muzyczka N, and Agbandje-McKenna M. Structural studies of adeno-associated virus serotype 8 capsid transitions associated with endosomal trafficking. *Journal of virology.* 2011; 85(22):11791-9.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A variant adeno-associated virus (AAV) capsid polypeptide, wherein said variant AAV capsid polypeptide exhibits increased transduction or tropism in human skeletal muscle tissue or cells as compared to a non-variant parent capsid polypeptide, wherein said variant AAV capsid polypeptide comprises a sequence selected from the group consisting of AAV-NP6 (SEQ ID NO: 1), AAV-NP20 (SEQ ID NO: 2), AAV-NP22(SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7).

2. The variant AAV capsid polypeptide of claim 1, wherein said variant AAV capsid polypeptide exhibits increased transduction as compared to a non-variant parent capsid polypeptide.

3. The variant AAV capsid polypeptide of claim 1, wherein said variant AAV capsid polypeptide exhibits increased tropism as compared to a non-variant parent capsid polypeptide.

4. The variant AAV capsid polypeptide of claim 1, wherein said variant AAV capsid polypeptide further exhibits an enhanced neutralization profile as compared to a non-variant parent capsid polypeptide.

5. The variant AAV capsid polypeptide of claim 1, wherein said variant AAV capsid polypeptide further exhibits increased transduction or tropism in one or more non-muscle human tissues as compared to a non-variant parent capsid polypeptide.

6. The variant AAV capsid polypeptide of claim 1, wherein said variant AAV capsid polypeptide exhibits increased transduction of human muscle tissue or cells in vivo as compared to a non-variant parent capsid polypeptide.

7. The variant AAV capsid polypeptide of claim 1, wherein said variant AAV capsid polypeptide exhibits increased transduction of human muscle tissue or cells in vitro as compared to a non-variant parent capsid polypeptide.

8. The variant AAV capsid polypeptide of claim 1, wherein said variant AAV capsid polypeptide exhibits increased transduction of a human muscle tissue explant ex vivo as compared to a non-variant parent capsid polypeptide.

9. The variant AAV capsid polypeptide of claim 1, wherein said variant AAV capsid polypeptide is part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

10. The variant AAV capsid polypeptide of claim 9, wherein said nucleic acid sequence is contained within an AAV vector.

11. The variant AAV capsid polypeptide of claim 9, wherein said expression cassette is a CRISPR/CAS expression system.

12. The variant AAV capsid polypeptide of claim 9, wherein said therapeutic expression cassette encodes a therapeutic protein or antibody.

13. The variant AAV capsid polypeptide of claim 1, wherein said variant AAV capsid polypeptide sequence is AAV-NP22 (SEQ ID NO: 3).

14. The variant AAV capsid polypeptide of claim 1, wherein said variant AAV capsid polypeptide sequence is AAV-NP66 (SEQ ID NO: 5).

15. The variant AAV capsid polypeptide of claim 1, wherein said variant AAV capsid polypeptide sequence is AAV-NP6 (SEQ ID NO: 1).

16. The variant AAV capsid polypeptide of claim 1, wherein said variant AAV capsid polypeptide sequence is AAV-NP20 (SEQ ID NO: 2).

17. The variant AAV capsid polypeptide of claim 1, wherein said variant AAV capsid polypeptide sequence is AAV-NP36 (SEQ ID NO: 4).

18. The variant AAV capsid polypeptide of claim 1, wherein said variant AAV capsid polypeptide sequence is AAV-NP81 (SEQ ID NO: 6).

19. The variant AAV capsid polypeptide of claim 1, wherein said variant AAV capsid polypeptide sequence is AAV-NP94 (SEQ ID NO: 7).

20. The variant AAV capsid polypeptide of claim 9, wherein said variant AAV capsid polypeptide results in increased nucleic acid expression as compared to a non-variant parent capsid polypeptide.

21. A variant adeno-associated virus (AAV) capsid polypeptide, wherein said variant AAV capsid polypeptide exhibits enhanced neutralization profile as compared to a non-variant parent capsid polypeptide, wherein said variant AAV capsid polypeptide comprises a sequence selected from the group consisting of AAV-NP6 (SEQ ID NO: 1), AAV-NP20 (SEQ ID NO: 2), AAV-NP22 (SEQ ID NO: 3), AAV-NP36 (SEQ ID NO: 4), AAV-NP66 (SEQ ID NO: 5), AAV-NP81 (SEQ ID NO: 6), and AAV-NP94 (SEQ ID NO: 7).

22. The variant AAV capsid polypeptide of claim 21, wherein said variant AAV capsid polypeptide exhibits an enhanced neutralization profile against pooled human immunoglobulins as compared to a non-variant parent capsid polypeptide.

23. The variant AAV capsid polypeptide of claim 21, wherein said variant AAV capsid polypeptide further exhibits increased transduction or tropism in human skeletal muscle tissue or cells as compared to a non-variant parent capsid polypeptide.

24. The variant AAV capsid polypeptide of claim 23, wherein said variant AAV capsid polypeptide exhibits increased transduction as compared to a non-variant parent capsid polypeptide.

25. The variant AAV capsid polypeptide of claim 23, wherein said variant AAV capsid polypeptide exhibits increased tropism as compared to a non-variant parent capsid polypeptide.

26. The variant AAV capsid polypeptide of claim 21, wherein said variant AAV capsid polypeptide further exhibits increased transduction or tropism in one or more non-muscle human tissues as compared to a non-variant parent capsid polypeptide.

27. The variant AAV capsid polypeptide of claim 21, wherein said variant AAV capsid polypeptide exhibits increased transduction of human muscle tissue or cells in vivo as compared to a non-variant parent capsid polypeptide.

28. The variant AAV capsid polypeptide of claim 21, wherein said variant AAV capsid polypeptide exhibits increased transduction of human muscle tissue or cells in vitro as compared to a non-variant parent capsid polypeptide.

29. The variant AAV capsid polypeptide of claim 21, wherein said variant AAV capsid polypeptide exhibits increased transduction of a human muscle tissue explant ex vivo as compared to a non-variant parent capsid polypeptide.

30. The variant AAV capsid polypeptide of claim 21, wherein said variant AAV capsid polypeptide is part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

31. The variant AAV capsid polypeptide of claim 30, wherein said nucleic acid sequence is contained within an AAV vector.

32. The variant AAV capsid polypeptide of claim 30, wherein said expression cassette is a CRISPR/CAS expression system.

33. The variant AAV capsid polypeptide of claim 30, wherein said therapeutic expression cassette encodes a therapeutic protein or antibody.

34. The variant AAV capsid polypeptide of claim 30, wherein said variant AAV capsid polypeptide results in increased nucleic acid expression as compared to a non-variant parent capsid polypeptide.

35. The variant AAV capsid polypeptide of claim 21, wherein said variant AAV capsid polypeptide sequence is AAV-NP22 (SEQ ID NO: 3).

36. The variant AAV capsid polypeptide of claim 21, wherein said variant AAV capsid polypeptide sequence is AAV-NP66 (SEQ ID NO: 5).

37. The variant AAV capsid polypeptide of claim 21, wherein said variant AAV capsid polypeptide sequence is AAV-NP6 (SEQ ID NO: 1).

38. The variant AAV capsid polypeptide of claim 21, wherein said variant AAV capsid polypeptide sequence is AAV-NP20 (SEQ ID NO: 2).

39. The variant AAV capsid polypeptide of claim 21, wherein said variant AAV capsid polypeptide sequence is AAV-NP36 (SEQ ID NO: 4).

40. The variant AAV capsid polypeptide of claim 21, wherein said variant AAV capsid polypeptide sequence is AAV-NP81 (SEQ ID NO: 6).

41. The variant AAV capsid polypeptide of claim 21, wherein said variant AAV capsid polypeptide sequence is AAV-NP94 (SEQ ID NO: 7).

* * * * *

SEQUENCE LISTING

```
<160> NUMBER OF SEQ ID NOS: 30

<210> SEQ ID NO 1
<211> LENGTH: 735
<212> TYPE: PRT
<213> ORGANISM: Artificial Sequence
<220> FEATURE:
<223> OTHER INFORMATION: capsid polypeptide

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270
```

-continued

```
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
290                 295                 300
Gly Phe Arg Pro Lys Arg Leu Ser Phe Lys Leu Phe Asn Ile Gln Val
305                 310                 315                 320
Lys Glu Val Thr Gln Asn Glu Gly Thr Lys Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asp
                645                 650                 655
Pro Pro Thr Thr Phe Asn Gln Ser Lys Leu Asn Ser Phe Ile Thr Gln
                660                 665                 670
Tyr Ser Thr Gly Gln Val Ser Val Glu Ile Glu Trp Glu Leu Gln Lys
            675                 680                 685
```

```
Glu Asn Ser Lys Arg Trp Asn Pro Glu Ile Gln Tyr Thr Ser Asn Tyr
    690             695                 700

Tyr Lys Ser Thr Ser Val Asp Phe Ala Val Asn Thr Glu Gly Val Tyr
705             710                 715                 720

Ser Glu Pro Arg Pro Ile Gly Thr Arg Tyr Leu Thr Arg Asn Leu
            725                 730                 735

<210> SEQ ID NO 2
<211> LENGTH: 735
<212> TYPE: PRT
<213> ORGANISM: Artificial Sequence
<220> FEATURE:
<223> OTHER INFORMATION: capsid polypeptide

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Ser Phe Lys Leu Phe Asn Ile Gln Val
305                 310                 315                 320
```

```
Lys Glu Val Thr Gln Asn Glu Gly Thr Lys Thr Ile Ala Asn Asn Leu
                325                 330                 335

Thr Ser Thr Ile Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Thr Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
        580                 585                 590

Ala Asp Val Asn Thr Gln Gly Val Leu Pro Gly Met Val Trp Gln Asp
    595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
        660                 665                 670

Tyr Ser Thr Gly Gln Val Ser Val Glu Ile Glu Trp Glu Leu Gln Lys
    675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735
```

-continued

```
<210> SEQ ID NO 3
<211> LENGTH: 735
<212> TYPE: PRT
<213> ORGANISM: Artificial Sequence
<220> FEATURE:
<223> OTHER INFORMATION: capsid polypeptide

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Lys Thr Ile Ala Asn Asn Leu
                325                 330                 335

Thr Ser Thr Ile Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
```

```
            370                 375                 380
Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Thr Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Gln Thr Thr Gly Gly Thr Thr Asn Thr Gln Thr Leu Gly Phe Ser Gln
                450                 455                 460

Gly Gly Pro Asn Thr Met Ala Asn Gln Ala Lys Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 4
<211> LENGTH: 735
<212> TYPE: PRT
<213> ORGANISM: Artificial Sequence
<220> FEATURE:
<223> OTHER INFORMATION: capsid polypeptide

<400> SEQUENCE: 4

Met Ala Ala Asp Gly Tyr Leu Pro Asp Trp Leu Glu Asp Asn Leu Ser
```

-continued

```
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Ser Arg Gly Leu Val Leu Pro
                35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
                115                 120                 125
Leu Gly Leu Val Glu Glu Pro Val Lys Thr Ala Pro Gly Lys Lys Arg
                130                 135                 140
Pro Val Glu Gln Ser Pro Gln Glu Pro Asp Ser Ser Ser Gly Ile Gly
145                 150                 155                 160
Lys Thr Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
                180                 185                 190
Ala Ala Pro Ser Gly Leu Gly Thr Asn Thr Met Ala Thr Gly Ser Gly
                195                 200                 205
Ala Pro Met Ala Asp Asn Asn Glu Gly Ala Asp Gly Val Gly Asn Ser
                210                 215                 220
Ser Gly Asn Trp His Cys Asp Ser Thr Trp Met Gly Asp Arg Val Ile
225                 230                 235                 240
Thr Ile Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
                275                 280                 285
Cys His Phe Ser Pro Arg Asp Trp Gln Arg Leu Ile Asn Asn Asn Trp
                290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
                370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
```

```
Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asp Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 5
<211> LENGTH: 735
<212> TYPE: PRT
<213> ORGANISM: Artificial Sequence
<220> FEATURE:
<223> OTHER INFORMATION: capsid polypeptide

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Ser Phe Lys Leu Phe Asn Ile Gln Val
305                 310                 315                 320

Lys Glu Val Thr Gln Asn Glu Gly Thr Lys Thr Ile Ala Asn Asn Leu
                325                 330                 335

Thr Ser Thr Ile Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Thr Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Gln Thr Thr Gly Gly Thr Thr Asn Thr Gln Thr Leu Gly Phe Ser Gln
450                 455                 460

Gly Gly Pro Asn Thr Met Ala Asn Gln Ala Lys Asn Trp Leu Pro Gly
465                 470                 475                 480
```

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735

<210> SEQ ID NO 6
<211> LENGTH: 735
<212> TYPE: PRT
<213> ORGANISM: Artificial Sequence
<220> FEATURE:
<223> OTHER INFORMATION: capsid polypeptide

<400> SEQUENCE: 6

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

-continued

Asn Leu Gly Arg Ala Val Phe Gln Ala Lys Lys Arg Val Leu Glu Pro
    115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
290                 295                 300
Gly Phe Arg Pro Lys Lys Leu Ser Phe Lys Leu Phe Asn Ile Gln Val
305                 310                 315                 320
Lys Glu Val Thr Gln Asn Glu Gly Thr Lys Thr Ile Ala Asn Asn Leu
                325                 330                 335
Thr Ser Thr Ile Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Ile Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Thr Tyr Thr Phe Glu
                405                 410                 415
Gly Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Gln Thr Thr Gly Gly Thr Thr Asn Thr Gln Thr Leu Gly Phe Ser Gln
450                 455                 460
Gly Gly Pro Asn Thr Met Ala Asn Gln Ala Lys Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Thr Ser His Lys Asp
        515                 520                 525
Asp Glu Glu Lys Phe Phe Pro Gln Ser Gly Val Leu Ile Phe Gly Lys

```
            530                 535                 540
Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 7
<211> LENGTH: 735
<212> TYPE: PRT
<213> ORGANISM: Artificial Sequence
<220> FEATURE:
<223> OTHER INFORMATION: capsid polypeptide

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
```

-continued

```
                165                 170                 175
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Ile Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Ile Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590
```

```
Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 8
<211> LENGTH: 2208
<212> TYPE: DNA
<213> ORGANISM: Artificial Sequence
<220> FEATURE:
<223> OTHER INFORMATION: capsid gene

<400> SEQUENCE: 8
atggctgccg atggttatct tccagattgg ctcgaggaca accttagtga aggaattcgc      60
gagtggtggg acttgaaacc tggagccccg aagcccaaag ccaaccagca aaagcaggac     120
gacggccggg gtctggtgct tcctggctac aagtacctcg acccttcaa cggactcgac      180 aagggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggtgctaa gacggctcct     420
ggaaagaaac gtccggtaga gcagtcgcca aagagccag actcctcctc gggcattggc      480
aagacaggcc agcagcccgc taaaaagaga ctcaattttg gtcagactgg cgactcagag     540
tcagtccccg acccacaacc tctcggagaa cctccagcaa ccccgctgc tgtgggacct      600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgaacctg ggccctgccc acctacaaca accacctcta caaacaaatt     780
tccagccaat caggagcctc gaacgacaat cactactttg ctacagcac ccttgggggg     840 tattttgatt tcaacagatt ccactgccac ttttcaccac gtgactggca gcgactcatc     900
aacaacaatt ggggattccg gcccaagaga ctcagcttca gctcttcaa catccaggtc     960 aaggaggtca cgcagaatga aggcaccaag accatcgcca ataaccttac cagcacggtt    1020
caagtgttta cggactcgga gtatcagctc ccgtacgtgc tcggtcggc gcatcaagga    1080 tgcctcccgc cgttcccagc agacgtcttc atggtgccac agtatggata cctcacccct    1140
aacaacggga gtcaggcagt aggacgctct tcatttttact gcctggagta ctttccttct    1200
cagatgctgc gtaccggaaa caacttttacc ttcagctaca cttttgagga cgttcctttc    1260
```

```
cacagcagct acgctcacag ccagagtctg gaccgtctca tgaatcctct gattgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca tttttcacccg tctccgctga tgggcggctt tggcctgaaa    1920
catcctccgc ctcagatcct gatcaagaac acgcctgtac ctgcggatcc tccgaccacc    1980
ttcaaccagt caaagctgaa ctctttcatc actcagtatt ctactggcca agtcagcgtg    2040
gagatcgagt gggagctgca gaaggaaaac agcaagcgct ggaaccccga gatccagtac    2100
acctccaact actacaaatc tacaagtgtg gactttgctg ttaatacaga aggcgtgtac    2160 tctgaaccc gccccattgg cacccgttac ctcacccgta atctgtaa                 2208

<210> SEQ ID NO 9
<211> LENGTH: 2208
<212> TYPE: DNA
<213> ORGANISM: Artificial Sequence
<220> FEATURE:
<223> OTHER INFORMATION: capsid gene

<400> SEQUENCE: 9
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg gacccttcaa cggactcgac     180
aagggggagc ccgtcaacgc ggcggatgca gcggccctcg agcacgacaa ggcctacgac     240
cagcagctca agcgggtgaa caatccgtac ctgcggtata accacgccga cgccgagttt     300
caggagcgtc tgcaagaaga tacgtctttt ggggggcaacc tcgggcgagc agtcttccag     360
gccaagaagc gggttctcga acctctcggt ctggttgagg aaggcgctaa gacggctcct     420
ggaaagaaac gtccggtaga gcagtcgcca aagagccag actcctcctc gggcatcggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600 actacaatgg cttcaggcgg tggcgcacca atggcagaca ataacgaagg cgccgacgga     660
gtgggtaatg cctcaggaaa ttggcattgc gattcccaat ggctgggcga cagagtcatc     720
accaccagca cccgaacctg ggccctgccc acctacaaca accacctcta caaacaaatt     780
tccagccaat caggagcctc gaacgacaat cactactttg gctacagcac cccttggggg     840
tattttgact tcaacagatt ccactgccac ttttcaccac gtgactggca gcgactcatc     900
aacaacaact ggggattccg gcccaagaga ctcagcttca gctcttcaa catccaggtc     960 aaggaggtca cgcagaatga aggcaccaag accatcgcca ataacctcac cagcaccatc    1020
caggtgttta cggactcgga gtaccagctg ccgtacgttc tcggctctgc ccaccagggc    1080
```

```
tgcctgcctc cgttcccggc ggacgtgttc atgattcccc agtacggcta cctaacactc    1140
aacaacggta gtcaggccgt gggacgctcc tccttctact gcctggaata ctttccttcg    1200
cagatgctga gaaccggcaa caacttccag tttacttaca ccttcgagga cgtgcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccactc aatggcagag actctctggt gaatccgggc    1560
ccggccatgg caagccacaa ggacgatgaa gaaaagtttt tccctcagag cggggttctc    1620
atctttggaa agcaaggctc agagaaaaca aatgtggaca ttgaaaaggt tatgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccgtac ctgcgaatcc ttcgaccacc    1980
ttcagtgcgg caaagtttgc ttccttcatc acacagtact ccacgggaca ggtcagcgtg    2040
gagatcgagt gggagctgca aaaggaaaac agcaaacgct ggaatcccga aattcagtac    2100
acttccaact acaacaagtc tgttaatgtg gactttactg tagacactaa tggtgtttat    2160
agtgaacctc gccctattgg aacccggtat ctcacacgaa acttgtaa                 2208

<210> SEQ ID NO 10
<211> LENGTH: 2208
<212> TYPE: DNA
<213> ORGANISM: Artificial Sequence
<220> FEATURE:
<223> OTHER INFORMATION: capsid gene

<400> SEQUENCE: 10
atggctgccg atggttatct tccagattgg ctcgaggaca acctttctga aggcattcgt      60
gagtggtggg ctctgaaacc tggagtccct caacccaaag ccaaccagca aaagcaggac     120
gacgccgggt gtctggtgct tcctggctac aagtacctcg acccttcaa cggactcgac     180 aagggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aagcggctaa gacggctcct     420
ggaaagaaga ggcctgtaga gcactctcct gtggagccag actcctcctc gggaaccgga     480
aaggcgggcc agcagcctgc aagaaaaaga ttgaattttg gtcagactgg agacgcagac     540
tcagtcccag accctcaacc aatcggagaa cctcccgcag ccccctcagg tgtgggatct     600
cttacaatgg ctgcaggcgg tggcgcacca atggcagaca ataacgaggg tgccgatgga     660
gtgggtaatt cctcaggaaa ttggcattgc gattcccaat ggctgggcga cagagtcatc     720
accaccagca ccagaacctg gcccctgccc acttacaaca accatctcta caagcaaatc     780
tccagccaat caggagcttc aaacgacaac cactactttg gctacagcac cccttggggg     840
tattttgact ttaacagatt ccactgccac ttctcaccac gtgactggca gcgactcatt     900
aacaacaact gggggattcc gcccaagaaa ctcagcttca gctcttcaa catccaagtt     960
```

```
aaagaggtca cgcagaatga tggcaccaag accatcgcca ataacctcac cagcaccatc    1020
caggtgttta cggactcgga gtaccagctg ccgtacgttc tcggctctgc ccaccagggc    1080
tgcctgcctc cgttcccggc ggacgtgttc atgattccgc agtacggcta cctaacactc    1140
aacaacggta gtcaggccgt gggacgctcc tccttctact gcctggaata ctttccttcg    1200
cagatgctga gaaccggcaa caacttccag tttacttaca ccttcgagga cgtgcctttc    1260
cacagcagct acgctcacag ccagagtctg gaccgtctca tgaatcctct catcgaccag    1320
tacctgtatt acttgtctcg gactcaaaca acaggaggca cgacaaatac gcagactctg    1380
ggcttcagcc aagtgggcc taatacaatg gccaatcagg caagaactg ctgccagga     1440 ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga gcaaggctc agagaaaaca atgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccg tctccgctga tgggcggctt tggcctgaaa    1920
catcctccgc ctcagatcct gatcaagaac acgcctgtac ctgcggatcc tccgaccacc    1980
ttcaaccagt caaagctgaa ctctttcatc actcagtatt ctactggcca agtcagcgtg    2040
gagatcgagt gggagctgca gaaggaaaac agcaagcgct ggaatcccga aattcagtac    2100
acttccaact acaacaagtc tgttaatgtg gactttactg tggacactaa tggcgtgtat    2160
tcagagcctc gccccattgg caccagatac ctgactcgta atctgtaa              2208
```

<210> SEQ ID NO 11
<211> LENGTH: 2208
<212> TYPE: DNA
<213> ORGANISM: Artificial Sequence
<220> FEATURE:
<223> OTHER INFORMATION: capsid gene

<400> SEQUENCE: 11

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacagcaggg gtcttgtgct tcctgggtac aagtacctcg acccttcaa cggactcgac    180 aagggagagc cggtcaacga ggcagacgcc gcggccctcg agcacgacaa agcctacgac    240
cggcagctcg acagcggaga caacccgtac ctcaagtaca accacgccga cgcggagttc    300
caggagcggc tcaaagaaga tacgtctttt ggggcaacc tcgggcgagc agtcttccag    360
gccaaaaaga ggcttcttga acctcttggt ctggttgagg aacctgttaa gacggctcct    420
ggaaagaaac gtccggtaga gcagtcgcca caagagccag actcctcctc gggcatcggc    480
aagacaggcc agcagcctgc aagaaaaaga ttgaattttg gtcagactgg agacgcagac    540
tcagtacctg accccagcc tctcggacag ccaccagcag cccctctgg tctgggaact    600 aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accatcagca cccgaacctg ggcctgcc acctacaaca accacctcta caaacaaatt    780
```

```
tccagccaat caggagcctc gaacgacaac cactactttg gctacagcac cccttgggggg    840 tattttgact ttaacagatt ccactgccac ttctcaccac gtgactggca gcgactcatt    900
aacaacaact ggggattccg gcccaagaaa ctcagcttca agctcttcaa catccaagtt    960
aaagaggtca cgcagaacga tggcacgacg actattgcca ataaccttac cagcacggtt   1020
caagtgttta cggactcgga gtatcagctc ccgtacgtgc tcgggtcggc gcatcaagga   1080
tgcctcccgc cgttcccagc agacgtcttc atggtgccac agtatggata cctcaccctg   1140
aacaacggga gtcaggcagt aggacgctct tcatttttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct tatcgaccag   1320
tacctgtatt acttgagcag aacaaacact ccaagtggaa ccaccacgca gtcaaggctt   1380 cagtttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tccctcagag cggggttctc   1620
atctttggga agcaaggctc agagaaaaca gatgtggaca ttgaaaaggt catgattaca   1680
gacgaagagg aaatcaggac aaccaatccc gtggctacgg agcagtatgg ttctgtatct   1740
accaacctcc agagagcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa               2208
```

<210> SEQ ID NO 12
<211> LENGTH: 2208
<212> TYPE: DNA
<213> ORGANISM: Artificial Sequence
<220> FEATURE:
<223> OTHER INFORMATION: capsid gene

<400> SEQUENCE: 12

```
atggctgccg atggttatct tccagattgg ctcgaggaca accttagtga aggaattcgc     60
gagtggtggg acttgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
actacaatgg cttcaggcgg tggcgcacca atggcagaca ataacgaagg cgccgacgga    660
```

```
gtgggtaatg cctcaggaaa ttggcattgc gattccacat ggctgggcga cagagtcatc      720
accaccagca cccgaacctg ggccctgccc acctacaaca accacctcta caaacaaatt      780
tccagccaat caggagcctc gaacgacaat cactactttg ctacagcac  cccttggggg      840 tattttgact tcaacagatt ccactgccac ttttcaccac gtgactggca gcgactcatc      900
aacaacaact ggggattccg gcccaagaga ctcagcttca agctcttcaa catccaggtc      960
aaggaggtca cgcagaatga aggcaccaag accatcgcca ataacctcac cagcaccatc     1020
caggtgttta cggactcgga gtaccagctg ccgtacgttc tcggctctgc ccaccagggc     1080
tgcctgcctc cgttcccggc ggacgtgttc atgattcccc agtacggcta cctaacactc     1140
aacaacggta gtcaggccgt gggacgctcc tccttctact gcctggaata ctttcccttcg     1200 cagatgctga aaccggcaa caacttccag tttacttaca ccttcgagga cgtgcctttc     1260
cacagcagct acgcccacag ccagagcttg accggctga tgaatcctct gattgaccag     1320
tacctgtact acttgtctcg gactcaaaca acaggaggca cgacaaatac gcagactctg     1380
ggcttcagcc aaggtgggcc taatacaatg gccaatcagg caaagaactg gctgccagga     1440
ccctgttacc gccagcagcg agtatcaaag acatctgcgg ataacaacaa cagtgaatac     1500
tcgtggactg gagctaccaa gtaccacctc aatggcagag actctctggt gaatccgggc     1560
ccggccatgg caagcacaa ggacgatgaa gaaaagtttt tcctcagag cggggttctc     1620 atctttggga gcaaggctc agagaaaaca aatgtggaca ttgaaaaggt catgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc aggggcccat ctgggcaaag     1860
attccacaca cggacggaca ttttcaccg tctccgctga tgggcggctt tggcctgaaa     1920
catcctccgc tcagatcct gatcaagaac acgcctgtac ctgcggatcc tccgaccacc     1980
ttcaaccagt caaagctgaa ctctttcatc actcagtatt ctactggcca agtcagcgtg     2040
gagatcgagt gggagctgca gaaggaaaac agcaagcgct ggaaccccga gatccagtac     2100
acctccaact actacaaatc tacaagtgtg gactttgctg ttaatacaga aggcgtgtac     2160
tctgaacccc gccccattgg cacccgttac ctcacccgta atctgtaa                  2208
```

<210> SEQ ID NO 13
<211> LENGTH: 2208
<212> TYPE: DNA
<213> ORGANISM: Artificial Sequence
<220> FEATURE:
<223> OTHER INFORMATION: capsid gene

<400> SEQUENCE: 13

```
atggctgccg atggttatct tccagattgg ctcgaggaca ctctctctga aggaataaga       60
cagtggtgga agctcaaacc tggcccacca ccaccaaagc ccgcagagcg cataaggac      120 gacagcaggg gtcttgtgct tcctgggtac aagtacctcg acccttcaa cggactcgac      180 aagggagagc cggtcaacga ggcagacgcc gcggccctcg agcacgacaa agcctacgac     240
cggcagctcg acagcggaga caacccgtac ctcaagtaca accacgccga cgcggagttt      300
caggagcgcc ttaaagaaga tacgtctttt gggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc aggaaccgga     480
```

```
aaggcgggcc agcagcctgc aagaaaaaga ttgaattttg gtcagactgg agacgcagac    540
tcagtacctg accccagcc tctcggacag ccaccagcag cccctctgg tctgggaact      600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg ctacagcac cccttggggg     840
tattttgact tcaacagatt ccactgccac ttctcaccac gtgactggca gcgactcatt    900
aacaacaact ggggattccg gcccaagaaa ctcagcttca agctcttcaa catccaagtt    960
aaggaggtca cgcagaatga aggcaccaag accatcgcca ataacctcac cagcaccatc   1020
caggtgttta cggactcgga gtaccagctg ccgtacgttc tcggctctgc ccaccagggc   1080
tgcctgcctc cgttcccggc ggacgtgttc atgattcccc agtacggcta cctaacactc   1140
aacaacggta gtcaggccgt gggacgctcc tccttctact gcctggaata ctttccttcg   1200
cagatgctga gaaccggcaa caacttccag tttacttaca ccttcgaggg cgtgcctttc   1260
cacagcagct acgcccacag ccagagcttg gaccggctga tgaatcctct gattgaccag   1320
tacctgtact acttgtctcg gactcaaaca acaggaggca cgacaaatac gcagactctg   1380
ggcttcagcc aagtgggcc taatacaatg gccaatcagg caaagaactg gctgccagga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatga caagccacaa ggacgatgaa gaaaagtttt tcctcagag cggggttctc    1620
atctttggga agcaaggctc agagaaaaca atgtggaca ttgaaaaggt tatgattaca    1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc agggggccat ctgggcaaag   1860
attccacaca cggacggaca ttttcacccc tctcccctca tgggtggatt cggacttaaa   1920
caccctcctc cacagattct gatcaagaac acgcctgtac ctgcggatcc tccgaccacc   1980
ttcaaccagt caaagctgaa ctctttcatc acccagtatt ctactggcca agtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa                2208
```

<210> SEQ ID NO 14
<211> LENGTH: 2208
<212> TYPE: DNA
<213> ORGANISM: Artificial Sequence
<220> FEATURE:
<223> OTHER INFORMATION: capsid gene

<400> SEQUENCE: 14

```
atggctgccg atggttatct tccagattgg ctcgaggaca accttagtga aggaattcgc    60
gagtggtggg cttttgaaacc tggagccccg aaacccaaag ccaaccagca aaagcaggac   120
gacggccggg gtctggtgct tcctggctac aagtacctcg gacccttcaa cggactcgac   180
aaggggagc ccgtcaacgc ggcggatgca gcggccctcg agcacgacaa ggcctacgac   240
cagcagctca aagcgggtga caatccgtac ctgcggtata accacgccga cgccgagttt   300
caggagcgtc tgcaagaaga tacgtctttt gggggcaacc tcgggcgagc agtcttccag    360
```

```
gccaagaagc gggttctcga acctctcggt ctggttgagg aaggcgctaa gacggctcct      420
ggaaagaaac gtccggtaga gcagtcgcca caagagccag actcctcctc gggcatcggc      480
aagacaggcc agcagcccgc taaaaagaga ctcaattttg gtcagactgg cgactcagag      540
tcagtccccg acccacaacc tctcggagaa cctccagcaa cccccgctgc tgtgggacct      600
actacaatgg cttcaggcgg tggcgcacca atggcagaca ataacgaagg cgccgacgga      660
gtgggtaatg cctcaggaaa ttggcattgc gattcccaat ggctgggcga cagagtcatc      720
accaccagca cccgaacctg ggccctgccc acctacaaca accacctcta caaacaaatt      780
tccagccaat caggagcctc gaacgacaat cactactttg gctacagcac cccttggggg      840
tattttgact tcaacagatt ccactgccac ttttcaccac gtgactggca aagactcatc      900
aacaacaact ggggattccg acccaagaga ctcaacttca agctctttaa cattcaagtc      960
aaagaggtca cgcagaatga cggtacgacg acgattgcca ataaccttac cagcaccatc     1020
caggtgttta cggactcgga gtaccagctg ccgtacgttc tcggctctgc ccaccagggc     1080
tgcctgcctc cgttcccggc ggacgtgttc atgattccgc aatacggcta cctgacgctc     1140
aacaacggga gtcaggcagt aggacgctct tcattttact gcctggagta ctttccttct     1200
cagatgctgc gtaccggaaa caactttacc ttcagctaca cttttgagga cgttcctttc     1260
cacagcagct acgctcacag ccagagtctg gaccgtctca tgaatcctct catcgaccag     1320
tacctgtatt acttgagcag aacaaacact ccaagtggaa ccaccacgca gtcaaggctt     1380
cagttttctc aggccggagc gagtgacatt cgggaccagt ctaggaactg gcttcctgga     1440
ccctgttacc gccagcagcg agtatcaaag acatctgcgg ataacaacaa cagtgaatac     1500
tcgtggactg gagctaccaa gtaccacctc aatggcagag actctctggt gaatccgggc     1560
ccggccatgg caagccacaa ggacgatgaa gaaaagtttt tccctcagag cggggttctc     1620
atctttggaa agcaaggctc agagaaaaca aatgtggaca ttgaaaaggt tatgattaca     1680
gacgaagagg aaatcaggac aaccaatccc gtggctacgg agcagtatgg ttctgtatct     1740
accaacctcc agagaggcaa cagacaagca gctaccgcag atgtcaacac acaaggcgtt     1800
cttccaggca tggtctggca ggacagagat gtgtaccttc agggcccat ctgggcaaag     1860 attccacaca cggacggaca ttttcacccc tctcccctca tgggtggatt cggacttaaa     1920
caccctcctc cacagattct catcaagaac cccgtac ctgcgaatcc ttcgaccacc     1980
ttcagtgcgg caaagtttgc ttccttcatc acacagtact ccacgggaca ggtcagcgtg     2040
gagatcgagt gggagctgca gaaggaaaac agcaaacgct ggaatccga aattcagtac     2100 acttccaact acaacaagtc tgttaatgtg gactttactg tagacactaa tggtgtttat     2160
agtgaacctc gccctattgg aacccggtat ctcacacgaa acttgtaa                  2208
```

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gtctgagtga ctagcattcg                                                  20

<210> SEQ ID NO 16
<211> LENGTH: 20
<212> TYPE: DNA

```
<213> ORGANISM: Artificial Sequence
<220> FEATURE:
<223> OTHER INFORMATION: primer

<400> SEQUENCE: 16
gcttactgaa gctcactgag                                                     20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
ttcgatcaac tacgcagaca g                                                   21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gtccgtgagt gaagcagata tt                                                  22

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
tctgatgctg tttccctgca gaca                                                24

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gacgtaaacg gccacaagtt                                                     20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gaacttcagg gtcagcttgc                                                     20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
gttactccca caggtgagc                                                      19
```

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
agaaacaagc cgtcattaaa cc                                              22

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
cttctcctcc gggctgtaat tagc                                            24

<210> SEQ ID NO 25
<211> LENGTH: 20
<212> TYPE: DNA
<213> ORGANISM: Artificial Sequence
<220> FEATURE:
<223> OTHER INFORMATION: capsid gene

<400> SEQUENCE: 25
tggatgactg catctttgaa                                                 20

<210> SEQ ID NO 26
<211> LENGTH: 22
<212> TYPE: DNA
<213> ORGANISM: Artificial Sequence
<220> FEATURE:
<223> OTHER INFORMATION: capsid gene

<400> SEQUENCE: 26
atggaaacta gataagaaag aa                                              22

<210> SEQ ID NO 27
<211> LENGTH: 17
<212> TYPE: DNA
<213> ORGANISM: Artificial Sequence
<220> FEATURE:
<223> OTHER INFORMATION: primer

<400> SEQUENCE: 27
attggcattg cgattcc                                                    17

<210> SEQ ID NO 28
<211> LENGTH: 22
<212> TYPE: DNA
<213> ORGANISM: Artificial Sequence
<220> FEATURE:
<223> OTHER INFORMATION: capsid gene

<400> SEQUENCE: 28
aaatcaggta tggctgccga tg                                              22

<210> SEQ ID NO 29
<211> LENGTH: 74
<212> TYPE: DNA
<213> ORGANISM: Artificial Sequence
<220> FEATURE:

-continued

```
<223> OTHER INFORMATION: capsid gene

<400> SEQUENCE: 29
aacgcccggg ctgtagttaa tgattaagcc gccatgctac ttatctacgt agccatggaa     60
actagataag aaag                                                      74

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cgagggcgat gccacctacg                                                20
```